(12) United States Patent
Dellinger et al.

(10) Patent No.: US 7,759,471 B2
(45) Date of Patent: Jul. 20, 2010

(54) MONOMER COMPOSITIONS FOR THE SYNTHESIS OF RNA, METHODS OF SYNTHESIS, AND METHODS OF DEPROTECTION

(75) Inventors: Douglas J. Dellinger, Boulder, CO (US); Zoltan Timar, Boulder, CO (US); Agnieszka Sierzchala, Boulder, CO (US); Geraldine Dellinger, Boulder, CO (US); Marvin H. Caruthers, Boulder, CO (US)

(73) Assignees: Agilent Technologies, Inc., Santa Clara, CA (US); Regents of the University Of Colorado, Denver, CO (US)

( * ) Notice: Subject to any disclaimer, the term of this patent is extended or adjusted under 35 U.S.C. 154(b) by 933 days.

(21) Appl. No.: 11/388,112

(22) Filed: Mar. 23, 2006

(65) Prior Publication Data

US 2007/0100136 A1    May 3, 2007

Related U.S. Application Data

(60) Provisional application No. 60/731,723, filed on Oct. 31, 2005.

(51) Int. Cl.
*C07H 19/00* (2006.01)
*C07H 19/067* (2006.01)
*C07H 19/167* (2006.01)
*C07H 21/02* (2006.01)

(52) U.S. Cl. .............. 536/22.1; 536/23.1; 536/25.31
(58) Field of Classification Search .............. 536/22.1, 536/23.1, 25.31, 25.2
See application file for complete search history.

(56) References Cited

OTHER PUBLICATIONS

Greene et al. Protective Groups in Organic Synthesis, 1999, John Wiley & Sons, Inc., 3rd ed., p. 17-23, 179-189 and 494-550.*
Boger, D.L. Modern Organic Synthesis, 1999, TSRI Press, p. 4-6 and 24.*
Soll et al. RNA, 2001, Elsevier Science Ltd., 1st ed., p. 91-98.*
Losse, Gunter et al., "Synthese von 2'-(tert-Butyloxycarbonyl)ribonucleosides", Synthesis, Nov. 1990, pp. 1035-1036, vol. 11.
Schneiderwind, Ruth G.K. et al., "Die 2,2,2,-t-Trichlor-t-Butyloxycarbonyl-Gruppe, Eine Neue N-Schutzgruppe Fur Oligonucleotidsynthesen", Tetrahedron, 1983, pp. 2007-2210., vol. 39, No. 13.
Green, Theodora W. et al., "Protective Groups in Organic Synthesis", Third Edition, Published 1999, pp. 179-187 and 494-550, John Wiley and Sons, Inc.
PCT/US07/64636 International Search Report and Written Opinion of International Searching Authority,9 pages, dated Aug. 22, 2008.

* cited by examiner

*Primary Examiner*—Shaojia Anna Jiang
*Assistant Examiner*—Jonathan S Lau

(57) ABSTRACT

Nucleotide monomers, polynucleotides, methods of making each, methods of deprotecting each, and the like are disclosed herein.

22 Claims, 14 Drawing Sheets

Group I

Group V

Group II

Group VI

Group III

Group VIIa   Group VIIb

Group IVa   Group IVb

Group VII

SEQUENCE LISTING

<160> NUMBER OF SEQ ID NOS: 1

<210> SEQ ID NO 1
<211> LENGTH: 18
<212> TYPE: RNA
<213> ORGANISM: Artificial Sequence
<220> FEATURE:
<223> OTHER INFORMATION: Chemically Synthesized

<400> SEQUENCE: 1
gucaccagcc cacuugag                                              18

MONOMER COMPOSITIONS FOR THE SYNTHESIS OF RNA, METHODS OF SYNTHESIS, AND METHODS OF DEPROTECTION

CROSS-REFERENCE TO RELATED APPLICATION

This application is related to copending U.S. provisional application entitled, "METHODS FOR DEPROTECTING POLYNUCLEOTIDES," having Ser. No. 60/731,723, filed Oct. 31, 2005, which is entirely incorporated herein by reference.

This application is related to copending U.S. Utility patent application entitled "MONOMER COMPOSITIONS FOR THE SYNTHESIS OF POLYNUCLEOTIDES, METHODS OF SYNTHESIS, AND METHODS OF DEPROTECTION" filed on Mar. 23, 2006 to Dellinger et al. and accorded Ser. No. [11/387,388], which is entirely incorporated herein by reference.

This application is related to copending U.S. Utility patent application entitled "CLEAVABLE LINKERS FOR POLYNUCLEOTIDES" filed on Mar. 23, 2006 to Dellinger et al. and accorded Ser. No. [11/389,388], which is entirely incorporated herein by reference.

This application is related to copending U.S. Utility patent application entitled "CLEAVABLE THIOCARBONATE LINKERS FOR POLYNUCLEOTIDE SYNTHESIS" filed on Mar. 23, 2006 to Dellinger et al. and accorded Ser. No. [11/389,326], which is entirely incorporated herein by reference.

This application is related to copending U.S. Utility patent application entitled "PHOSPHORUS PROTECTING GROUPS" filed on Mar. 23, 2006 to Dellinger et al. and accorded Ser. No. [11/388,339], which is entirely incorporated herein by reference.

BACKGROUND

Advances in the chemical synthesis of oligoribonucleotides have not kept pace with the many advances in techniques developed for the chemical synthesis of oligodeoxyribo-nucleotides. The synthesis of RNA is actually a much more difficult task than the synthesis of DNA. The internucleotide bond in native RNA is far less stable than in the DNA series. The close proximity of a protected 2'-hydroxyl to the internucleotide phosphate presents problems, both in terms of the formation of the internucleotide linkage and in the removal of the 2'-protecting group once the oligoribonucleotide has been synthesized (See FIG. 1).

Only recently has there been a great demand for small synthetic RNA. The discoveries of the RNAi pathway and small RNAs, such as siRNA, miRNAs and ntcRNAs associated with the RNA interference pathway is primarily responsible for this increased demand. Most recent attempts at the chemical synthesis of oligoribonucleotides have followed the synthetic strategy for the chemical synthesis of oligodeoxyribonucleotides: the standard phosphoramidite approach [Matteucci, M. D., Caruthers, M. H. *J Am. Chem. Soc.* 1981, 103, 3186-3191]. Such methods proceed by the step-wise addition of protected ribonucleoside phosphoramidite monomers to a growing RNA chain connected to a solid phase support. However, efficient solid phase synthesis of oligoribonucleotides still poorly compared to the efficiency of oligodeoxyribonucleotides synthesis.

Until recently, the typical approach to RNA synthesis utilized monomers whereby the 5'-hydroxyl of the ribonucleoside was protected by the acid-labile dimethoxytrityl (DMT) protecting group. Various protecting groups have been placed on the 2'-hydroxyl to prevent isomerization and cleavage of the internucleotide bond during the acid deprotection step. By using this as a starting point for RNA synthesis, researchers have focused on finding an ideal 2'-protecting group compatible with acid deprotection. Research directed toward the discovery of this ideal 2'-protecting group has taken two primary courses: the use of acid-stable 2'-protecting groups and the use of acid-labile 2'-protecting groups. The use of acid-stable 2'-protecting groups has been quite limiting from a chemical perspective, since there are not many options available when the base lability of RNA is considered. Acid-stable protecting groups are typically base-labile or nucleo-phile-labile (e.g., removed by a strong base or a strong nucleophile). General base-labile protecting groups are removed by elimination or fragmentation subsequent to proton abstraction by a strong base. An example of this type of protecting group is a propionitrile-containing protecting group, which is removed by beta-elimination to form acrylonitrile after a proton is abstracted from the methylene carbon adjacent to the nitrile group. It is difficult to use these types of protecting groups on the 2'-hydroxyl of RNA since subsequent proton abstraction from the ensuing 2'-hydroxyl results in cleavage of the internucleotide bond via formation of a 2'-3' cyclic phosphate and destruction of the RNA.

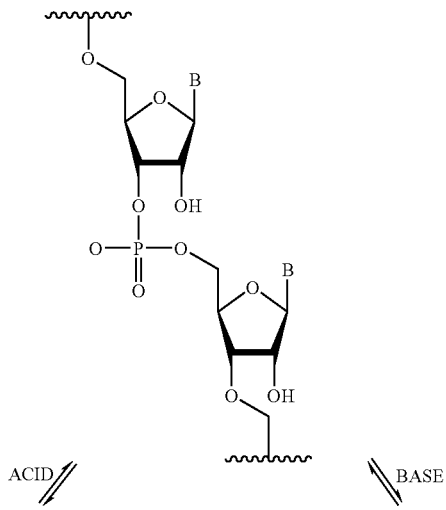

-continued

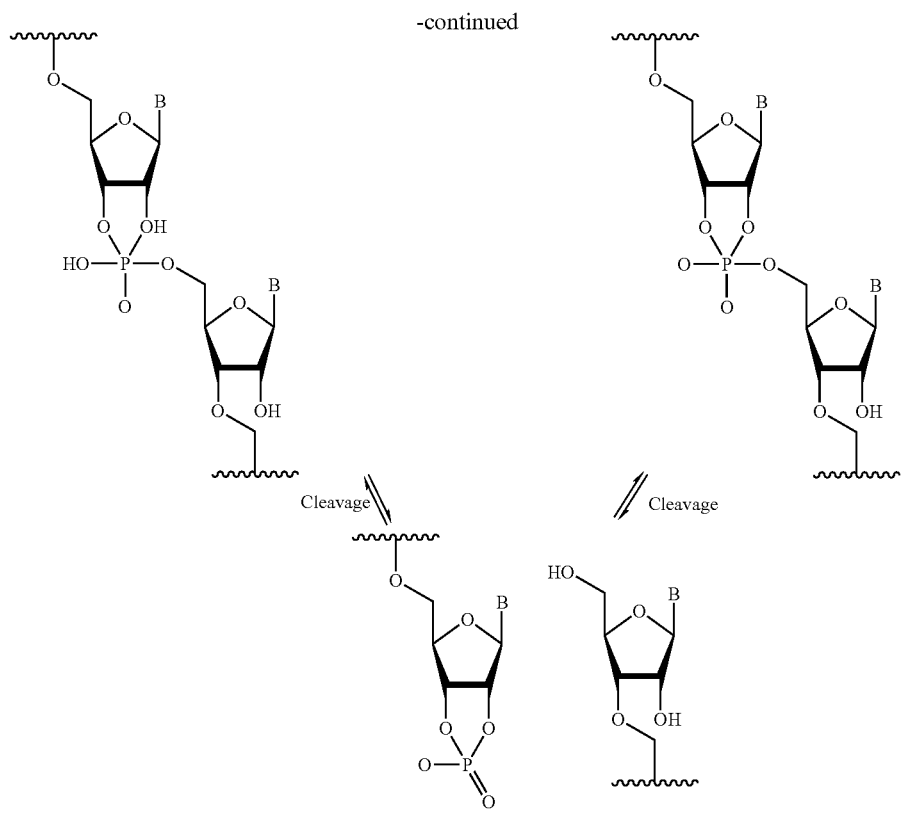

This approach is therefore only viable if the pH conditions used for proton abstraction from the protecting group are below pH 11, the pH at which proton abstraction from the 2'-hydroxyl begins to give rapid cleavage of the internucleotide bond. The approach of using a general base-labile protecting group for the 2'-hydroxyl has been further stymied by the necessary use of weak bases during the oxidation and capping reactions that occur in the standard phosphoramidite oligonucleotide synthesis process.

Protecting groups that are removed by the weakly basic conditions below pH 11 (such that the 2'-hydroxyl is not appreciably deprotonated) are typically unstable to the conditions used for capping and oxidation. As a result, the approach of using general base-labile protecting groups for 2'-hydroxyl protection has rarely been pursued, and never enabled.

Alternatively, there have been many attempts at the use of nucleophile-labile protecting groups for the protection of the 2'-hydroxyl. The difficulty associated with the use of nucleophile-labile protecting groups is that most typical nucleophiles are governed by the Brønsted-type plot of nucleophilicity as a function of basicity: the stronger the nucleophilicity, the stronger the basicity. As a result, strong nucleophiles are usually also strong bases and therefore the use of strong nucleophiles for deprotection of the 2'-hydroxyl typically results in the destruction of the desired RNA product by a subsequent proton abstraction from the 2'-hydroxyl. The use of nucleophile-labile 2'-hydroxyl protecting groups for RNA synthesis has only been enabled by the use of fluoride ion, a silicon-specific nucleophile that is reactive with silanes and siloxanes at a wide variety of pH conditions.

The most popular of these acid-stable protecting groups seem to be the t-butyl-dimethylsilyl group known as TBDMS [Ogilvie et al., Can. J. Chem., Vol 57, pp. 2230-2238 (1979)]. Widely practiced in the research community, the use of TBDMS as 2'-protecting group, dominated the previously small market for chemical synthesis of RNA for a very long time [Usman et al. J. Am. Chem. Soc. 109 (1987) 7845], [Ogilvie et al. Proc. Natl. Acad. Sci. USA 85 (1988) 5764]. The oligoribonucleotide syntheses carried out therewith are, however, by no means satisfactory and typically produces poor quality RNA products.

Several publications have reported the migration of the alkylsilyl group under a variety of conditions [Scaringe et al, Nucleic Acids Res 18, (18) 1990 5433-5441; Hogrefe et al. Nucleic Acids Research, 1993, 21 (20), 4739-4741]. Also, the loss of the 2'-silyl group that occurs during the removal of exocyclic amine protecting groups has been widely described in the literature [Stawinski et. al. Nucleic Acids Res. 1988, 16 (19), 9285-9298]. Methods that use less stable exocyclic amine protecting groups such as phenoxyacetyl or methoxyacetyl were subsequently developed to circumvent this problem [Schulhof et al. Nucleic Acids Res. 1987 15(2) 397-416]. However, the synthesis of the 5'-O-dimethoxytrityl-2'-O-tert-butyldimethylsilyl-ribo-3'-O-(β-cyanoethyl, N-diisopropyl) phosphoramidite monomers is still challenging and costly due to the non-regioselective introduction of the 2'-silyl group and the added chemical requirements to prevent migration of the silyl group during the phosphoramidite production. It is also well known in the art that the coupling efficiency of these monomers is greatly decreased due to the steric hindrance of the 2'-TBDMS protecting group, thereby affecting the yield and purity of the full-length product, and also limiting the length of the oligoribonucleotide that can be achieved by this chemical synthesis.

The most recent acid-stable 2'-hydroxyl protection approach for RNA synthesis was developed by Pitsch et al. [U.S. Pat. No. 5,986,084] to try to circumvent the problems encountered with the previous 2'-silyl protecting groups. This approach also relies on the use of 2'-O-acetals groups further protected by an alkylsilane, which is removed by the silicon-specific nucleophile fluoride ion. Although somewhat less acid stable than TBDMS, it is used in combination with acid-labile 5'-protecting groups such as DMT or the 5'-9-phenylxanthen-9-yl (Pix) group shown below.

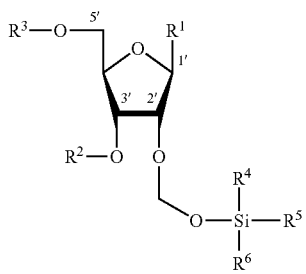

Because of the presence of the methylene group, this 2'-protecting group is less bulky than the TBDMS, allowing higher coupling efficiency. Since the protecting group is an acetal moiety, there is no significant problem of isomerization. The commercial protecting group typically used in this approach is the tri-isopropyloxymethyl derivative known by the abbreviation TOM. Although this protecting group scheme solves many of the problems encountered by the TBDMS chemistry, it suffers from other significant difficulties. The synthesis of the TOM-protected monomers is extremely difficult and low yielding. The protecting group itself requires a low yield multi-step synthesis prior to its placement on the nucleoside. The attachment to the nucleoside is performed through a nucleophillic displacement reaction by a 2'-3' alkoxide generated from a dialkyl tin reagent that produces a mixture of non-regioselective products that have to be separated and isolated by chromatography. In the case of the guanosine nucleoside, the tin reagents can preferentially react with the heterobase rather than the 2'-, 3'-hydroxyl moieties. In many cases, the overall yield of desired products from these reactions can be significantly less than 10%, rendering the monomer synthons and subsequent RNA products very expensive to produce.

Alternatively, many researchers have pursued the use of acid-labile groups for the protection of the 2'-hydroxyl moiety. The classic acid-labile protecting group is the 2'-acetal moiety, which was initially developed by Reese [Reese, C. B., Org. Biomol. Chem. 2005, 3(21), 3851-68], such as tetrahydropyran (THP) or 4-methoxy-tetrahydropyran (MTHP), 1-(2-chloroethoxy)ethyl (Cee) [O. Sakatsume et al. Tetrahedron 47 (1991) 8717-8728], 1-(2-fluorophenyl)-4-methoxypiperidin-4-yl (Fpmp) [M. Vaman Rao et al., J. Chem. Soc. Perkin Trans., Paper 2:43-55 (1993), Daniel C. Capaldi et al., Nucleic Acids Research, 22(12):2209-2216 (1994)].

One of the advantages of acetal protecting groups compared with silyl ethers protecting groups is that they can be introduced regioselectively into the 2' position through the use of the Markiewicz protecting group: tetraisopropyldisiloxane-1,3-diyl. This protecting group, also known as TIPS, simultaneously blocks the 5'- and 3'-hydroxyls to allow complete regioselective upon introduction of the acetal group on to the 2'-hydroxyl [Markiewicz W. T., J. Chem Research (S) 1979 24-25]. Another advantage is that the phosphoramidite coupling with 2'-acetal protected monomers is typically more efficient than with trialkyl silanes. The problems encountered when using the combination of 5'-O-DMT and 2'-O-acetals groups reside in the difficulty to find suitable 2'-O acetal groups that are both completely stable to the anhydrous acidic conditions used to remove the 5'O-DMT group and completely labile to the mild aqueous acid conditions used to remove this 2'-acetal protecting group, while not cleaving the internucleotide bond of the RNA. The removal of acetals that are stable under DMT deprotection conditions typically requires prolonged exposure to acidic conditions that degrade the RNA. To inhibit the loss of the 2'protecting group, the 5'-9-phenylxanthen-9-yl (Pix) group was applied, which is more labile than the DMT protecting group.

Even considering all of these innovations, the inability to find a viable combination of 2'-acetal and 5'-acid labile protecting groups that fits into the standard phosphoramidite synthesis cycle has resulted in these chemical schemes that were never effectively commercialized. Conversely, acetals used in combination with 5' protecting groups such as leuvinyl and 9-fluorenylmethyloxycarbonyl (FMOC) that are deprotected under non-acidic conditions like hydrazinolysis have not met significant success. One of the overriding reasons that 2'-acetals have not achieved wide acceptance is that they tend to be too stable under the required acid deprotection conditions once the monomers are incorporated onto an oligonucleotide, due to the close proximity of the protected 2'-hydroxyl to the internucleotide phosphate. There is a significant change in the stability of the protecting group once the oligonucleotide is produced. Conditions that can effectively remove an acetal group from a protected nucleoside monomer tend to be ineffective to remove the same group from the oligonucleotide.

To address this issue, Dellinger et al. developed 2'-orthoester protecting groups whose labiality on the oligonucleotide is less affected by close proximity to the internucleotide phosphate allowing effective removal under aqueous acid conditions that do not degrade the desired RNA product. The use of 2'-cyclic orthoesters was evaluated using a regioselective coupling procedure as well as a set of 5'-nucleophile labile carbonates [Marvin H. Caruthers, Tadeusz K. Wyrzkiewicz, and Douglas J. Dellinger. "Synthesis of Oligonucleotides and Oligonucleotide Analogs on Polymer Supports" *In Innovation and Perspectives in Solid Phase Synthesis: Peptides, Proteins and Nucleic Acids* (R. Epton, ed.) Mayflower Worldwide Limited, Birmingham, 39-44 (1994)]. Subsequently, Scaringe et. al. developed a set of 5'- and 2'-protecting groups that overcome the problems associated with use of 5'-DMT. This method uses a 5'-silyloxy protecting group [patents U.S. Pat. No. 5,889,136, U.S. Pat. No. 6,111,086, and U.S. Pat. No. 6,590,093] which require silicon-specific fluoride ion nucleophiles to be removed, in conjugation with the use of optimized 2'-orthoesters protecting groups (ACE). Although the coupling efficiency is greatly increased with the use of the ACE 2'-orthoester protecting group, and the final deprotection facile under pH conditions at which RNA is stable, the use of fluoride anions to deprotect the 5'-protecting groups prior each condensation cycle carries some disadvantages for routine synthesis of RNA and is even more problematic for large-scale synthesis of RNA. Because this chemistry requires atypical nucleoside protecting groups and custom synthesized monomers, namely on the 5'OH, it is difficult and time consuming to build RNA sequences that contain other commercially available phosphoramidite monomers, such as modified nucleotides, fluorescent labels, or anchors.

In order to incorporate a wide variety of alternative monomers and modifications using this chemistry, it is necessary to have each of them custom-synthesized with the appropriate 5'-silyloxy protecting group, thus significantly limiting the commercial applications for this chemistry. The ACE chemistry has the ability to produce very high quality RNA, but the reactions conditions are tricky and the synthesis not robust enough to routinely produce long sequences of RNAs. As a result, there is still clearly a need for the development of a chemical synthesis method for RNA that is simple and robust and produces high quality RNA products, while fitting into the standard phosphoramidite oligonucleotide synthesis approach. The commercial success of the ACE chemistry clearly illustrates the need to develop a RNA synthesis method that is founded upon mild and simple final deprotection conditions that will not affect the integrity of the final RNA product.

While protected, the RNA molecule has similar stability to the DNA molecule. Consequently, the final deprotection conditions to treat a synthetic RNA molecule are typically the same as the conditions to treat a synthetic DNA molecule prior to the removal of the 2'-hydroxyl protecting group. As a result, the current methods of RNA synthesis perform the final deprotection of the synthetic RNA in a 4-, 3-, or a 2-step fashion.

1. Deprotection of the protected phosphotriester, most commonly the cyanoethyl group (CNE), which is performed by brief exposure to ammonia (½ hr at room temperature) or in the case of the methyl group, by treatment with thiophenol for ½ hr at room temperature.
2. Cleavage of the oligoribonucleotides from the support performed under basic conditions, usually by exposure to ammonium hydroxide, anhydrous ammonia in an alcohol, methylamine, other alkyl amines, basic non-amine solutions such as potassium carbonate solutions, or non-nucleophillic bases such as 1,8-diazabicyclo [5.4.0]undec-7-ene (DBU) in organic solvents.
3. Deprotection of the nucleobases, which one most commonly protected on the exocyclic amine with protecting groups such as phenoxyacetyl (PAC), acetyl (Ac), isobutyryl (iBu) or benzoyl (Bz) and which are typically also removed under basic conditions. Most of the time, steps 2 and 3 are performed simultaneously.
4. Usually, the 2'-deprotection is performed post-cleavage of the oligonucleotide from the support. In the case of TBDMS and TOM chemistry, the oligoribonucleotide is exposed to fluoride anions to deblock the 2' hydroxyl groups after cleavage of the oligoribonucleotide from the support. In the case of the ACE chemistry, the 2'-O-orthoester group can be removed with acidic conditions after cleavage of the oligoribonucleotide from the support, but also can be kept and deprotected during shipment to the customers or after shipment by the customers (this procedure allows keeping the oligoribonucleotide intact longer, since RNA is very sensitive to nuclease RNase degradation).

Steps 1-3 can be performed simultaneously, when appropriate, making it a 2-step deprotection process, or step 1 can be performed independently, and steps 2-3 combined, making it a 3-step final deprotection process.

The removal of the 2'-hydroxyl protecting group is problematic for both the 3- and 2-step processes. In the 3-step process, the phosphorus protecting group is typically removed first, while the oligoribonucleotide is still attached to a solid support. In the second step, the heterobase protecting groups are removed using a nucleophillic base like ammonia or methyl amine, also which usually result in the cleavage of the oligoribonucleotide from the support.

Finally, a fluoride ion-based solution under neutral, mildly acidic, or mildly basic conditions (TBDMS, TOM) [Pitsch, et. al. Helv. Chim. Acta, 2001, 84, 3773-3795] or a weak acidic solution is used to remove the ACE 2'-hydroxyl protecting group [Scaringe et al, Nucleic Acids Res 18, (18) 5433-5441 (1990); Scaringe et al, J. Am. Chem. Soc., 120, 11820-11821 (1998)]. This process requires that the 2'-hydroxyl protecting group is orthogonally stable to the deblock conditions utilized to remove the protecting group for the 3'- or 5'-hydroxyl functional during the chemical synthesis process, and stable to the conditions utilized for deprotection of the phosphorus protecting groups and the heterobase protecting groups. Most often it is seen that a loss of the 2'-protecting group occurs to some extent during one of these previous deblock or deprotection processes. The result is modification of the desired RNA strand or cleavage of the desired RNA product.

Modification and cleavage decreases the yield and quality of the desired RNA products and can often prevent synthesis and isolation of oligonucleotide sequences significantly longer than 15 or 20 nucleotides in length. In the case of the use of a fluoride ion solution for deprotection of the 2'-hydroxy group, removal of residual fluoride ions requires additional steps and can be quite difficult and time consuming.

In the 3-step process, removal of the phosphorus protecting groups is accomplished simultaneously with the removal of the heterobase protecting groups. This is usually accomplished using a nucleophillic base like ammonia or methylamine. Most often the phosphorus-protecting group is removed using a beta-elimination reaction such as the formation of acrylonitrile from a 3-hydroxypropionitrile ester. However, the use of this system for the protection of the internucleotide phosphodiester linkage, followed by simultaneous deprotection during cleavage of the heterobase protecting groups, results in a number of notable side reactions that affect the yield and purity of the final product. The use of protecting groups that are susceptible to cleavage by proton abstraction followed by beta-elimination generally decreases the reactivity of the active phosphorus intermediate due to their electron withdrawing nature, and this effect lowers the per-cycle coupling efficiency. In addition, the elimination products such as acrylonitrile are reactive toward the heterobases and often form base adducts that result in undesired modifications.

SUMMARY

Nucleotide monomers, polynucleotides, methods of making each, methods of deprotecting each, and the like are disclosed herein. An embodiment of a nucleotide monomer, among others, includes a structure I as described herein.

Another embodiment of a nucleotide monomer, among others, includes a structure II as described herein.

Another embodiment of the polynucleotide, among others, includes a polynucleotide that include combinations of nucleotide moieties such as, but not limited to, structure I, structure II, nucleotide moities having one or more protecting groups as described herein, nucleotide moieties not including protecting groups, nucleotide moieties known in the art, combinations thereof, and the like.

An embodiment of deprotecting polynucleotides, among others, includes: providing a polynucletide including combinations of nucleotide moieties such as, but not limited to, structure I, structure II, nucleotide moities having one or more protecting groups as described herein, nucleotide moieties not including protecting groups, nucleotide moieties known in the art, combinations thereof, and the like; and deprotecting the 2'-hydroxyl protecting group and the exocyclic amino protecting group in a solution including an α-effect nucleophile, wherein the solution is at a pH of about 4 to 10, wherein the α-effect nucleophile has a pKa of about 4 to 13.

An embodiment of deprotecting polynucleotides, among others, includes: synthesizing on a solid support a polynucleotide including combinations of nucleotide moieties such as, but not limited to, structure I, structure II, nucleotide moities having one or more protecting groups as described herein, nucleotide moieties not including protecting groups, nucleotide moieties known in the art, combinations thereof, and the like; introducing the polynucleotide to a solution including an α-effect nucleophile, wherein the solution is at a pH of about 6 to 11, wherein the α-effect nucleophile has a pKa of about 4 to 13; and deprotecting the 2'-hydroxyl protecting group.

Additional objects, advantages, and novel features of this disclosure shall be set forth in part in the descriptions and examples that follow and in part will become apparent to those skilled in the art upon examination of the following specifications or may be learned by the practice of the disclosure. The objects and advantages of the disclosure may be realized and attained by means of the instruments, combinations, compositions, and methods particularly pointed out in the appended claims.

BRIEF DESCRIPTION OF THE DRAWINGS

Reference is now made to the following drawings. Note that the components in the drawings are not necessarily to scale.

DETAILED DESCRIPTION

Figure 1:
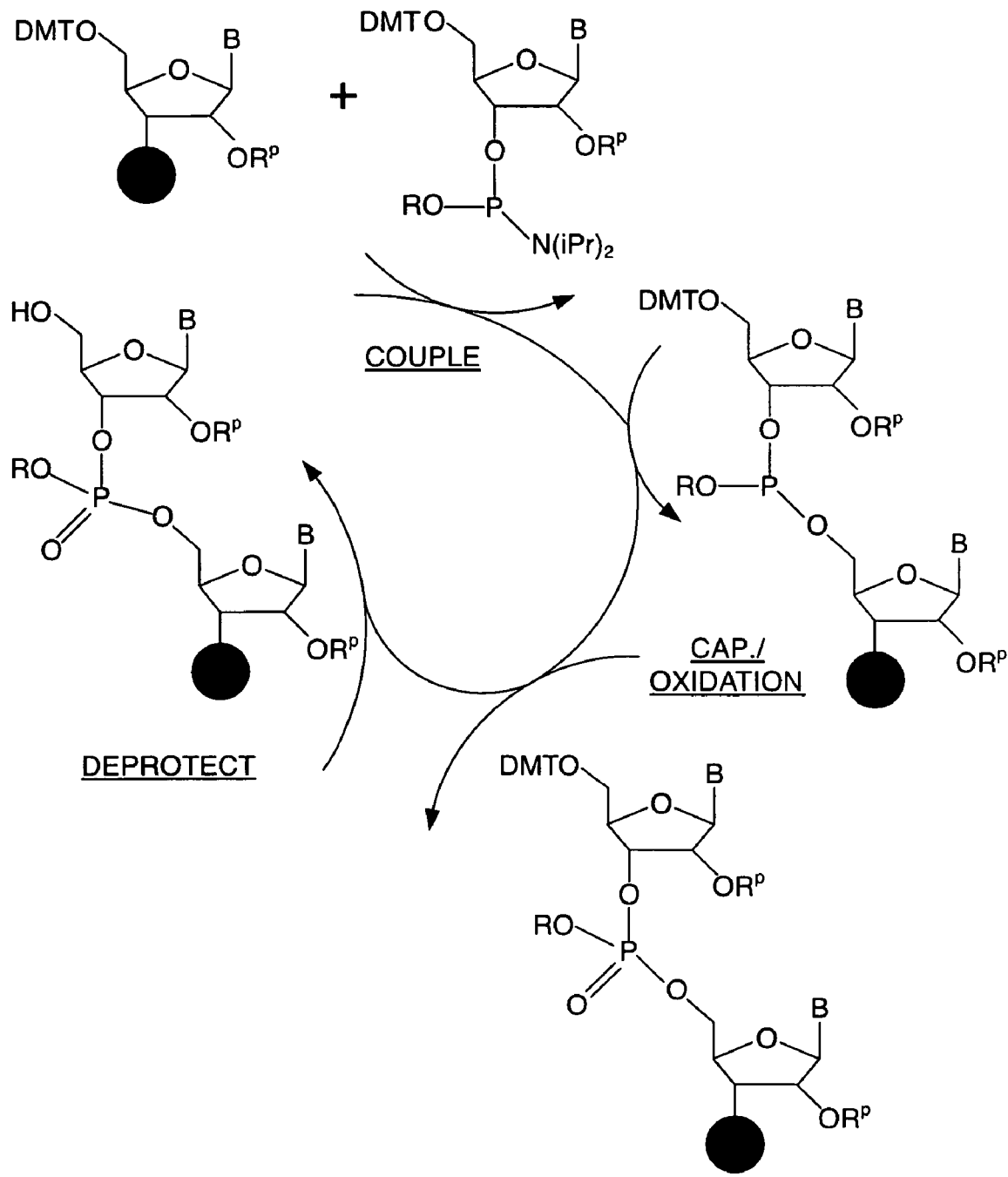
FIG. 1 schematically illustrates a prior art multi-step RNA synthesis method.
Figure 2A:
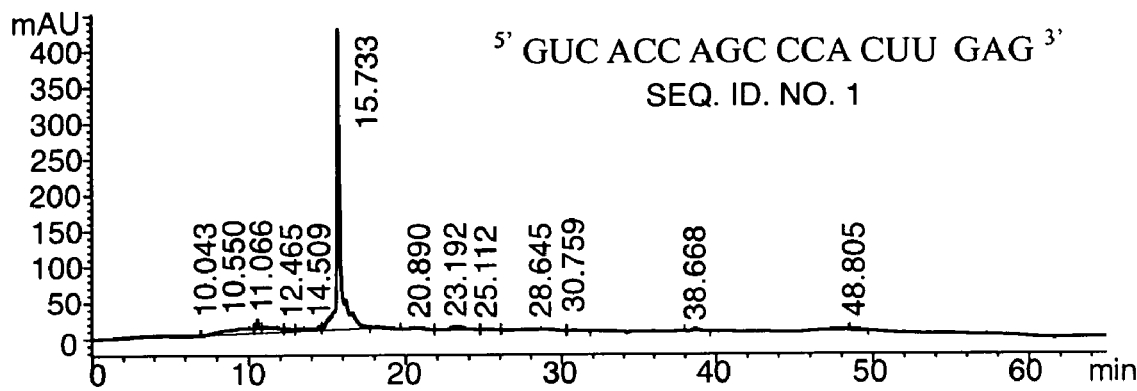
FIGS. 2A through 2E illustrate chromatograph of a synthetic RNA and a solution of 5% hydrogen peroxide in a solution having a pH of about 9 at various times (FIG. 2A (time$_{RNA}$=0), FIG. 2B (time$_{HP}$=0), FIG. 2C (time=3 hours), FIG. 2D (time=12 hours), and FIG. 2E (time=24 hours)).
Figure 2B:
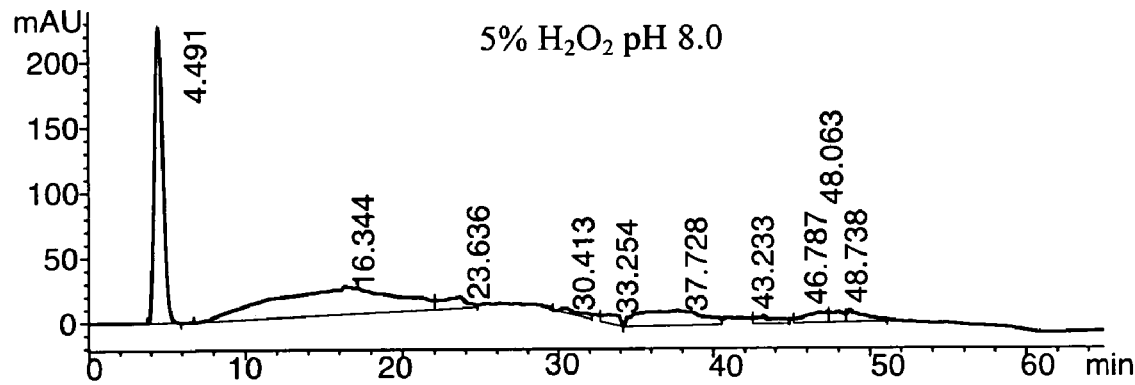
Figure 2C:
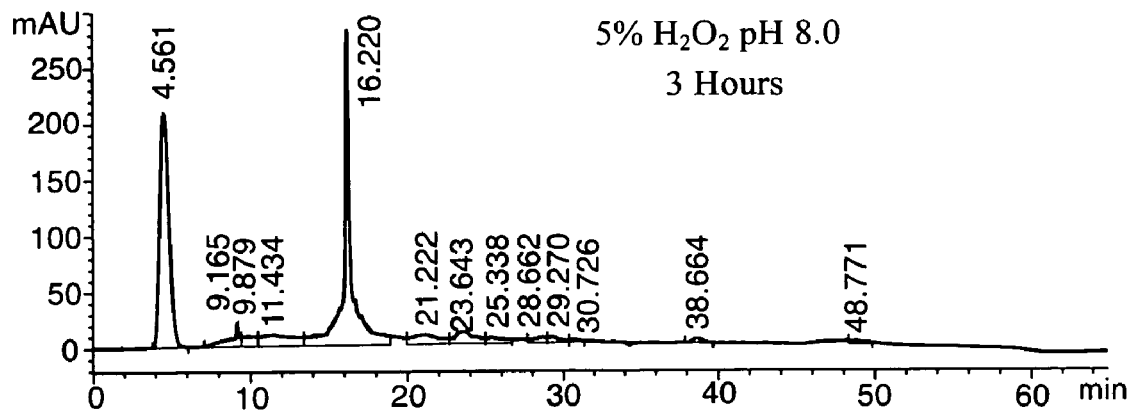
Figure 2D:
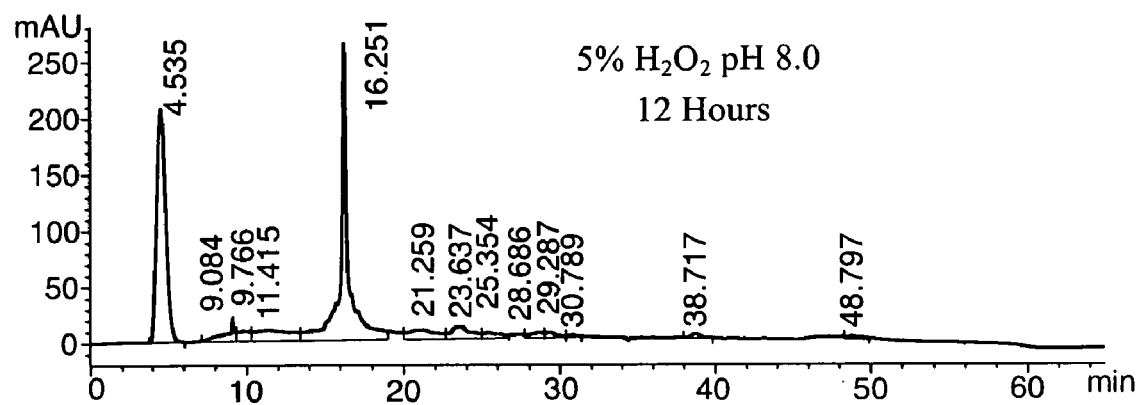
Figure 2E:
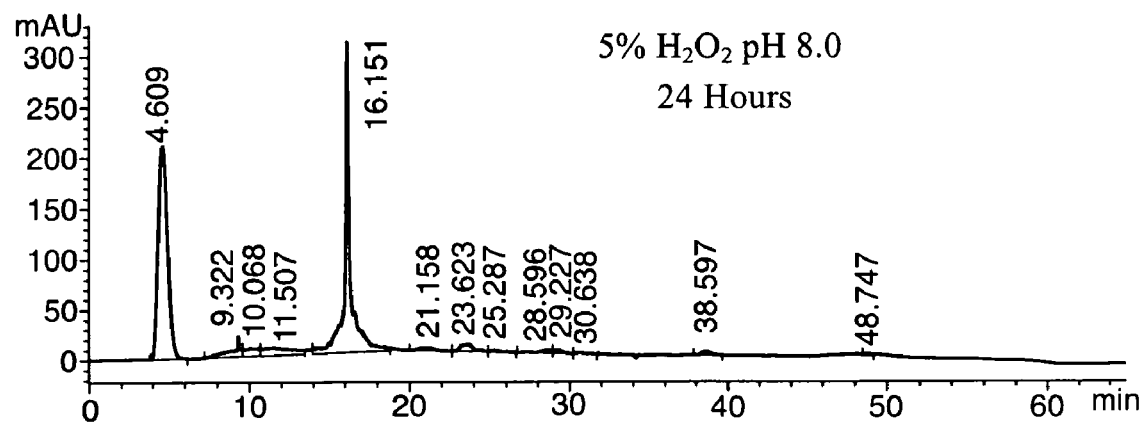

Embodiments of the present disclosure employ, unless otherwise indicated, conventional techniques of synthetic organic chemistry, biochemistry, molecular biology, and the like, which are within the skill of one in the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.), but some errors and deviations should be accounted for in the specification. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that unless otherwise indicated, the present disclosure is not limited to particular materials, reagents, reaction materials, manufacturing processes, or the like, as such may vary. It is also to be understood that the terminology used herein is for purposes of describing particular embodiments only, and is not intended to be limiting. It is also possible in the present disclosure that steps may be executed in different sequence where this is logically possible.

It must be noted that, as used in the specification and the appended claims, the singular forms "a," "an" and "the" include plural referents unless the context clearly dictates otherwise. Thus, for example, reference to "a support" includes a plurality of supports. In this specification and in the claims that follow, reference will be made to a number of terms that shall be defined to have the following meanings, unless a contrary intention is apparent.

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide" and a "nucleotide moiety" refer to a subunit of a nucleic acid (whether DNA or RNA or an analogue thereof) which may include, but is not limited to, a phosphate group, a sugar group and a nitrogen containing base, as well as analogs of such sub-units. Other groups (e.g., protecting groups) can be attached to the sugar group and nitrogen containing base group.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangable in most instances. One skilled in the art would have the understanding that additional modification to the nucleoside may be necessary, and one skilled in the art has such knowledge.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

A "polynucleotide intermediate" references a molecule occurring between steps in chemical synthesis of a polynucleotide, where the polynucleotide intermediate is subjected to further reactions to get the intended final product (e.g., a phosphite intermediate, which is oxidized to a phosphate in a later step in the synthesis), or a protected polynucleotide, which is then deprotected.

An "oligonucleotide" generally refers to a nucleotide multimer of about 2 to 100 nucleotides in length, while a "polynucleotide" includes a nucleotide multimer having any number of nucleotides greater than 1. The terms "oligonucleotide" and "polynucleotide" are often used interchangeably, consistent with the context of the sentence and paragraph in which they are used in.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its deravitives, inosine and its deravitives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

A "group" includes both substituted and unsubstituted forms. Typical substituents include one or more lower alkyl, amino, imino, amido, alkylamino, arylamino, alkoxy, aryloxy, thio, alkylthio, arylthio, or aryl, or alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are typically chosen so as not to substantially adversely affect reaction yield (for example, not lower it by more than 20% (or 10%, or 5%, or 1%) of the yield otherwise obtained without a particular substituent or substituent combination). An "acetic acid" includes substituted acetic acids such as di-chloroacetic acid (DCA) or tri-chloroacetic acid (TCA).

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

A "protecting group" is used in the conventional chemical sense to reference a group, which reversibly renders unreactive a functional group under specified conditions of a desired reaction, as taught, for example, in Greene, et al., "Protective Groups in Organic Synthesis," John Wiley and Sons, Second Edition, 1991, which is incorporated herein by reference. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "O-protecting group" refers to a protecting group where the protected group is a hydroxyl. A "reactive-site hydroxyl" is the terminal 5'-hydroxyl during 3'-5' polynucleotide synthesis and is the 3'-hydroxyl during 5'-3' polynucleotide synthesis. An "acid-labile protected hydroxyl" is a hydroxyl group protected by a protecting group that can be removed by acidic conditions. Similarly, an "acid-labile protecting group" is a protecting group that can be removed by acidic conditions.

A "linking moiety" is a group known in the art to connect nucleotide moieties in a polynucleotide or oligonucleotide compound.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. For example the term "alkyl" can refer to straight or branched chain hydrocarbon groups, such as methyl, ethyl, n-propyl, i-propyl, n-butyl, i-butyl, t-butyl, pentyl, hexyl, heptyl, octyl, and the like. Likewise, cycloalkyls have from about 3 to about 10 carbon atoms in their ring structure, and alternatively about 5, 6 or 7 carbons in the ring structure. The term "alkyl" is also defined to include halosubstituted alkyls and heteroatom substituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen thus: R—O—. In this function, R represents the alkyl group. An example would be the methoxy group $CH_3O$—.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics."

The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like.

The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocyclyls).

The terms "halogen" and "halo" refer to fluorine, chlorine, bromine, and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

When used herein, the terms "hemiacetal", "thiohemiacetal", "acetal", and "thioacetal", are recognized in the art, and refer to a chemical moiety in which a single carbon atom is geminally disubstituted with either two oxygen atoms or a combination of an oxygen atom and a sulfur atom. In addition, when using the terms, it is understood that the carbon atom may actually be geminally disubstituted by two carbon atoms, forming ketal, rather than acetal, compounds.

The term "electron-withdrawing group" is art-recognized, and refers to the tendency of a substituent to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry 251-59, McGraw Hill Book Company, New York, (1977). Exemplary electron-withdrawing groups include nitro, acyl, formyl, sulfonyl, trifluoromethyl, cyano, chloride, and the like.

The term "electron-donating group" is art-recognized, and refers to the tendency of a substituent to repel valence electrons from neighboring atoms (i.e., the substituent is less electronegative with respect to neighboring atoms). Exemplary electron-donating groups include amino, methoxy, alkyl (including $C_{1-6}$ alkyl that can have a linear or branched structure), $C_{4-9}$ cycloalkyl, and the like.

The term "deprotecting simultaneously" refers to a process which aims at removing different protecting groups in the same process and performed substantially concurrently or concurrently. However, as used herein, this term does not imply that the deprotection of the different protecting groups occur at the same time or with the same rate or same kinetics.

As used herein, "dissociation constant" (e.g., an acid dissociation constant) has its conventional definition as used in the chemical arts and references a characteristic property of a molecule having a tendency to lose a hydrogen ion. The value of a dissociation constant mentioned herein is typically expressed as a negative log value (i.e., a pKd).

Discussion

The present disclosure includes nucleotide monomers and polynucleotide structures (e.g., synthetic ribonucleic acid (RNA)) including nucleotide moieties, where the nucleotide monomers and nucleotide moieties each include various types of protecting groups. The nucleotide monomers and nucleotide moieties can be used in conjunction with methods, processes, and/or compositions of the present disclosure, for the deprotection of polynucleotides. Embodiments of the present disclosure enable quantitative or quasi-quantitative and rapid synthesis of the desired deprotected full-length polynucleotide product.

Embodiments of the present disclosure also include methods, processes, compositions, and structures that enable the synthesis of polynucleotides (e.g., RNA) with greater efficiency and lower cost compared to previous methods. In particular, the present disclosure provides for methods, processes, compositions, and structures that overcome at least some of the degradation problems of polynucleotides (e.g., RNA) that occurs during the deprotection procedure due to the use of strongly basic conditions, by the use of peroxyanions in mildly basic solutions and protecting groups described herein (e.g., 2'-hydroxyl protecting groups, base protecting groups, and phosphorus protecting groups).

An advantage of an embodiment of the present disclosure is that the deprotection of the bases can be performed even after removal of the 2'-hydroxyl protecting groups as opposed to prior methods. Another advantage of an embodiment of the present disclosure is that the deprotection can be used also to cleave the protecting groups of the bases in polynucleotide synthesis where for example the oligodeoxynucleotide includes a nucleotide or a modified nucleoside, or a non-nucleoside moiety such as fluorescent labels that are sensitive to strong bases.

An exemplary method of deprotecting polynucleotides, among others, includes: providing a synthetically made ribonucleic acid (RNA) (e.g., synthesized on a solid support (e.g., bead, CPG, polymeric support, an array)), wherein the RNA, optionally, has at least one 2'-hydroxyl protecting group (e.g., a silyl protecting group, a silyloxy protecting group, a ester protective group, a carbonate protecting group, a thiocarbonate protecting group, a carbamate protecting group, an acetal protecting group, an acetaloxycarbonyl protecting group, an orthoester protecting group, an orthothioester protecting group, an orthoesteroxycarbonyl protecting group, an orthothioesteroxycarbonyl protecting group, orthoesterthiocarbonyl protecting group, orthothioesterthiocarbonyl protecting group, a thioacetal protecting group, a thioacetaloxycarbonyl protecting group, as well as other groups described herein, and combinations thereof), wherein the RNA, optionally, has at least one protected exocyclic amine on a heterocyclic base protected by a base protecting group (e.g., an acyl protective group, an oxycarbonyl protecting group, a thiocarbonyl protecting group, an alkyloxymethylcarbonyl protecting group (optionally substituted), an alkylthiomethylcarbonyl protecting group (optionally substituted), an aryloxymethylcarbonyl protecting group (optionally substituted), an arylthiomethylcarbonyl protecting group (optionally substituted), an dialkylformamidine protecting group (optionally substituted), a dialkylamidine protecting group (optionally substituted), as well as other groups described herein, and combinations thereof), wherein the RNA, optionally, has at least one protected imine on a heterocyclic base by a base protecting group (e.g., an acyl protecting group (optionally substituted), an alkyloxycarbonyl protecting group (optionally substituted), an aryloxycarbonyl protecting group (optionally substituted), an alkylthiocarbonyl protecting group (optionally substituted), an arylthiocarbonyl protecting group (optionally substituted), and combinations thereof), wherein, optionally, the RNA has at least one phosphorus protecting group (e.g., substituted and unsubstituted: alkyl, benzyl, alkylbenzyl, dialkylbenzyl, trialkylbenzyl, thioalkylbenzyl, phenylthiobenzyl, dithioalkylbenzyl, trithioalkylbenzyl, thioalkylhalobenzyl, alkyloxybenzyl, dialkyloxybenzyl, halobenzyl, dihalobenzyl, trihalobenzyl, esterified salicyl, alkylnitrile protecting groups, as well as other protecting groups described herein); deprotecting (e.g., deprotecting, simultaneously or independently, one or more of 2'-hydroxyl protecting group, the base protecting group, and/or the phosphorus protecting group) the RNA in a solution including an α-effect nucleophile (e.g., hydrogen peroxide, peracids, perboric acids, alkylperoxides, hydrogen peroxide salts, hydroperoxides, butylhydroperoxide, benzylhydroperoxide, phenylhydroperoxide, performic acid, peracetic acid, perbenzoic acid, chloroperbenzoic acid and all corresponding salts of these species, mixtures with other compounds (e.g., sodium formate) and combinations thereof), wherein the solution is at a pH of about 4 to 11 (e.g., a pH of about 6 to 11, and a pH of about 8 to 11), and wherein the α-effect nucleophile has a pKa of about 4 to 13; (prior to or after deprotecting) optionally, cleaving (e.g., simultaneously or independently) the RNA from the support; and optionally, precipitating the RNA out of the solution.

In another embodiment of the present disclosure, exemplary methods of deprotecting polynucleotides, among others, includes: synthesizing on a solid support a ribonucleic acid (RNA), wherein the RNA has at least one 2'-hydroxyl protecting group and at least one protected exocyclic amine on a heterocyclic base; wherein said 2'-hydroxyl group is protected with an orthoester protective group; introducing the RNA to a solution including an α-effect nucleophile, wherein the solution is at a pH of about 6 to 11 and wherein the α-effect nucleophile has a pKa of about 4 to 13; deprotecting said 2'-orthoester protecting group under acidic conditions; (prior to or after cleaving) optionally, simultaneously or independently cleaving the RNA from the support; and optionally, precipitating the RNA out of the solution.

In another embodiment of the present disclosure, exemplary methods of deprotecting polynucleotides, among others, includes: synthesizing on a solid support a ribonucleic acid (RNA), wherein the RNA has at least one 2'-hydroxyl protecting group and at least one protected exocyclic amine on a heterocyclic base; wherein said 2'-hydroxyl protecting group includes a acetal protective group; introducing the RNA to a solution including an α-effect nucleophile, wherein the solution is at a pH of about 6 to 11 and wherein the α-effect nucleophile has a pKa of about 4 to 13, deprotecting said 2'-acetal protecting group under acidic conditions; (prior to or after cleaving) optionally, simultaneously or independently cleaving the RNA from the support; and optionally, precipitating the RNA out of the solution.

In another embodiment of the present disclosure, exemplary methods of deprotecting polynucleotides, among others, includes: synthesizing on a solid support a ribonucleic acid (RNA), wherein the RNA has at least one 2'-hydroxyl protecting group and at least one protected exocyclic amine on a heterocyclic base; wherein said 2'-hydroxyl protecting group is trisiopropyloxymethyl (TOM) group; introducing the RNA to a solution including an α-effect nucleophile, wherein the solution is at a pH of about 6 to 11 and wherein the α-effect nucleophile has a pKa of about 4 to 13; subsequently, deprotecting said 2'-trisiopropyloxymethyl protecting group under fluoride anions conditions; optionally, cleaving the RNA from the support; and optionally, precipitating the RNA out of the solution.

In another embodiment of the present disclosure, exemplary methods of deprotecting polynucleotides, among others, includes: synthesizing on a solid support a ribonucleic acid (RNA), wherein the RNA has at least one 2'-hydroxyl protecting group and at least one protected exocyclic amine on a heterocyclic base; wherein said 2'-hydroxyl protecting group includes a tert-butyldimethylsilyl (TBDMS) protective group; introducing the RNA to a solution including an α-effect nucleophile, wherein the solution is at a pH of about 6 to 11 and wherein the α-effect nucleophile has a pKa of about 4 to 13; deprotecting said 2'-TBDMS protective group with fluoride anions; (prior to or after cleaving) optionally, simultaneously or independently cleaving the RNA from the support; and optionally, precipitating the RNA out of the solution.

In another embodiment of the present disclosure, exemplary methods of deprotecting polynucleotides, among others, include: synthesizing on a polystyrene solid support a ribonucleic acid (RNA), wherein the RNA has at least one phosphorus protecting group, at least one 2'-hydroxyl protecting group and at least one protected exocyclic amine on a heterocyclic base; wherein said phosphorus protecting group is a methyl and said 2'-hydroxyl protecting group is trisiopropyloxymethyl (TOM) group; deprotecting said methyl group with thiophenol or derivative of thiophenol; then deprotecting said 2'-trisiopropyloxymethyl protecting group under fluoride anions conditions; subsequently, introducing the RNA to a solution including an α-effect nucleophile, wherein the solution is at a pH of about 6 to 11 and wherein the α-effect nucleophile has a pKa of about 4 to 13; deprotecting the excocyclic amine protecting group; optionally, simultaneously or independently cleaving the RNA from the support; and optionally precipitating the RNA out of the solution.

In another embodiment of the present disclosure, exemplary methods of deprotecting polynucleotides, among others, include: synthesizing on a polystyrene solid support a ribonucleic acid (RNA), wherein the RNA has at least one phosphorus protecting group, at least one 2'-hydroxyl protecting group and at least one protected exocyclic amine on a heterocyclic base; wherein said phosphorus protecting group is a methyl and said 2'-hydroxyl protecting group is a tert-butyldimethylsilyl (TBDMS) protective group; deprotecting said methyl group with thiophenol or derivative of thiophenol; then deprotecting said 2'-TBDMS protecting group under fluoride anions conditions; subsequently, introducing the RNA to a solution including an α-effect nucleophile, wherein the solution is at a pH of about 6 to 11 and wherein the α-effect nucleophile has a pKa of about 4 to 13; deprotecting said exocyclic amine protective group; optionally, simultalneously or independently cleaving the RNA from the support; and optionally precipitating the RNA out of the solution.

In another embodiment of the present disclosure, exemplary methods of deprotecting polynucleotides, among others, includes: synthesizing optionally on a solid support a polynucleotide wherein the polynucleotide has at least one protected exocyclic amine on a heterocyclic base and at least one protected imine on a heterocyclic base; deprotecting the exocyclic amino groups by introducing the polynucleotide to a solution including an α-effect nucleophile, wherein the solution is at a pH of about 6 to 11, and wherein the α-effect nucleophile has a pKa of about 4 to 13; optionally, simultaneously or independently cleaving the polynucleotide from the support; and optionally, precipitating the polynucleotide out of the solution.

In another embodiment of the present disclosure, exemplary methods of deprotecting polynucleotides, among others, includes: synthesizing optionally on a solid support a polynucleotide wherein the polynucleotide has at least one protected exocyclic amine on a heterocyclic base, at least one protected imine on a heterocyclic base and at least one 2'-hydroxyl protecting group; deprotecting the exocyclic amino groups by introducing the polynucleotide to a solution including an α-effect nucleophile, and wherein the solution is at a pH of about 6 to 11 wherein the α-effect nucleophile has a pKa of about 4 to 13; optionally, simultaneously or independently cleaving the polynucleotide from the support; and optionally, precipitating the polynucleotide out of the solution.

In another embodiment of the present disclosure, exemplary methods of deprotecting polynucleotides, among others, includes: synthesizing optionally on a solid support a polynucleotide wherein the polynucleotide has at least one protected exocyclic amine on a heterocyclic base, at least one protected imine on a heterocyclic base and at least one 2'-hydroxyl protecting group; deprotecting the exocyclic amino groups and the 2'-hydroxyl protecting groups by introducing the polynucleotide to a solution including an α-effect nucleophile, wherein the solution is at a pH of about 6 to 11 and wherein the α-effect nucleophile has a pKa of about 4 to 13; optionally, simultaneously or independently cleaving the polynucleotide from the support; and optionally, precipitating the polynucleotide out of the solution.

2'-Hydroxyl Protecting Groups and Deprotection

Embodiments of the disclosure include nucleotide monomers and polynucleotide compounds including at least one nucleotide moiety unit, where the nucleotide monomer and the nucleotide moiety each include a 2'-hydroxyl protecting group and in some embodiments additional protecting groups. The nucleotide monomer and the nucleotide moiety are different, in at least one way, in that the nucleotide moiety is part of a polynucleotide compound, while the nucleotide monomer is not part of a polynucleotide compound. The nucleotide moiety includes a linking moiety that links a plurality of nucleotide moieties together (and/or to a substrate), while the nucleotide monomer does not include such a linking moiety. For the following discussion the structures will be referred to as "nucleotide monomer", but it is to be understood that the structures can be nucleotide moieties if a linking group is included in the structure to interconnect nucleotide moieties in a polynucleotide compound.

As mentioned above, embodiments of the disclosure can include nucleotide monomers having a 2'-hydroxyl protecting group. A variety of 2'-hydroxyl protecting groups have been used for RNA synthesis. The 2'-hydroxyl protecting groups can be used in conjunction with other protecting groups (e.g., base protecting groups and/or phosphorus protecting groups). In an embodiment of the present disclosure, the 2'-hydroxyl protecting groups can include, but are not limited to, groups that can be removed with peroxyanions as well as groups that have been specifically developed and optimized to be removed by peroxyanions. In addition, the 2'-hydroxyl protecting groups can include, but are not limited to, the structures (e.g., structure I) described in further detail below.

Exemplary 2'-hydroxyl protecting groups include, but are not limited to: acid-labile protecting groups, nucleophile-labile protecting groups, fluoride-labile protecting groups, and oxidative-labile protecting groups. These groups are attached to the 2'-oxygen through a variety of functionalities that include, but are not limited to, esters, carbonates, thiocarbonates, carbamates, acetals, thioacetals, carbonates of hemiacetals, carbonates of thiohemiacetals, orthoesters, thioorthoesters, carbonates of orthoesters, carbonates of thioorthoesters, silyl, siloxanes, carbonates and thiocarbonates of silanes, carbonates and thiocarbonates of siloxanes, silyl protected hemiacetals, carbonates and thiocarbonates of silyl protected hemiacetals, carbonates and thiocarbonates of hemiacetals, carbonates and thiocarbonates of thiohemiacetals, and a variety of substituted derivatives of any of the previously described functionalities.

The nucleotide monomer can include, but is not limited to, a structure such as structures I. The following structure illustrates embodiments that include 2'-hydroxyl protecting groups.

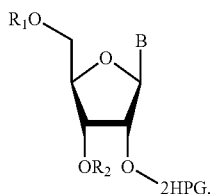

Structure I

B can include, but is not limited to, a base and a base including a protection group.

In addition, the nucleotide monomer can include, but is not limited to, a structure such as structures II. The following structure illustrates embodiments that include 2'-hydroxyl protecting groups.

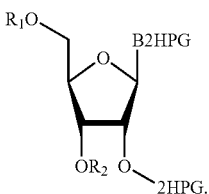

Structure II

For structure I and II, $R_1$ and $R_2$ are each independently selected from a group such as, but not limited to, H, a protecting group, and

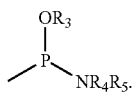

wherein only one of $R_1$ and $R_2$ is

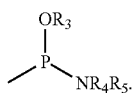

In an embodiment, $R_1$ and/or $R_2$ can include a linking moiety that interconnects the nucleotide moieties in a polynucleotide or connects to a substrate.

$R_3$ is a group such as, but not limited to, an alkyl group, an aryl group, a substituted alkyl, and a substituted aryl group. In an embodiment, R3 can include a linking moiety that interconnects the nucleotide moieties in a polynucleotide or connects to a substrate.

$R_4$ and $R_5$ are each independently selected from a group such as, but not limited to, an alkyl group, an aryl group, a substituted alkyl, and a substituted aryl group. In addition, $R_4$ and $R_5$ can be, optionally, cyclically connected to each other. In an embodiment, $R_4$ and/or $R_5$ can include a linking moiety that interconnects the nucleotide moieties in a polynucleotide.

In an embodiment, R1 and R2 may each individually be selected from one of the following: H, a protecting group, and:

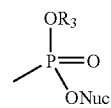

but where both R1 and R2 are not

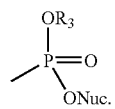

$R_3$ can include, but is not limited to, an alkyl group, a substituted alkyl group, an aryl group, and a substituted aryl group. In an embodiment, $R_3$ is optionally a linking moiety that links to another nucleotide moiety of a polynucleotide or connects to a substrate. Nuc is a nucleotide or polynucleotide.

In another embodiment, R1 and R2 can have the following structure:

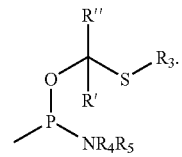

R' and R" are each individually a group such as, but not limited to, H, an alkyl group, an aryl group, a substituted alkyl, a substituted aryl group. In an embodiment, R' and/or R" can include a linking moiety that interconnects the nucleotide moieties in a polynucleotide or connects to a substrate.

$R_3$ is a group such as, but not limited to, an alkyl group, an aryl group, a substituted alkyl, and a substituted aryl group. In an embodiment, R3 can include a linking moiety that interconnects the nucleotide moieties in a polynucleotide or connects to a substrate.

$R_4$ and $R_5$ are each independently selected from a group such as, but not limited to, an alkyl group, an aryl group, a substituted alkyl, and a substituted aryl group. In addition, $R_4$ and $R_5$ can be, optionally, cyclically connected to each other. In an embodiment, $R_4$ and/or $R_5$ can include a linking moiety that interconnects the nucleotide moieties in a polynucleotide or connects to a substrate.

2HPG is a 2'-hydroxyl protecting group such as, but not limited to, one of the groups listed below I, II, III, IVa, IVb, V, VI, VIIa, VIb, and VIII:

Group I:

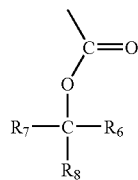

Group I $R_6$, $R_7$, and $R_8$ are each independently selected from a group such as, but not limited to, an alkyl group, a substituted alkyl, a substituted alkyl with an electron-withdrawing group, a substituted aryl group with an electron-withdrawing group, a group that is converted into an electron withdrawing group by oxidation (e.g., via peroxyanions), an aryl group, a substituted aryl group, where $R_6$, $R_7$, and $R_8$ are not each a methyl group, where $R_6$, $R_7$, and $R_8$ are not each an unsubstituted alkyl, and where $R_6$, $R_7$, and $R_8$ are optionally cyclically connected to each other.

Group II:

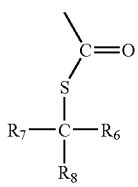

Group II $R_6$, $R_7$, and $R_8$ are each independently selected from a group such as, but not limited to, an alkyl group, an aryl group, a substituted alkyl group, and a substituted aryl group, and $R_6$, $R_7$, and $R_8$ are optionally cyclically connected to each other.

Group III:

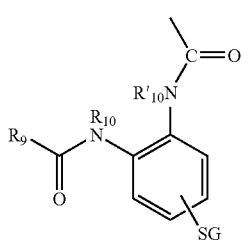

Group III $R_9$ is a group such as, but not limited to, an alkyl group, an aryl group, a substituted alkyl with an electron-withdrawing group, and a substituted aryl group with an electron-withdrawing group, where $R_{10}$ and $R'_{10}$ are each independently selected from a group such as, but not limited to, H, an alkyl group, and a substituted alkyl with an electron-withdrawing group.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. SG can include one or more groups, where each group is attached to one of the carbons in the carbon ring. SG is a group such as, but not limited to, H, an alkyl group, an aryl group, a substituted alkyl with an electron-donating group, and a substituted aryl group with an electron-donating group.

Group IVa and IVb:

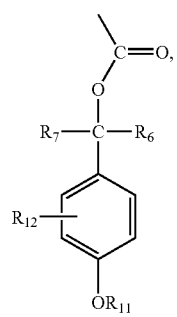

Group IVa

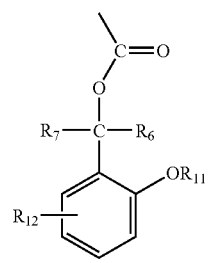

Group IVb $R_6$ and $R_7$ are independently selected from a group such as, but not limited to, an alkyl group, an aryl group, a substituted alkyl with an electron-withdrawing group, and a substituted aryl group with an electron-withdrawing group, $R_6$ and $R_7$ are optionally cyclically connected to each other or to the phenol and where $R_{11}$ is a group such as, but not limited to, an ester protecting group and silyl protecting group.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. $R_{12}$ can include one or more groups, where each group is attached to one of the carbons in the carbon ring. $R_{12}$ is a group such as, but not limited to, an alkyl group, an aryl group, a substituted alkyl with an electron-withdrawing group, and a substituted aryl group with an electron-withdrawing group.

Group V:

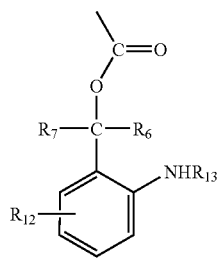

Group V $R_6$ and $R_7$ are independently selected from a group such as, but not limited to, an alkyl group, an aryl group, a substituted alkyl with an electron-withdrawing group, and a substituted aryl group with an electron-withdrawing group, where $R_6$ and $R_7$ are optionally cyclically connected to each other and where $R_{13}$ is an amide-protecting group.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. $R_{12}$ can include one or more groups, where each group is attached to one of the carbons in the carbon ring. $R_{12}$ is a group such as, but not limited to, an alkyl group, an aryl group, a substituted alkyl with an electron-withdrawing group, and a substituted aryl group with an electron-withdrawing group.

Group VI:

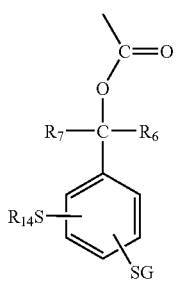

Group VI $R_6$ and $R_7$ are independently selected from a group such as, but not limited to, an alkyl group, an aryl group, a substituted alkyl with an electron-withdrawing group, and a substituted aryl group with an electron-withdrawing group, and $R_6$ and $R_7$ are optionally cyclically connected to each other.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. SG and $SR_{14}$ can each include one or more groups, where each group is attached to one of the carbons in the carbon ring. $SR_{14}$ is one or more thioether independently selected from a thioalkyl group, a thioaryl group, a substituted thioalkyl group, and a substituted thioaryl group. In an embodiment, $R_{14}$ includes, but is not limited to, an alkyl group, an aryl group, a substituted alkyl group, and a substituted aryl group. SG is a group such as, but not limited to, H, an alkyl group, an aryl group, a substituted alkyl with an electron-donating group, a substituted aryl group with an electron-donating group, and an electron-donating group in the ortho or para position to the thioether $SR_{14}$.

Groups VIIa and VIIb:

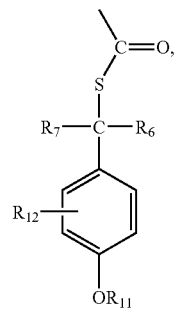

Group VIIa

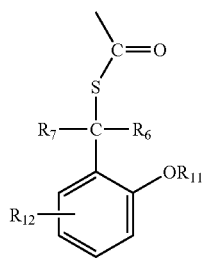

Group VIIb $R_6$ and $R_7$ are independently selected from a group such as, but not limited to, an alkyl group, an aryl group, a substituted alkyl with an electron-withdrawing group, and a substituted aryl group with an electron-withdrawing group, where $R_6$ and $R_7$ are optionally cyclically connected to each other or to the phenol and where $R_{11}$ is a group such as, but not limited to, an ester protecting group and silyl protecting group.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. $R_{12}$ can include one or more groups, where each group is attached to one of the carbons in the carbon ring. $R_{12}$ is a group such as, but not limited to, an alkyl group, an aryl group, a substituted alkyl with an electron-withdrawing group, and a substituted aryl group with an electron-withdrawing group.

Group VIII:

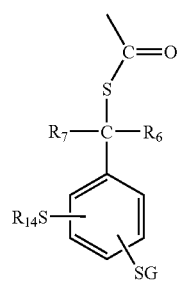

Group VIII $R_6$ and $R_7$ are independently selected from a group such as, but not limited to, an alkyl group, an aryl group, a substituted alkyl with an electron-withdrawing group, and a substituted aryl group with an electron-withdrawing group, where and $R_6$ and $R_7$ are optionally cyclically connected to each other.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. SG and $SR_{14}$ can each include one or more groups, where each group is attached to one of the carbons in the carbon ring. $SR_{14}$ is one or more thioethers independently selected from a thioalkyl group, a thioaryl group, a substituted thioalkyl group, and a substituted thioaryl group. In an embodiment $R_{14}$ can include, but is not limited to, an alkyl group, an aryl group, a substituted alkyl group, and a substituted aryl group. SG is a group such as, but not limited to, H, an alkyl group, an aryl group, a substituted alkyl with an electron-donating group, a substituted aryl group with an electron-donating group, and an electron-donating group in the ortho or para position to the thioether $SR_{14}$.

It should be noted that some properties may be considered when selecting a 2'-hydroxyl protecting group and these include, but are not limited to, whether the groups has specificity for introduction on the 2'-hydroxyl (regioselectivity), whether the group does not lead to isomerisation products, whether the group does not compromise coupling yield, and whether the group can be easily removed remove without degrading the RNA.

Regioselective Introduction

The 2'-hydroxyl protecting groups can be placed on the molecule in either a regioselective manner, a non-regioselective manner, or a regiospecific manner. In a regioselective manner, the protecting group is setup by various conditions and circumstances in the chemical reaction to react only with the hydroxyl region that is desired, in this case the 2'-hydroxyl.

An example of a regioselective protecting group is the dimethoxytrityl protecting group [Schaller, H.; Weimann, G.; Lorch, B.; Khorana, H. G., *J Am. Chem. Soc.* 1963, 85, 3821-3827, which is incorporated herein by reference]. The dimethoxytrityl protecting groups will regioselectively react with only the 5'-hydroxyl. This protecting group is regioselective because the rate of reaction of dimethoxytrityl chloride with the 5'-hydroxyl is at least 100 times faster than with either the 2' or 3' hydroxyls. The 2'-hydroxyl can then be regioselectively or non-regioselectively reacted with the desired 2'-protective group. In a regioselective manner, the desired 2'-hydroxyl protecting group is typically reacted with 5'-protected nucleosides using various asymmetric Lewis Acid catalysts. Although it is possible to find conditions and reagents that give some level of regioselectivity, complete regioselectivity is difficult to achieve using this method, and this approach tends to produce a mixture of structural isomers. The desired 2'-protected nucleoside must then be separated from the undesired 3'-protected nucleoside or the bis-2', 3'-protected nucleoside chromatographically. Typically this approach is used to enrich the amount of the desired 2'-protected nucleoside produced in order to decrease the cost of obtaining the correct 2'-protected nucleoside. Rarely has it been demonstrated that this approach achieves complete regioselectivity. Often differential regioselectivity is demonstrated for the different heterobase containing nucleosides. Complete regioselectivity may be obtained with one or more nucleosides, but usually one or more of the nucleosides show little or no regioselectivity resulting, in low synthetic yield of the desired monomer.

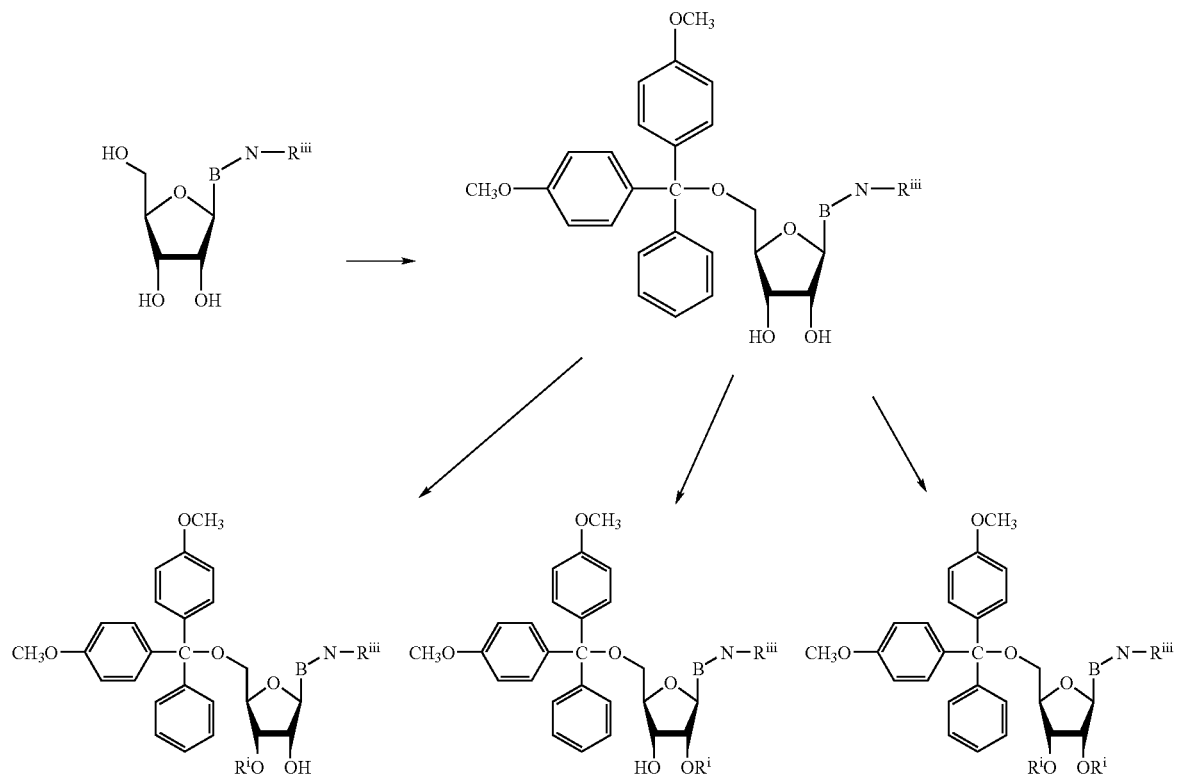

It is therefore most often preferable to utilize a regiospecific approach to protection of the 2'-hydroxyl. In a regiospecific manner a nucleoside, that can contain a heterobase protecting group, is typically then reacted on the 5' and 3' hydroxyls with an additional blocking group that transiently protects both positions simultaneously. An example of such a blocking group is the 1,3-tetraisopropyl disiloxane [Markiewicz W. T., *J Chem Research* (S) 1979 24-25)]. The desired 2'-hydroxyl protecting group is then reacted specifically with the 240 -hydroxyl.

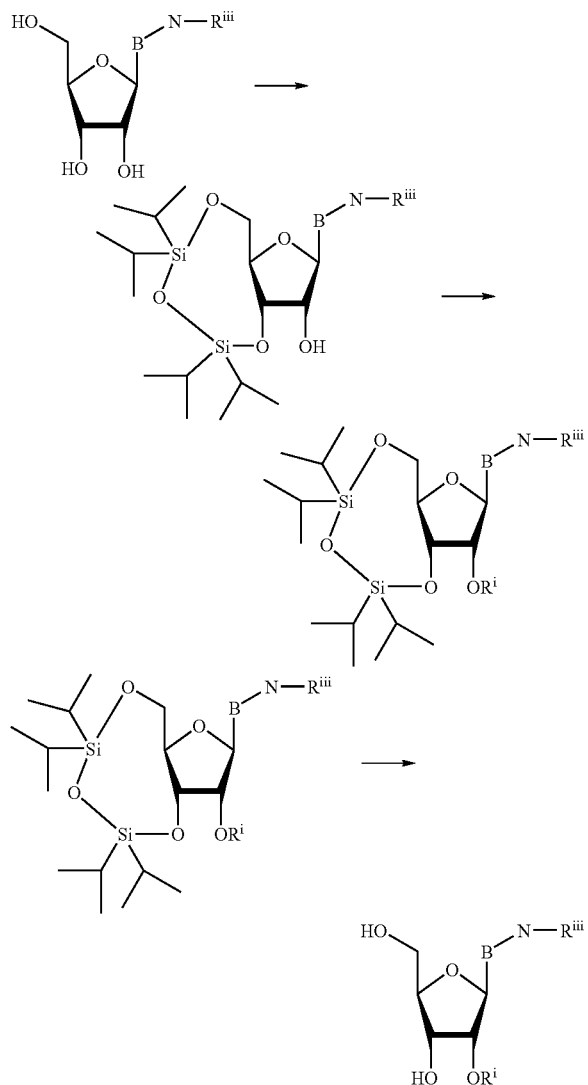

This is usually the most preferred method of protecting of the 2'-hydroxyl. However, there are several examples whereby the desired 2'-hydroxyl protecting group is incompatible with the blocking groups needed to transiently protect the 3' and 5' hydroxyls. As an example, the 1,3-tetraisopropyl disiloxane is a transient blocking group that is used to block the 5' and 3' hydroxyls simultaneously, allowing the 2'-hydroxyl to then be regioselectively reacted. The 1,3-tetraisopropyl disiloxane group is subsequently removed using a solution of fluoride ions. Due to the required deprotection conditions of the 1,3-tetraisopropyl disiloxane group, 2'-protecting groups that contain silyl or silicon atoms are not compatible with this regioselective approach [Beigelman, L, and Serebryany, V, *Nucleosides, Nucleotides, and Nucleic Acids*, 2003, Vol 22, 1007-1009, which is incorporated herein by reference].

Isomerization

Additionally, the stability of the 2'-hydroxyl protecting group to migration is an important factor that limits the scope and the usefulness of a variety of protecting group classes or species within a class of protecting group. Because the 2'-hydroxyl moiety is "cis" to the 3'-hydroxyl it can promote the isomerization of many classes of protecting groups from the 2'-hydroxyl to the 3'-hydroxyl and vise versa. Often this isomerization reaction is catalyzed by the addition of weak acids or weak bases. This becomes problematic for silica gel purification, since silica gel is weakly acidic and therefore protecting groups that are susceptible to acid catalyzed isomerization are difficult to purify by column chromatography. A similar reaction can occur during formation of the 3'-phosphoramidite. There are two basic methods for the formation of phosphoramidites. The first is through the use of a chlorophosphine [Beaucage, S. L.; Caruthers, M. H. *Tetrahedron Lett.* 1981, 22, 1859-1862, which is incorporated herein by reference]. The use of a chlorophosphine reagent requires exposure of the nucleoside to a weak base like triethyl amine or diisopropylethyl amine. Protecting groups that are susceptible to base catalyzed isomerization are difficult to phosphitylate by this method as shown below.

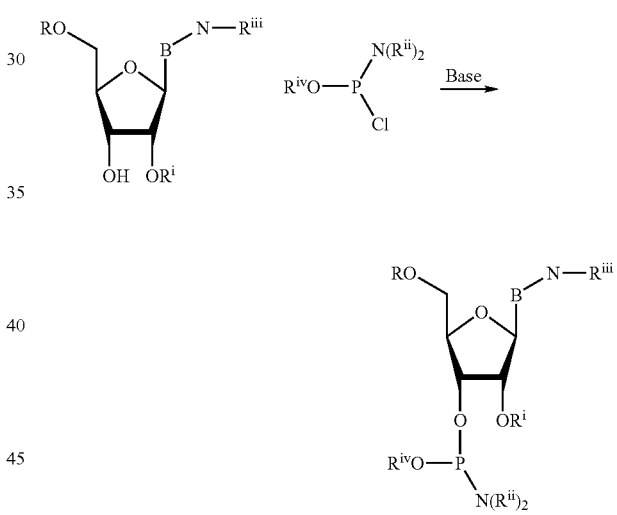

Alternatively, phosphoramidites can be prepared by the "bis-dialkylaminophosphine" method [Barone A D, Tang J Y, Caruthers M H, *Nucleic Acids Res.*, 1984, 12(10), 4051-61, which is incorporated herein by reference]. This method uses a weak acid such as tetrazole of the amine salt of tetrazole to catalyze the reaction of the bis-dialkylaminophosphine with the 3'-hydroxyl.

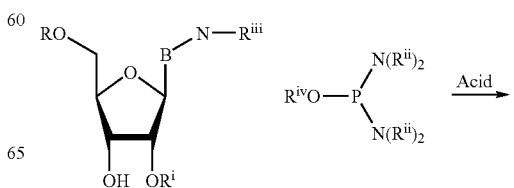

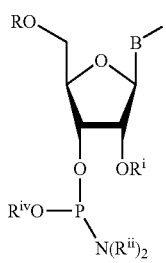

Protecting groups that undergo isomerization under these conditions can be difficult to phosphitylate forming the 3'-phosphoramidite. It is therefore preferable to utilize protecting group classes or species within a protecting group that are not susceptible to isomerization under either weak acid or weak base conditions. A clear example of a protecting group that can isomerize under weak acid and weak base conditions is the silyl TBDMS. Although unidentified by the authors, the original method published for the use of this protecting group for the 2'-hydroxyl [Usman N, Ogilvie K K, Jiang M Y, Cedergren R J, *J Am. Chem. Soc.*, 1987, 109(25), 7845-7854] gave only isomerized mixtures of the phosphoramidite monomers and as a result it was necessary to develop highly specialized techniques for preparation and purification to limit the amount of isomerized products in the phosphoramidite monomers. Another protecting group class that is particularly susceptible to isomerize is the ester class. The isomerization of esters can be inhibited by the use of large bulky alkyl or aryl groups. Therefore large bulky esters are particularly preferred as 2'-protecting groups over smaller groups like acetyl.

Carbonates and Thiocarbonates:

Carbonates and thiocarbonates do not undergo isomerization from the 2'hydroxyl to the 3' hydroxyl and vice versa. The chemical transition that would lead to isomerization always results in the formation of 2', 3'-cyclic carbonates, which are the thermodynamically favored product. The formation of 2', 3'-cyclic carbonates under acidic or basic conditions can be quite facile and lead to low yields of the desired 2'-protected product.

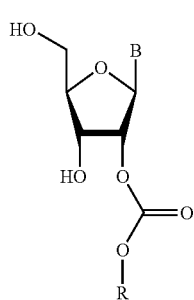
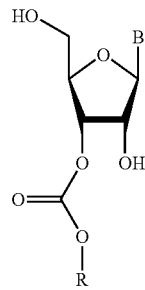

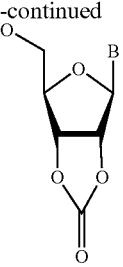

However, tertiary carbonates as shown by Losse and tertiary thiocarbonates as discovered in the present disclosure are resistant to formation of 2'-3' cyclic carbonates and are particularly useful as 2'-protection [Losse G, Suptitz G, Krusche, K, *Journal für Praktische Chemie*, 1992, 334(6), 531-532, which is incorporated herein by reference].

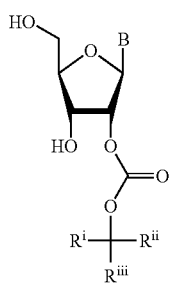
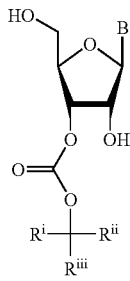
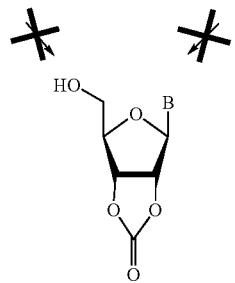

Carbonates are particularly useful since, even if the cyclic carbonate is formed at some percentage during the synthesis of the monomers, the cyclic carbonate does not produce a reactive monomer (3'-isomer) with the protecting group on the 3'-hydroxyl. This is especially important to ensure only formation of 5'-3'-linked RNA molecules. However, all tertiary carbonates are not useful for the synthesis of RNA molecules. Tertiary alkylcarbonates can be quite stable to nucleophiles and resistant to cleavage by peroxyanions. The tertiary butyloxycarbonyl group was previously described for the protection of the 2'-hydroxyl for solid-phase RNA synthesis. The resistance of this group to removal by a variety of mild pH conditions demonstrated the unsuitability of this group for RNA synthesis [Losse G, Naumann, W, Winkler, A, Suptitz G, Journal für *Praktische Chemie*, 1994, 336(3), 233-236, which is incorporated herein by reference]. In order to remove this protecting group the authors needed to employ a high concentration (4 molar) of hydrochloric acid in dioxane. It has also been demonstrated that this protecting group was quite stable to the mildly basic but highly nucleophillic conditions of peroxyanion cleavage using 2 molar hydrogen peroxide at pH 9.5. Therefore, it was found that the carbonate moiety should be modified to make the group more labile to nucleophiles and specifically to peroxyanion nucleophiles. This can be accomplished in at least two methods. The first is the addition of electron withdrawing groups to the alkyl or aryl substituents that can then affect the stability of the cleavage products formed as shown below.

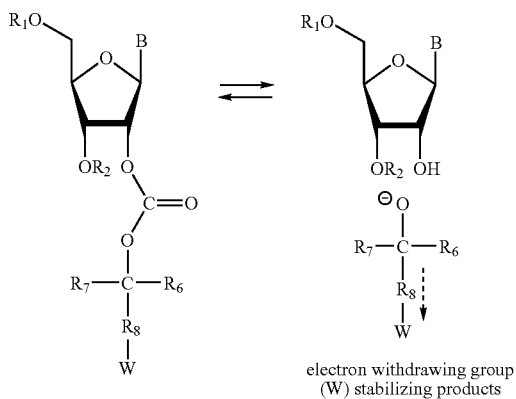

electron withdrawing group
(W) stabilizing products

An example of adding an electron-withdrawing group to a tertiary carbonate includes the example of using one or more trifluoromethyl groups to replace one or more of the methyl groups on the tertiary butyloxycarbonyl group as shown below.

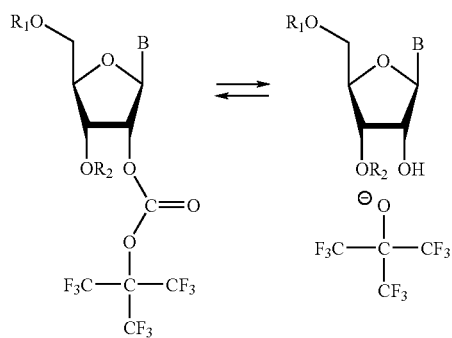

A particularly useful method of adding an electron-withdrawing group to a tertiary carbonate (see below) is to replace one or more of the methyl groups on the tertiary butyloxycarbonyl group with a substituted benzene ring and to have the benzene ring substituted with one or more electron withdrawing groups.

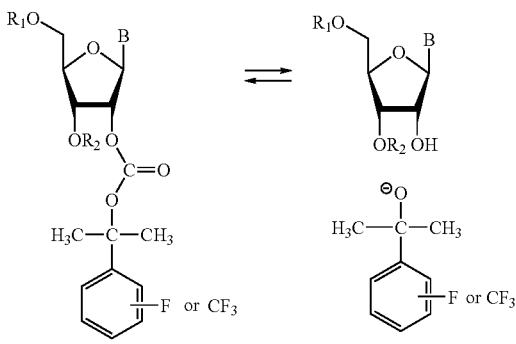

Electron-withdrawing groups can either exist as part of the protecting group prior to cleavage by peroxyanions, or be created by the deprotection reaction. A particularly useful approach illustrated below is to use substituents on the alkyl or aryl groups that are electron-donating and to have those substituents chemically converted to electron-withdrawing groups in the solution of peroxyanion. The electron donating effect helps stabilize the protecting group during the oligomerization process, and then this effect is reversed during cleavage of the protecting group to produce an electron-withdrawing group that stabilizes the products from the cleavage reaction and then aids the facile removal under mild pH conditions.

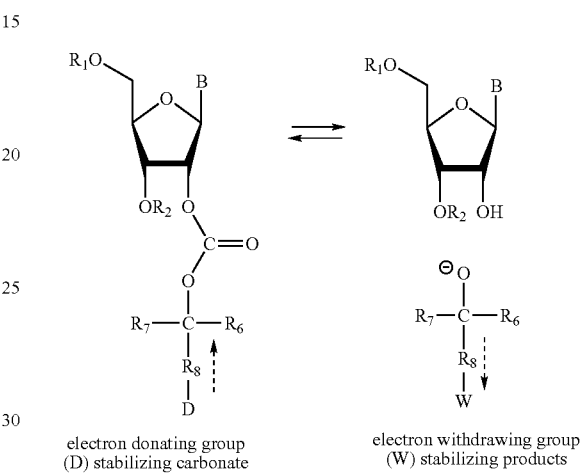

electron donating group (D) stabilizing carbonate    electron withdrawing group (W) stabilizing products An example of adding an electron-withdrawing group to a tertiary carbonate is the example of using one or more thiomethyl ethers to replace one or more of the methyl groups on the tertiary butyloxycarbonyl group. Thiomethylethers are typically stable to oxidation in the presence of the dilute iodine solutions that are used for oxidation of the phosphite triester to phosphate triester during the routine phosphoramidite DNA or RNA synthesis cycle. However, in the presence of dilute solutions of hydroperoxides, peracids, or combinations of hydroperoxides and peracids, the thiomethylether is rapidly oxidized to the corresponding sulfone (as shown below). The methyl sulfone is a strongly electron-withdrawing group that stabilizes the products from the cleavage reaction and then aids the facile removal of the under mild pH conditions.

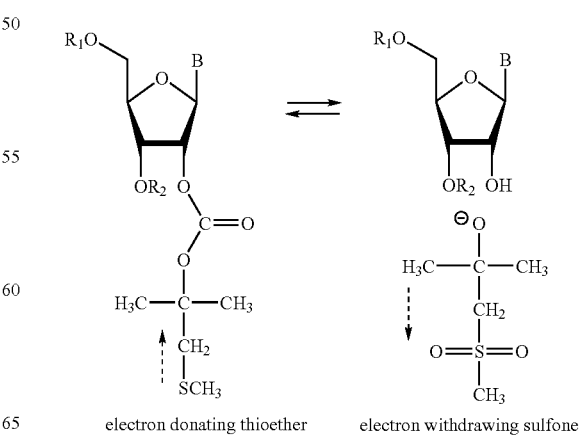

electron donating thioether    electron withdrawing sulfone

A particularly convenient method of adding a moiety to a tertiary carbonate that can then be chemically converted to an electron-withdrawing group by peroxyanions is the direct substitution of a sulfur atom for an oxygen atom in the bridging position to form a thiocarbonate (see below).

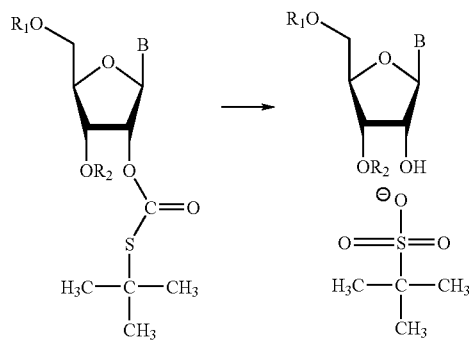

From data on the cleavage and oxidation of thiocarbonates, it appears that the sulfur is not oxidized prior to the cleavage. Tertiary butylthiocarbonyl protected nucleosides exposed to 1 to 2 molar solutions of hydrogen peroxide at pH 6.0 do not generate sulfur oxidation products or cleavage of the thiocarbonate group, even after a 24-hour exposure. However, if the pH is raised to 9.5, the cleavage of the thiocarbonate is group is complete in approximately 10 minutes. The data suggests that once the cleavage reaction occurs, using a nucleophillic solution of hydrogen peroxide, the resulting mercaptan is rapidly oxidized to the sulfonate, making the reaction rapid and irreversible.

The second method for making the group more labile to nucleophiles, and specifically to peroxyanion nucleophiles, is to incorporate a moiety or moieties that enhances removal of the protecting group by a fragmentation process that creates thermodynamically stabile fragments illustrated below. This stabilizes the products of the cleavage reaction promoting facile removal of protecting groups under mild pH conditions.

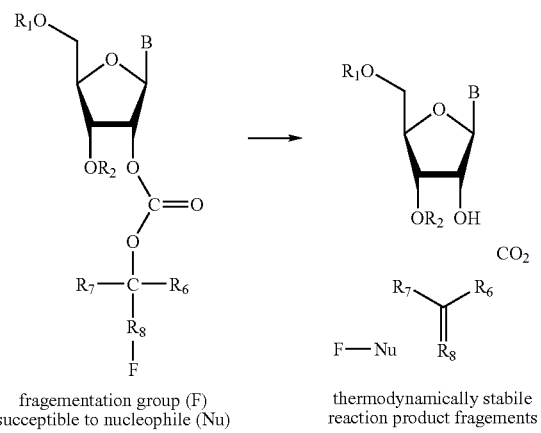

fragementation group (F) susceptible to nucleophile (Nu)

thermodynamically stabile reaction product fragements

Examples of such protecting groups are the tertiary carbonates of thiohemiacetals. Shown below is an example of 2'-hydroxyl protection using 2-thiomethylpropane-2-oxycarbonyl. Upon cleavage by peroxyanion nucleophiles the protecting group is fragmented into the highly thermodynamically stable products of acetone and methanesulfonate.

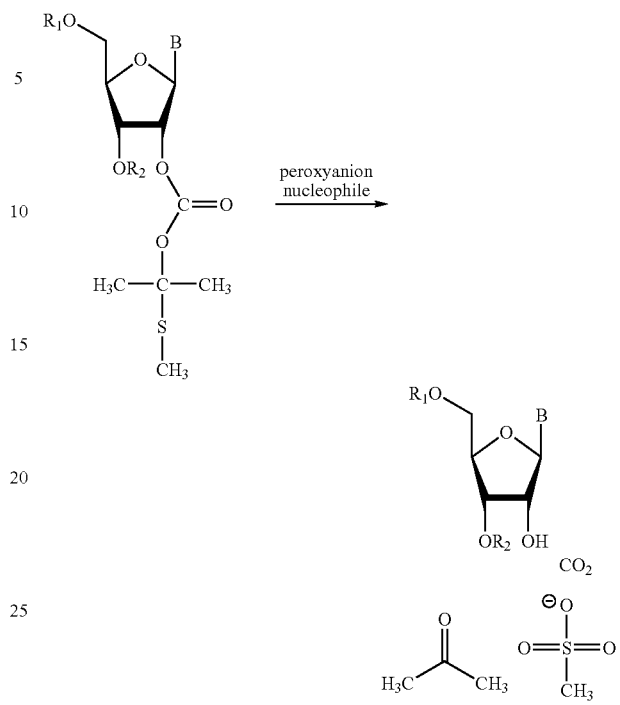

Oxidizable 2'-Hydorxyl Protecting Groups

Another embodiment includes nucleotide monomers and polynucleotides that include nucleotide moieties, where each of the nucleotide monomers and the nucleotide moieties include, but are not limited to, a protecting group (e.g., group I, group II, , group VI, group VIIa, group VIIb, group VIII,) that can undergo oxidative transformations to enhance the lability of the protecting group towards the nucleophilic removal. The oxidative transformation can occur prior to the cleavage, typically generating an electron withdrawing species on the protecting group that did not exist prior to the oxidation reaction or after the cleavage reaction to generate a species that cannot participate in an equilibrium reaction to reform the protecting group. An example of a species that undergoes an oxidative transformation to produce an electron withdrawing species that makes the protecting group more labile is the 2-methylthiobenzoyl group. The 2-methylthiobenzoyl group has similar stability to benzoyl or 2-methylbenzoyl. However, upon exposure to a buffered 6% hydrogen peroxide solution at pH 9.5, the 2-methylthio moiety is oxidized to a methylsulfone, and the methylsulfone derivative is significantly more labile to nucleophiles than benzoyl or 2-methylbenzoyl. The resulting 2-methylsulfonbenzoyl is cleaved rapidly by the hydroperoxide anion. An example of an oxidative transformation that occurs after the cleavage of the protecting group is the t-butylthiocarbonate. The sulfur atom on the t-butylthiocarbonate is not oxidized when exposed to 6% hydrogen peroxide at pH 5.0, and its lability towards nucleophile is similar to t-butylcarbonate. However, using 6% hydrogen peroxide at pH 9.5, rapidly generates the t-butylsulfonic acid and the removal of the protecting group is quite facile. This is in stark contrast to the use of t-butyl carbonate as a 2'-hydroxyl protecting group, which was shown to be convenient to introduce onto the 2'-hydroxyl of a nucleoside and resistant to the formation of the 2'-3'-cyclic carbonate. However difficult, if not impossible, to remove this protecting group without destroying the desired RNA products. The t-butyl carbonate was shown to be very resistant to nucleophiles and was removed using 5 molar solutions of hydrochloric acid.

The present disclosure includes polynucleotide (e.g., RNA) that include combinations of nucleotide moieties such as, but not limited to, compounds of structure I having one or more protecting groups as described herein, compounds of structure II having one or more protecting groups as described herein, nucleotide moities having one or more protecting groups as described herein, nucleotide moieties not including protecting groups, nucleotide ,moieties known in the art, combinations thereof, and the like.

In an embodiment, the present disclosure includes a polynucleotide compound having structure III:

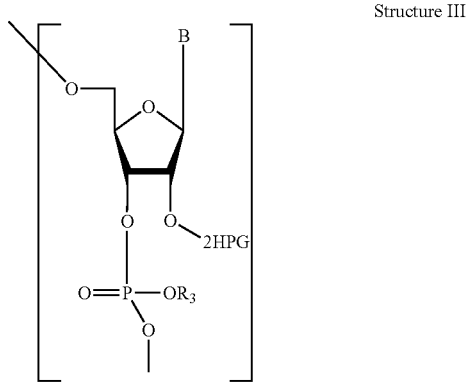

Structure III where B can be, but is not limited to, a base including a protection group; where $R_3$ can be a group such as, but not limited to, an alkyl group, an aryl group, a substituted alkyl, and a substituted aryl group; and where 2HPG is a 2'-hydroxyl protecting group selected from groups I through VIII. It should be noted that the structure above could be bonded to one or more nucleotide moieties and/or to a substrate.

In an embodiment, the present disclosure includes a polynucleotide compound having structure IV:

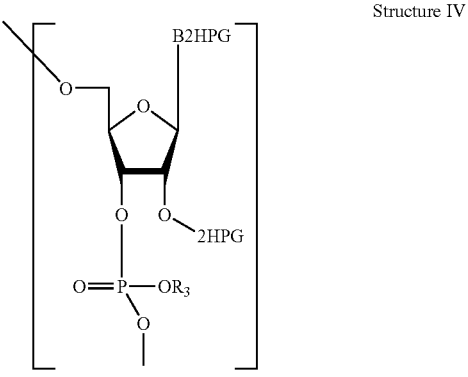

Structure IV where B can be, but is not limited to, a base and a base including protecting group, wherein each protecting group is selected from one of the following: an exocyclic amino protection group and an imino protecting group; where $R_3$ can be a group such as, but not limited to, an alkyl group, an aryl group, a substituted alkyl, a substituted aryl group; and where 2HPG is identical for both the 2'-hydroxyl protecting group and the heterobase exocyclic amino protected group selected from groups I through VIII. It should be noted that the structure above could be bonded to one or more nucleotide moieties and/or to a substrate.

Heterocyclic Base Protecting Groups

Embodiments of the disclosure include nucleotide monomers and polynucleotide compounds including at least one nucleotide moiety unit, where the nucleotide monomer and the nucleotide moiety each include a heterocyclic base protecting group. The nucleotide monomer and the nucleotide moiety are different, in at least one way, in that the nucleotide moiety is part of a polynucleotide compound, while the nucleotide monomer is not part of a polynucleotide compound. The nucleotide moiety includes a linking moiety that links a plurality of nucleotide moieties, while the nucleotide monomer does not include such a linking moiety. For the following discussion the structures may be referred to as "nucleotide monomer", but it is to be understood that the structures can be nucleotide moieties if a linking group is included in the structure to interconnect nucleotide moieties in a polynucleotide compound.

Exocyclic amines of the aglycone need to be protected during polynucleotide synthesis. Typically, the following exocyclic amines N-4 of cytidine, N-6 of adenosine and N-2 of guanosine require, protection during RNA synthesis. Sometimes, the imino group can require additional protection. In the case of imino protection, the N-3 or O-4 of uridine and the N-1 or O-6 of guanosine can require a protecting group. In most cases, the protecting groups utilized for exocyclic amines can also be applied to the protection of the imino group through a screening process.

Embodiments of the disclosure can include nucleotide monomers and polynucleotide compounds (e.g., ribonucleotide compounds) including nucleotide monomers and moieties having 2'-hydroxyl protecting groups as described herein as well as heterocyclic base protecting groups. The polynucleotide can include nucleotide monomers and moieties having structures XX through XXII. Embodiments of the position of the base protecting groups (APG) are shown on structures XX through XXIII:

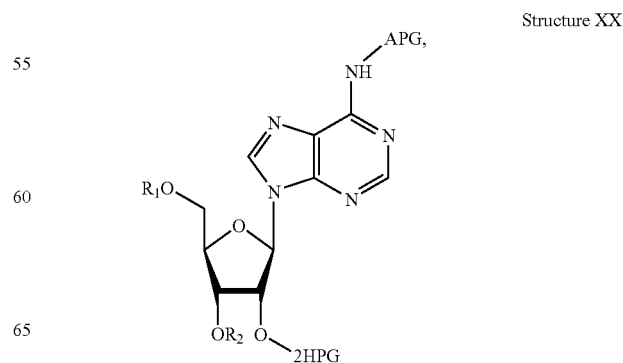

Structure XX

-continued

Structure XXI

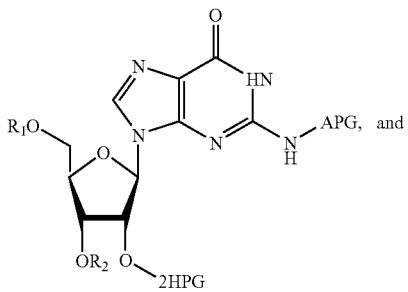

Structure XXII

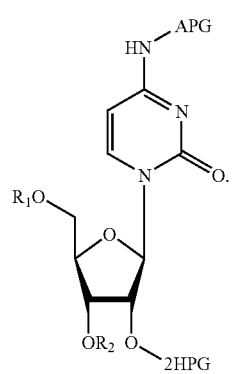

The APGs can include, but are not limited to, base protecting groups that are removed under a same set of conditions as the 2HPG (e.g., in peroxyanions solutions). For example, the APG and the 2HPG can be removed in a single step when exposed to a peroxyanion solution. For example, APG can be acetyl, chloroacetyl, dicholoracetyl, trichloroacetyl, fluoroacetyl, difluoroacetyl, trifluoroacetyl, nitroacetyl, propionyl, n-butyryl, i-butyryl, n-pentanoyl, i-pentanoyl, t-pentanoyl, phenoxyacteyl, 2-chlorophenoxyacetyl, t-butyl-phenoxyacetyl, methylthioacetyl, phenylthioacetyl, 2-chlorophenylthioacetyl, 3-chlorophenylthioacetyl, 4-chlorophenylthioacetyl, t-butyl-phenylthioacetyl, benzoyl, 2-nitrobenzoyl, 3-nitrobenzoyl, 4-nitrobenzoyl, 2-chlorobenzoyl, 3-chlorobenzoyl, 4-chlorobenzoyl, 2,4-di-chlorobenzoyl, 2-fluorobenzoyl, 3-fluorobenzoyl, 4-fluorobenzoyl, 2-trifluoromethylbenzoyl, 3-trifluoromethylbenzoyl, 4-trifluoromethylbenzoyl, benzyloxycarbonyl, and the like.

The APGs can include, but are not limited to, base protecting groups that are removed under a different set of conditions as the 2HPG. These groups that can not be removed by peroxyanion depend strongly on the base (A, G, or C) they are protecting. Most of the amidine protecting groups such as dimethylformamidine, dibutylformamidine, dimethylacetamidine, diethylacetamidine are stable to peroxyanions.

R1 and R2 are each individually selected from one of the following: H, a protecting group, and

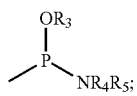

but R1 and R2 are both not:

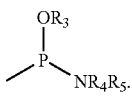

R1 and R2 can also be a linking moiety that interconnects a plurality of nucleotide moieties in a polynucleotide.

$R_3$ can include, but is not limited to, an alkyl group, a substituted alkyl group, an aryl group, and a substituted aryl group. $R_3$ can optionally be a linking moiety that links to another nucleotide moiety of a polynucleotide or connected to a substrate. $R_4$ and $R_5$ can each independently include, but are not limited to, an alkyl group, a substituted alkyl group, an aryl group, a substituted aryl group, a cyclic alkyl, a substituted cyclic alkyl, a heterocycle, a substituted heterocycle, an aryl group, and a substituted aryl group and, optionally a linking moiety that links to another nucleotide moiety of the polynucleotide or connected to a substrate.

X can include, but is not limited to, H, OH, halogen, an alkoxy group, a substituted alkoxy group, an aryloxy group, a substituted aryloxy group, an amino group, a substituted amino group, a cyano group, an azido group, a sulfonic acid group, a protecting group, and an O-protecting group.

The APGs can include, but are not limited to, exocyclic amino protecting groups. In addition, the APG can include, but are not limited to, base protecting groups that are removed under a same set of conditions as the 2'-hydroxyl protecting groups (e.g., in peroxyanions solutions). For example, the APG and the 2'-hydroxyl protecting groups can be removed in a single step when exposed to a peroxyanion solution.

In an embodiment, the APG is a moiety that can undergo oxidative transformations in peroxyanion solutions (as discussed in more detail below) to enhance the lability of the protecting group towards nucleophillic removal. These oxidative transformations can occur prior to the cleavage, typically generating an electron withdrawing species on the protecting group that did not exist prior to the oxidation reaction or after the cleavage reaction to generate a species that cannot participate in an equilibrium reaction to reform the protecting group.

The 2-methylthiobenzoyl group is an example of a species that undergoes an oxidative transformation to produce and electron withdrawing species that makes the protecting group more labile. The 2-methylthiobenzoyl group has similar stability to benzoyl or 2-methylbenzoyl. However, upon exposure to a buffered 6% hydrogen peroxide solution at about pH 9.5, the 2-methylthio moiety is oxidized to a methylsulfone, and the methylsulfone derivative is significantly more labile to nucleophiles than benzoyl or 2-methylbenzoyl. The resulting 2-methylsulfonbenzoyl is cleaved rapidly by the hydroperoxide anion.

The t-butylthiocarbamate group is an example of an oxidative transformation that occurs after the cleavage of the protecting group. The sulfur atom on the t-butylthiocarbamate is not oxidized when exposed to 6% hydrogen peroxide at pH 5.0, and the lability to nucleophile is similar to t-butylcarbamate. However, using 6% hydrogen peroxide at about pH 9.5 rapidly renders the t-butylsulfonic acid, and the removal of the protecting group quite facile.

It should also be noted that as for the protection of heterobase protecting groups, a particularly useful set of the 2'-hydroxyl protecting group includes a moiety that can undergo oxidative transformations in peroxyanion solutions to enhance the lability of the protecting group towards nucleophillic removal, or a moiety that can be cleaved in peroxyanion solutions thus be deprotected simultaneously with the heterobase protecting groups in one single step (one pot reaction). These 2'-hydroxyl protecting groups include, but are not limited to: an ester protecting group, a carbonate protecting group, a thiocarbonate protecting group, and a carbamate protecting group.

The APGs can include, but are not limited to, base protecting groups such as those having the following structures:

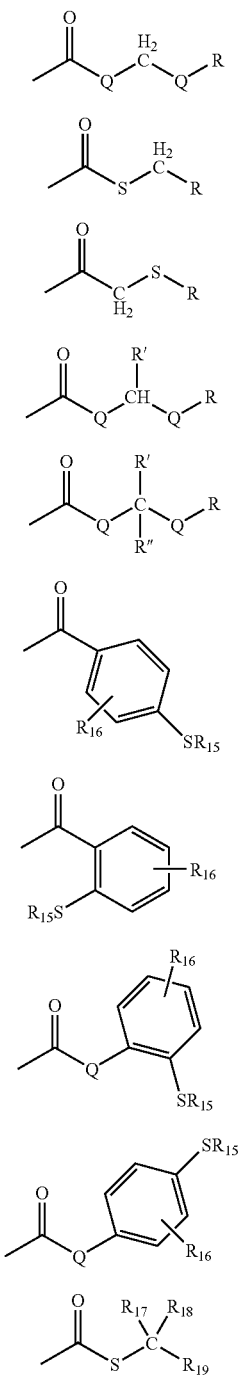

It should be noted that Q is an atom such as, but not limited to, sulfur (S) and oxygen (O), and that R is a group such as, but not limited to, an alkyl group, a substituted alkyl group, an aryl group, and a substituted aryl group. R' and R" are each independently selected from a group such as, but not limited to, a halogen, an alkyl group, a substituted alkyl group, an aryl group, and a substituted aryl group. $R_{15}$ is a group such as, but not limited to, an alkyl group, an aryl group, a substituted alkyl, and a substituted aryl group.

It should be noted that bonds (e.g., indicated by lines) that are directed into the center of a ring structure (e.g., benzene ring) mean that the bond can be to any one of the carbons of the ring that are only bonded to a hydrogen and another carbon of the ring. $R_{16}$ can include one or more groups, where each group is attached to one of the carbons in the carbon ring. Each $R_{16}$ is independently a group such as, but not limited to, H, a halogen, a hydroxyl group, an alkoxy group, a substituted alkoxy group, an aryloxy group, a substituted aryloxy group, an amino group, a substituted amino group, a nitro group, a nitrile group, an alkyl group, an aryl group, a substituted alkyl, and a substituted aryl group. In an embodiment, when there are more than one $R_{16}$ (e.g., multiple $R_{16}$'s bonded to different carbons on the carbon ring), then two or more of $R_{16}$ are optionally cyclically connected to each other. $R_{17}$, $R_{18}$, and $R_{19}$, are each independently a group such as, but not limited to, H, an alkyl group, an aryl group, a substituted alkyl, and a substituted aryl group. In an embodiment, two or three of $R_{17}$, $R_{18}$, and $R_{19}$ can be cyclically connected to each other.

In another embodiment, the nucleotide polymer can include, but is not limited to, a nucleotide polymer that includes at least one structure such as those shown in structures I through III above. Embodiments of the position of the base protecting groups (APG) on the bases are shown on structures XX through XXII above.

It should be noted that in this embodiment that R1 and R2 are each individually be selected from one of the following: H, a protecting group, and:

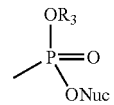

but where both R1 and R2 are not

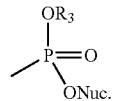

$R_3$ can include, but is not limited to, an alkyl group, a substituted alkyl group, an aryl group, a substituted aryl group, and, optionally, a linking moiety that links to another nucleotide moiety of a polynucleotide. Nuc is a nucleotide or polynucleotide.

The APGs can include, but are not limited to, base protecting groups that are removed under a different set of conditions than the 2'-hydroxyl protecting groups, for example wherein the 2'-hydroxyl protecting groups include, but are not limited to, TBDMS, TOM, ACE, acetals such as THP, and derivatives of acetals (Ctmp and the like).

In addition, the APGs can include, but are not limited to, base protecting groups such as acetyl, chloroacetyl, dicholoracetyl, trichloroacetyl, fluoroacetyl, difluoroacetyl, trifluoroacetyl, nitroacetyl, propionyl, n-butyryl, i-butyryl, n-pentanoyl, i-pentanoyl, t-pentanoyl, phenoxyacteyl, 2-chlorophenoxyacetyl, t-butyl-phenoxyacetyl, methylthioacetyl, phenylthioacetyl, 2-chlorophenylthioacetyl, 3-chlorophenylthioacetyl, 4-chlorophenylthioacetyl, t-butyl-phenylthioacetyl, benzyloxycarbonyl, (9-fluoroenyl)-methoxycarbonyl (Fmoc), 2-nitrophenylsulfenyl, 4-nitrophenylethylcarbonyl, 4-nitrophenylethoxycarbonyl, diphenylcarbamoyl, morpholinocarbamoyl, dialkylformamidines, succinyl, phthaloyl, benzoyl, 4-trifluoromethylbenzoyl, 2-methylbenzoyl, 3-methylbenzoyl, 4-methylbenzoyl, 2,4-dimethylbenzoyl, 2,6-dimethylbenzoyl, 2,4,6-trimethylbenzoyl, 2-methoxybenzoyl, 3-methoxybenzoyl, 4-methoxybenzoyl, 2,4-dimethoxybenzoyl, 2,6-dimethoxybenzoyl, 2,4,6-trimethoxybenzoyl, 2-methylthiobenzoyl, 3-methylthiobenzoyl, 4-methylthiobenzoyl, 2,4-dimethylthiobenzoyl, 2,6-dimethylthiobenzoyl, 2,4,6-trimethylthiobenzoyl, 2-chlorobenzoyl, 3-chlorobenzoyl, 4-chlorobenzoyl, 2,4-dichlorobenzoyl, 2,6-dicholorbenzoyl, 2-fluorobenzoyl, 3-fluorobenzoyl, 4-fluorobenzoyl, 2,4-difluorobenzoyl, 2,6-difluorobenzoyl, 2,5-difluorobenzoyl, 3,5-difluorobenzoyl, 2-trifluoromethylbenzoyl, 3-trifluoromethylbenzoyl, 2,4-trifluoromethylbenzoyl, 2,6-trifluoromethylbenzoyl, 2,5-trifluoromethylbenzoyl, 3,5-trifluoromethylbenzoyl, 2-nitrobenzoyl, 3-nitrobenzoyl, 4-nitrobenzoyl, (3-methoxy 4-phenoxy)benzoyl, (triphenyl)silylethyleneoxycarbonyl, (diphenylmethyl)silylethyleneoxycarbonyl, (phenyldimethyl)silylethyleneoxycarbonyl, (trimethyl)silylethyleneoxycarbonyl, (triphenyl)silyl(2,2-dimethyl)ethyleneoxycarbonyl, (diphenylmethyl)silyl[(2,2-dimethyl)ethylene]oxycarbonyl, phenyldimethylsilyl[(2,2-dimethyl)ethylene]oxycarbonyl, trimethylsilyl[(2,2-dimethyl)ethylene]oxycarbonyl, methyloxycarbonyl, ethyloxycarbonyl, propyloxycarbonyl, isopropyloxycarbonyl, butyloxycarbonyl, isobutyloxycarbonyl, t-butyloxycarbonyl, phenyloxycarbonyl, benzyloxycarbonyl, methylthiocarbonyl, ethylthiocarbonyl, propylthiocarbonyl, isopropylthiocarbonyl, butylthiocarbonyl, isobutylthiocarbonyl, t-butylthiocarbonyl, phenylthiocarbonyl, benzylthiocarbonyl, methyloxymethyleneoxycarbonyl, methylthiomethylene-oxycarbonyl, phenyloxymethylene-oxycarbonyl, phenylthiomethyleneoxycarbonyl, methyloxy(methyl)methyleneoxycarbonyl, methylthio(methyl)methyleneoxycarbonyl, methyloxy(dimethyl)methyleneoxycarbonyl, methylthio(dimethyl)methyleneoxycarbonyl, phenyloxy(methyl)methyleneoxycarbonyl, phenylthio(methyl)methyleneoxycarbonyl, phenyloxy(dimethyl)methyleneoxycarbonyl, phenylthio(dimethyl)methyleneoxycarbonyl, and substituted derivatives of any of these previously described groups.

It should also be noted that as for the protection of the 2'-hydroxyl group, a particularly useful set of heterobase protecting groups is a moiety that can undergo oxidative transformations in peroxyanion solutions (as discussed in more detail below) to enhance the lability of the protecting group towards nucleophilic removal. These oxidative transformations can occur prior to the cleavage, typically generating an electron withdrawing species on the protecting group that did not exist prior to the oxidation reaction or after the cleavage reaction to generate a species that cannot participate in an equilibrium reaction to reform the protecting group. An example of a species that undergoes an oxidative transformation to produce an electron withdrawing species that makes the protecting group more labile is the 2-methylthiobenzoyl group. The 2-methylthiobenzoyl group has similar stability to benzoyl or 2-methylbenzoyl. However, upon exposure to a buffered 6% hydrogen peroxide solution at pH 9.5, the 2-methylthio moiety is oxidized to a methylsulfone, and the methylsulfone derivative is significantly more labile to nucleophiles than benzoyl or 2-methylbenzoyl. The resulting 2-methylsulfonbenzoyl is cleaved rapidly by the hydroperoxide anion. An example of an oxidative transformation that occurs after the cleavage of the protecting group is the t-butylthiocarbamate. The sulfur atom on the t-butylthiocarbamate is not oxidized when exposed to 6% hydrogen peroxide at pH 5.0, and the lability to nucleophiles is similar to t-butylcarbamate. However using 6% hydrogen peroxide at a pH of about 9.5, rapidly generates the t-butylsulfonic acid and the removal of the protecting group is quite facile.

In another embodiment, R1 and R2 can have the following structure:

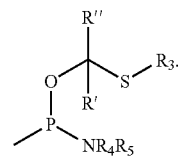

R' and R" are each individually a group such as, but not limited to, H, an alkyl group, an aryl group, a substituted alkyl, and a substituted aryl group. In an embodiment, R' and/or R" can include a linking moiety that interconnects the nucleotide moieties in a polynucleotide or connected to a substrate.

$R_3$ is a group such as, but not limited to, an alkyl group, an aryl group, a substituted alkyl, and a substituted aryl group. In an embodiment, R3 can include a linking moiety that interconnects the nucleotide moieties in a polynucleotide or connected to a substrate.

$R_4$ and $R_5$ are each independently a group such as, but not limited to, an alkyl group, an aryl group, a substituted alkyl, and a substituted aryl group. In addition, $R_4$ and $R_5$ can be, optionally, cyclically connected to each other. In an embodiment, $R_4$ and/or $R_5$ can include a linking moiety that interconnects the nucleotide moieties in a polynucleotide or connected to a substrate.

In an embodiment, the APGs can include, but are not limited to, base protecting groups that are removed under a same set of conditions as the 2HPG (e.g., in peroxyanions solutions). For example, the APG and the 2HPG can be removed in a single step when exposed to a peroxyanion solution. For example, APG can be acetyl, chloroacetyl, dicholoracetyl, trichloroacetyl, fluoroacetyl, difluoroacetyl, trifluoroacetyl, nitroacetyl, propionyl, n-butyryl, i-butyryl, n-pentanoyl, i-pentanoyl, t-pentanoyl, phenoxyacteyl, 2-chlorophenoxyacetyl, t-butyl-phenoxyacetyl, methylthioacetyl, phenylthioacetyl, 2-chlorophenylthioacetyl, 3-chlorophenylthioacetyl, 4-chlorophenylthioacetyl, t-butyl-phenylthioacetyl, benzoyl, 2-nitrobenzoyl, 3-nitrobenzoyl, 4-nitrobenzoyl, 2-chlorobenzoyl, 3-chlorobenzoyl, 4-chlorobenzoyl, 2,4-di-chlorobenzoyl, 2-fluorobenzoyl, 3-fluorobenzoyl, 4-fluorobenzoyl, 2-trifluoromethylbenzoyl, 3-trifluoromethylbenzoyl, 4-trifluoromethylbenzoyl, benzyloxycarbonyl and the like.

In an embodiment, the APGs can include, but are not limited to, base protecting groups that are removed under a different set of conditions as the 2HPG. These groups that can not be removed by peroxyanion depend strongly on the base (A, G or C) they are protecting. Most of the amidine protecting groups such as dimethylformamidine, dibutylformamidine, dimethylacetamidine, diethylacetamidine are stable to peroxyanions.

Deprotecting

As mentioned above, embodiments of the present disclosure include methods for deprotecting one or more protecting groups of a polynucleotide (e.g., a RNA) molecule such as those described herein. In particular, the methods include deprotecting a RNA molecule in a solution of an α-effect nucleophile (e.g., a peroxyanion solution), where the α-effect nucleophile has a pKa of about 4 to 13. In addition, the solution is at a pH of about 6 to 11.

One advantage of using a mildly basic solution including an α-effect nucleophile is that the solution including an α-effect nucleophile is compatible with standard phosphoramidite methods for polynucleotide synthesis. Further, the deprotected RNA molecules are stable and show little or no degradation for an extended period of time when stored in the solution including the a-effect nucleophile. An additional advantage of using the solution including an α-effect nucleophile is that the disadvantages associated with the 3- and 2-step processes typically used for RNA deprotecting are not present.

It should be noted that embodiments of the present disclosure include methods that are multi-step methods and use the α-effect nucleophile (e.g., for deprotection of the one or more 2'-hydroxyl protecting groups, one or more base protecting groups, and/or one or more phosphorus protecting groups) may be one of a number of steps used in the synthesis and/or deprotection of the polynucleotide. For example, one step of the method may use the α-effect nucleophile to deprotect one or more protecting groups, while one or more other steps may include other solutions (e.g., TBDMS, TOM, ACE, and like chemistries) used to deprotect one or more other protecting groups.

In general, the methods involve forming and/or providing a synthetic RNA molecule, where the RNA molecule has at least one of the following: a base having a protecting group, a 2'-hydroxyl protecting group, a phosphorus protecting group, and combinations thereof. Then, the RNA molecule is mixed with a solution including a least one type of an α-effect nucleophile, where the solution is at a pH of about 4 to 11. In addition, the α-effect nucleophile has a pKa of about 4 to 12. One or more of the protecting groups can be deprotected through interaction with the α-effect nucleophile.

In general, these solutions including the α-effect nucleophiles can be predominately buffered aqueous solutions or buffered aqueous/organic solutions. Under these conditions it is convenient and cost effective to remove the deprotecting solutions by simple precipitation of the desired RNA oligonucleotides directly from the deprotecting mixture by addition of ethanol to the solution. Under these conditions, the RNA is pelleted to the bottom of a centrifuge tube and the deprotecting mixture containing the α-effect nucleophile is removed by simply pouring off the supernatant and rinsing the pellet with fresh ethanol. The desired RNA is then isolated by resuspending in a typical buffer for chromatographic purification or direct usage in the biological experiment of interest. Because of the nature of most α-effect nucleophiles, removal of the deprotection reagents from the desired RNA products is significantly less tedious and time consuming; this is especially true in comparison to the use of a fluoride-ion solution for final deprotection of the RNA molecule.

One significant advantage for post synthetic deprotection applied to any method of RNA synthesis is that the α-effect nucleophile solution can be exploited to remove a variety of commonly used protecting groups, the protecting groups described herein, or linkers under pH conditions that do not catalyze rapid degradation of RNA. Unlike the commonly applied use of strong bases and/or typical nucleophiles for post synthetic deprotection of RNA, partial loss of the 2'-protecting group, prior to or during exposure to the α-effect nucleophiles, does not result in cleavage of the internucleotide bond. Therefore, the use of the α-effect nucleophile solutions simply for the deprotection of heterobase blocking groups has significant advantages over current methods even if coupled with the use of routine protecting groups. These advantages become even more significant if they are used with protecting groups described herein that are specifically optimized for the rapid removal under oxidative, nucleophilic conditions at neutral to mildly basic pH.

The solution of an α-effect nucleophile typically may have a pH in the range of about 4 to 11, about 5 to 11, about 6 to 11, about 7 to 11, about 8 to 11, about 4 to 10, about 5 to 10, about 6 to 10, about 7 to 10, or about 8 to 10. In particular embodiments, the solution has a pH of about 7 to 10. It should also be noted that the pH is dependent, at least in part, upon the α-effect nucleophile in the solution and the protecting groups of the RNA. Appropriate adjustments to the pH can be made to the solution to accommodate the α-effect nucleophile.

The α-effect nucleophiles can include, but are not limited to, peroxyanions, hydroxylamine derivatives, hydroximic acid and derivatives thererof, hydroxamic acid and derivatives thereof, hydrazine and derivatives thereof, carbazide and derivatives thereof, semicarbazides and derivatives thereof, and combinations thereof. The peroxyanion α-effect nucleophiles can include compounds such as, but not limited to, hydrogen peroxide and salts thereof, peracids and salts thereof, perboric acids and salts thereof, alkylperoxides and salts thereof, hydroperoxides and salts thereof, butylhydroperoxide and salts thereof, benzylhydroperoxide and salts thereof, phenylhydroperoxide and salts thereof, performic acid and salts thereof, peracetic acid and salts thereof, perbenzoic acid and salts thereof, chloroperbenzoic acid and salts thereof, benzoic acids and salts thereof, substituted perbenzoic acids and salts thereof, cumene hydroperoxide and salts thereof, perbutric acid and salts thereof, tertriarylbutylperoxybenzoic acid and salts thereof, decanediperoxoic acid and salts thereof, and combinations thereof.

Hydrogen peroxide, salts of hydrogen peroxide, and mixtures of hydrogen peroxide and performic acid are especially useful. Hydrogen peroxide, which has a pKa around 11, is particularly useful for deprotecting solutions above pH 9.0. Below pH 9.0 there is generally no sufficient concentration of peroxyanion to work as an effective nucleophile. Below pH 9.0 it is especially useful to use mixtures of hydrogen peroxide and peracids. These peracids can be preformed and added to the solution or they can be formed in situ by the reaction of hydrogen peroxide and the carboxylic acid or carboxylic acid salt.

An example is that an equal molar mixture of hydrogen peroxide and sodium formate can be used at pH conditions below 9.0 as an effective peroxyanion deprotecting solution where hydrogen peroxide alone is not an effective deprotecting mixture. The utility of peracids tends to be dependent upon the pKa of the acid and size of molecule: the higher the pKa of the acid, the more useful as a peroxyanion solution, and the larger the size of the molecule, the less useful. Typically the pKa of the peracid is lower than the pH of the desired peroxyanion solution.

The α-effect nucleophiles typically used in these reactions are typically strong oxidants, therefore the concentration of the reagent in the deprotecting solution should be limited in order to avoid oxidative side products where undesired. The α-effect nucleophiles are typically less than about 30% weight/vol of the solution, more typically between about 0.1% and 10% weight/vol of the solution and most typically about 3% to 7% weight/vol of the solution. The typical 3% solution of hydrogen peroxide is about 1 molar hydrogen peroxide. A solution of between 1 molar and 2 molar hydrogen peroxide is especially useful. A typical solution of hydrogen peroxide and performic acid is an equal molar mixture of hydrogen peroxide and performic acid, both in the range of about 1 to 2 molar. An example of an in situ prepared solution of performic acid is about 2 molar hydrogen peroxide and about 2 molar sodium formate buffered at about pH 8.5.

In typical embodiments, the α-effect nucleophile is characterized as having a pKa in the range from about 4 to 13, about 4 to 12, about 4 to 11, about 5 to 13, about 5 to 12, about 5 to 11, about 6 to 13, about 6 to 12, about 6 to 11, about 7 to 13, about 7 to 12, or about 7 to 11.

It should also be noted that the pKa is a physical constant that is characteristic of the specific α-effect nucleophile. Chemical substitution and solvolysis conditions can be used to raise or lower the pKa and therefore specifically optimize the conditions of deprotecting. Appropriate selection of the α-effect nucleophile should be made considering the other conditions of the method and the protecting groups of the RNA. In addition, mixtures of peroxides and hydroperoxides can be used with molecules to form peroxyanions in situ.

As an example a solution of hydrogen peroxide can be used with a solution of formic acid at pH conditions below 9.0. At pH conditions less than 9.0, hydrogen peroxide is not significantly ionized due to its ionization constant of around 11. At pH 7.0, only about 0.01% of the hydrogen peroxide is in the ionized form of the α-effect nucleophile. However, the hydrogen peroxide can react in situ with the formic acid to form performic acid in a stable equilibrium. At pH 7.0, the performic acid is significantly in the ionized form and is an active α-effect nucleophile. In general, the lower the pKa, the more ionized; the higher the pKa, the better the nucleophile. The advantage of such an approach is that solutions of performic acid tend to degrade rapidly and stabilizers need to be added. The equilibrium that is formed between the hydrogen peroxide solutions and the formic acid helps stabilize the performic acid such that it can be used to completely deprotect the RNA prior to degrading. Performic acid is especially useful in a buffered mixture of hydrogen peroxide at pH 8.5 because the pKa of performic acid is approximately 7.1. Peracetic acid is useful at pH 8.5 but less useful than performic acid because the pKa of peracetic acid is approximately 8.2. At pH 8.5, peracetic acid is only about 50% anionic, whereas at pH 8.5 performic acid is more than 90% anionic.

In general, the pKa for the hydroperoxides is about 8 to 13. The pKa for hydrogen peroxide is quoted to be about 10 to 12, depending upon the method of analysis and solvent conditions. The pKa for the alkylperoxides is about 8 to 14. The pKa for the peracids is about 3 to 9. In embodiments where the peroxyanion is hydroperoxide, the solution is at pH of about 9 to 11. In embodiments where the peroxyanion is hydrogen peroxide, the solution is at pH of about 9 to 10.

In embodiments where the peroxyanion is an alkylperoxide, the solution is at pH of about 8 to 11. In embodiments where the peroxyanion is a peracid, the solution is at pH of about 6 to 9. In addition, the peracid has a pKa of about 4 to 10.

In addition, the aqueous buffer solution includes a buffer such as, but not limited to, tris(hydroxymethyl)aminomethane, aminomethylpropanol, citric acid, N,N'-bis(2-hydroxyethyl)glycine, 2-[bis(2-hydroxyethyl)amino]-2-(hydroxy-methyl)-1,3-propanediol, 2-(cyclohexylamino)ethane-2-sulfonic acid, N-2-hydroxyethyl)piperazine-N'-2-ethane sulfonic acid, N-(2-hydroxyethyl)piperazine-N'-3-propane sulfonic acid, morpholinoethane sulfonic acid, morpholinopropane sulfonic acid, piperazine-N,N'-bis(2-ethane sulfonic acid), N-tris(hydroxymethyl)methyl-3-aminopropane sulfonic acid, N-tris(hydroxymethyl)methyl-2-aminoethane sulfonic acid, N-tris(hydroxymethyl) methylglycine, and combinations thereof.

Substrates for Solid Phase Synthesis

The polynucleotides (one or more units) can be attached to suitable substrates that may have a variety of forms and compositions. The substrates may derive from naturally occurring materials, naturally occurring materials that have been synthetically modified, or synthetic materials. Examples of suitable support materials include, but are not limited to, nitrocellulose, glasses, silicas, teflons, and metals (e.g., gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

One advantage of using α-effect nucleophiles is that unlike methods using fluoride-based solutions for the final deprotection of RNA, the α-effect nucleophiles are compatible with either polymeric or silica substrates. In this regard, silica substrates can be used since they are less expensive than polymeric substrates.

In contrast, fluoride ion final deprotection conditions attack the silica substrate in a similar manner as attacks the silicon protecting groups it is attempting to remove. As a result, the silica substrate can be dissolved or partially dissolved, giving a significant amount of fluorosilicate impurities that are difficult to remove. Also, the attack on the substrate decreases the effective concentration of the fluoride reagent used for deprotection, requiring longer deprotection times and higher concentrations of fluoride reagent. As a result, the use of fluoride ion final deprotection is often limited to the use of polymeric supports or multiple step final deprotections.

While the foregoing embodiments have been set forth in considerable detail for the purpose of making a complete disclosure, it will be apparent to those of skill in the art that numerous changes may be made to such details without departing from the spirit and the principles of the disclosure. Accordingly, the disclosure should be limited only by the following claims.

All patents, patent applications, and publications mentioned herein are hereby incorporated by reference in their entireties.

EXAMPLES

FIGS. 2A through 2E illustrate chromatographs of a synthetic RNA (SEQ. ID NO. 1, 5' GUCACCAGCCCACUUGAG 3') and a solution of 5% hydrogen peroxide in a solution having a pH of about 8 at various times (FIG. 2A (time$_{RNA}$=0), FIG. 2B (time$_{HP}$=0), FIG. 2C (time=3 hours), FIG. 2D (time=12 hours), and FIG. 2E (time=24 hours)).

The synthetic RNA showed little or no degradation in a solution of 5% hydrogen peroxide in a solution having a pH of about 8 for up to 24 hours.

General Examples

Transient Protection of Hydroxyl Moieties

Figure 3:
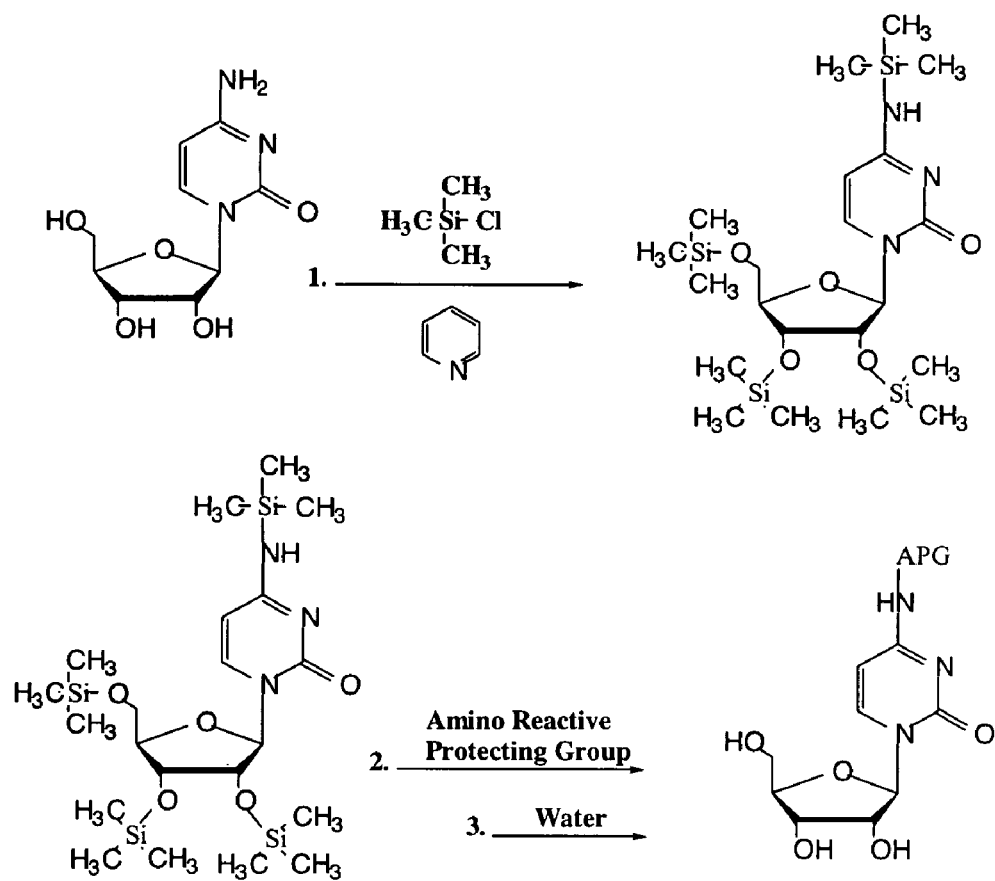
FIG. 3 illustrates the transient protection of hydroxyl moieties ("Jones Procedure").

The chemical protection of the exocyclic amino groups on the heterobases of DNA and RNA are typically accomplished using the "Jones procedures" (FIG. 3) that were initially described by Ti et. al. J. Am. Chem Soc 1982, 104, 1316-1319, which was incorporated herein by reference. In this procedure a nucleoside was transiently protected using excess trimethylsilyl chloride in pyridine. The trimethylsilyl groups react with all available hydroxyls and amines on the molecule. The trimethylsilyl group blocks the reaction of the hydroxyls with any further protecting groups, but the exocyclic amine remains reactive even though they can contain trimethylsilyl groups. This procedure can be adapted and optimized by anyone skilled in the art to a variety of substrates. For example, a larger excess of trimethylsilyl chloride was useful for obtaining higher yields on guanosine nucleosides (Fan el. al., Org. Lett. Vol 6. No. 15, 2004). If the nucleoside substrate already contains protective groups on one or more of the hydroxyl residues, the excess of trimethylsilyl chloride was scaled back. This procedure can also be used for protection of the imino groups on guanosine, thymidine and uridine.

Once the nucleoside has been transiently protected with trimethylsilyl groups, the exocyclic amine groups can be reacted with any number of amino reactive protecting groups. Examples of these, for illustration not exclusion, are acid chlorides, active esters such as p-nitrophenyl ester, chloroformates, thiochloroformates, acid anhydrides, pyrocarbonates, dithiopyrocarbonates, and the like.

Transient Protection of 5' and 3' Hydroxyl Moieties For Regioselective Protection of the 2'-Hydroxyl.

Figure 4:
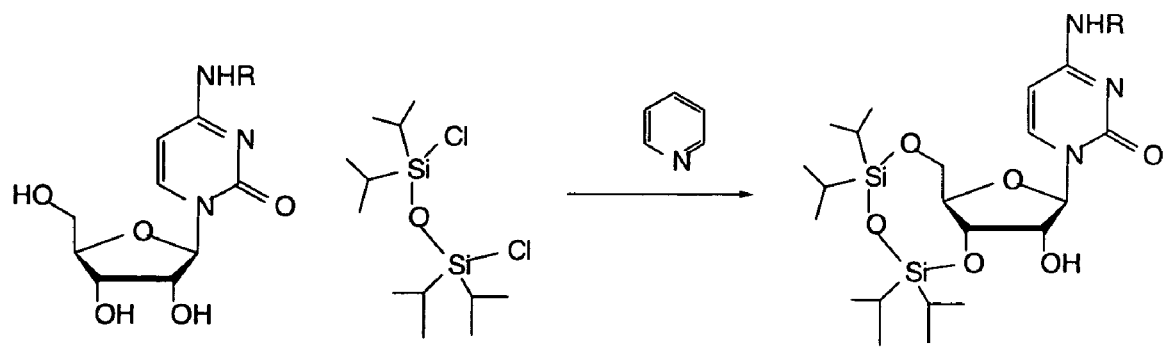
FIG. 4 illustrates the transient protection of hydroxyl moieties ("Markiewicz Procedure").

The chemical protection of the 5' and 3' hydroxyl moiety of a nucleoside was typically accomplished using a disiloxane deravitive known as tetraisopropyldisiloxane dichloride (TIPS). This protecting group simultaneously blocks the 5' and 3' hydroxyls to allow for complete regioselective introduction of a protective group on to the 2'-hydroxyl (FIG. 4) [Markiewicz, W. T., J. Chem Research (S) 1979 24-25) which was incorporated herein by reference].

Preparation of Novel Chloroformates as Amino and Hydroxyl Reactive Protecting Groups The preparation chloroformates includes using solutions of phosgene. Alcohols and mercaptans are typically reacted with excess phosgene at dry ice temperatures. It was often important to add one equivalent of a non-nucleophillic base, like pyridine or triethyl amine, to both catalyze the reaction and neutralize the HCl formed. The order of addition should be considered since, during the reaction, it was significant that the phosgene was generally in high concentration relative to the alcohol or mercaptan; this prevents the formation of carbonates or thiocarbonates. The phosgene solution (6 molar equivalents) was typically cooled on a dry ice/ethanol bath, and an alcohol or mercaptan solution in toluene/pyridine was added dropwise. The solution was allowed to warm to room temperature and was filtered under a blanket of dry argon gas. The resulting clear solution was evaporated to an oil using a rotary evaporator attached to a Teflon head diaphragm pump. The excess phosgene can be removed by evaporation, since phosgene was a gas at room temperature. The evaporation process removes the solvent and excess phosgene. The exhaust from the pump was bubbled through an aqueous solution of KOH to neutralize the excess phosgene. The temperature was controlled during the evaporation since some chloroformates can have low boiling points. Tertiary chloroformates are typically made using metal salts of alcohols and mercaptans. In this case, the metal salt, such as sodium salt, was formed on the alcohol or mercaptan prior to reacting with phosgene, and typically a non-nucleophilic base was not required.

Figure 5:
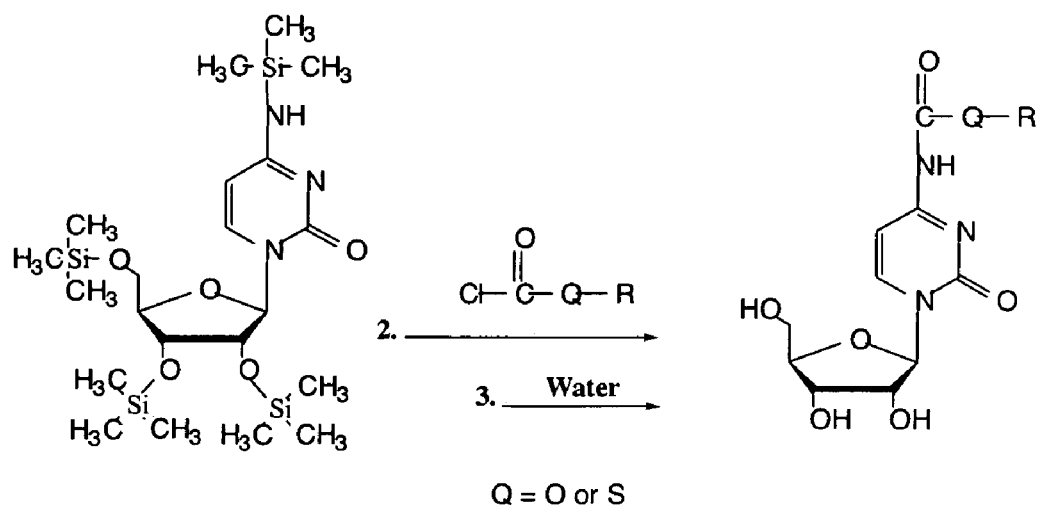
FIG. 5 illustrates the selective protection of exocyclic amine with chloroformate reagents.
Figure 6:
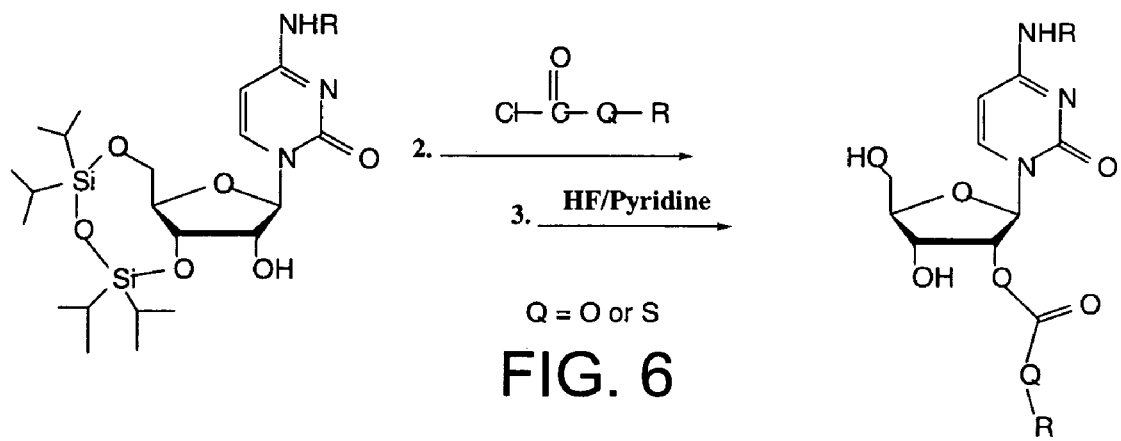
FIG. 6 illustrates the selective protection of 2'-hydroxyl with chloroformate reagents.

FIG. 5 illustrates the selective protection of exocyclic amine with chloroformate reagents. FIG. 6 illustrates the selective protection of 2'-hydroxyl with chloroformate reagents.

Simultaneous Protection of Amino and Hydroxyl Moieties with Novel Protecting Groups Nucleosides can be protected using the Markiewicz procedure to give 5',3'-O-(Tetraisopropyldisiloxane-1,3-diyl) ribonucleosides. Those monomers can then be reacted with either chloroformates or pyrocarbonates to produce ribonucleosides simultaneously protected with the same protecting group. This procedure has the specific advantage of streamlining the synthesis of nucleoside monomers for RNA synthesis and thus reducing the cost and complexity of synthesis. The ability to utilize the same protecting group on both the heterobase and 2'-hydroxyl was specifically enabled through the use of peroxyanions for the final deprotection. Peroxyanion nucleophillic cleavage at mildly basic pH allows for the deprotection of both groups under pH conditions that does not give rise to cyclization and cleavage of the intemucleotide bond. If typical nucleophiles were used to simultaneously remove the protective groups from the exocyclic amine and 2'-hydroxyl it would require that the reactions occur under strongly basic conditions. Under the strongly basic conditions of typical nucleophiles, removal of the 2'-hydroxyl protective group would immediately result in cyclization and cleavage of the internucleotide bond.

Figure 7:
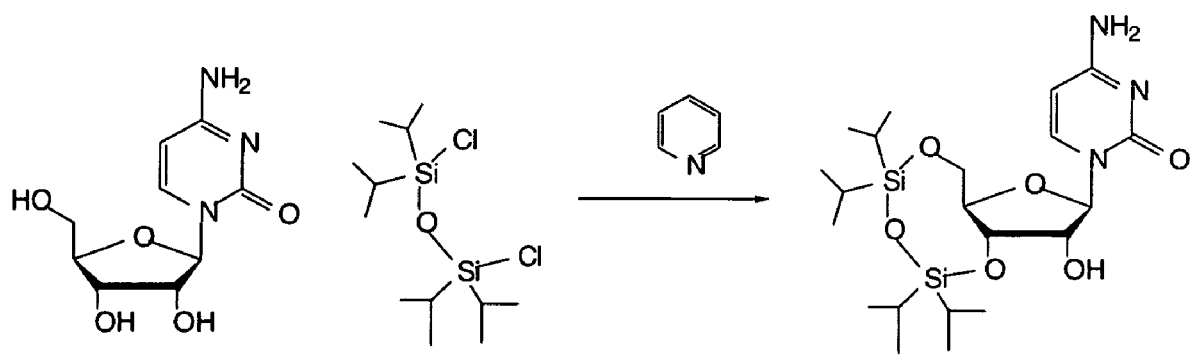
FIG. 7 illustrates the preparation of 5',3'-O-(tetraisopropyldisiloxane-1,3-diyl) ribonucleosides.
Figure 8:
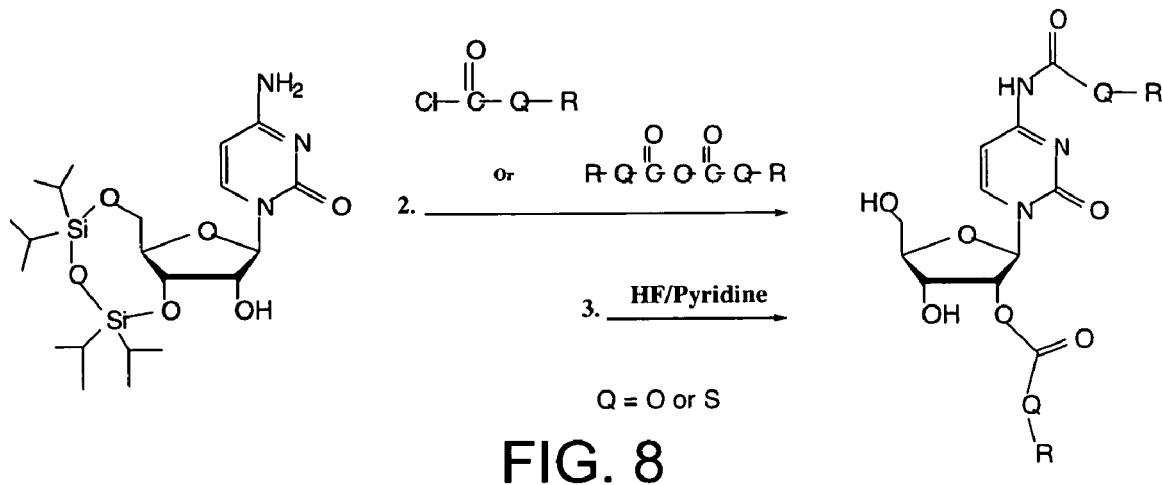
FIG. 8 illustrates the simultaneous protection of 5',3'-O-(tetraisopropyldisiloxane-1,3-diyl) ribonucleosides using chloroformates or pyrocarbonates.

FIG. 7 illustrates the preparation of 5',3'-O-(tTetraisopropyldisiloxane-1,3-diyl) ribonucleosides. FIG. 8 illustrates the simultaneous protection of 5',3'-O-(tetraisopropyldisiloxane-1,3-diyl) ribonucleosides using chloroformates or pyrocarbonates.

Preparation of Pyrocarbonates as Amino and Hydroxyl Reactive Protecting Groups

Many tertiary chloroformates are only stable at low temperatures. However, most tertiary thiochloroformates are stable at room temperature. The instability of tertiary chloroformates at room temperature makes it difficult to isolate and use these reagents. As a result, pyrocarbonates were selected for use in the preparation of nucleoside N-carbonyloxy compounds that have a tertiary carbon attached to the oxygen. These pyrocarbonates are significantly more stable at room temperature than the corresponding chloroformates. Pyrocarbonates are typically made using the metal salt or trimethylsilyl derivatives of tertiary alcohols. The metal salt of the alcohol was reacted in a non-polar solvent, such as hexanes with carbon dioxide, to form the corresponding carbonic acid. One half of one equivalent of methane sulfonyl chloride was added to the reaction to form the pyrocarbonate. The reaction was then quenched with a 5% aqueous solution of sulfuric acid and the pyrocarbonate isolated by evaporation of the hexanes layer.

Figure 9:
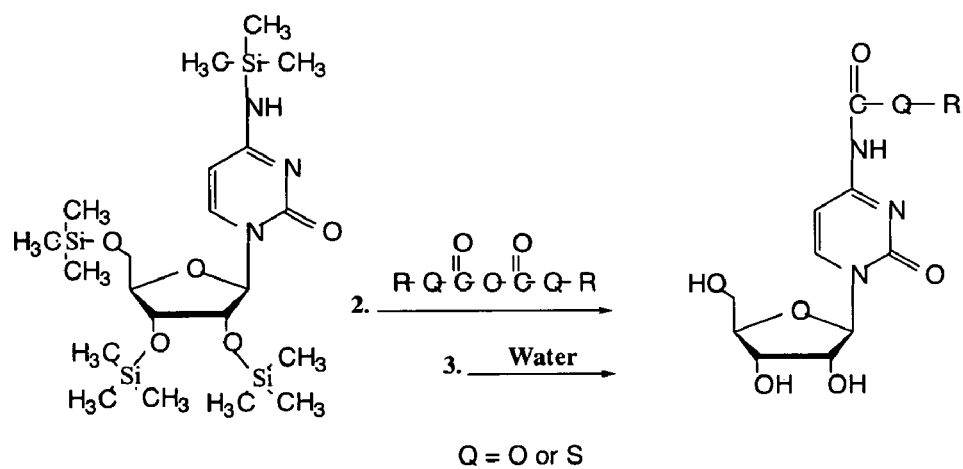
FIG. 9 illustrates the selective protection of exocyclic amine with pyrocarbonate reagents.
Figure 10:
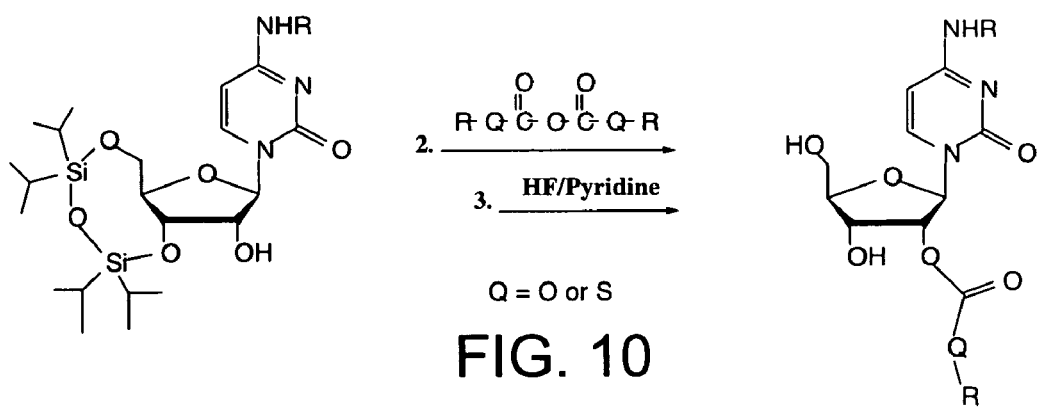
FIG. 10 illustrates the selective protection of 2'-hydroxyl with pyrocarbonate reagents.

FIG. 9 illustrates the selective protection of exocyclic amine with pyrocarbonate reagents. FIG. 10 illustrates the selective protection of 2'-hydroxyl with pyrocarbonate reagents.

General Procedure for the Synthesis of O-Trimethylsilylhemimethylthioacetals as Intermediate in the Prepration of Chloroformate Amino Reactive Protecting Groups (Group IV)

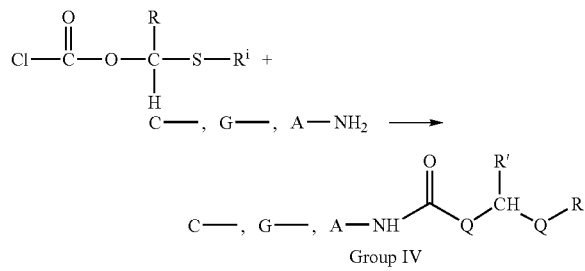

Preparation of KCN-18-Crown-6 Complex

The potassium cyanide-18-crown-6 complex was prepared by the dissolution of 1 equivalent of potassium cyanide in anhydrous methanol of 1 equivalent of 18-crown-6 (Aldrich). The solvent was removed at 65° C. using a Teflon head diaphragm pump, followed by drying under high vacuum at room temperature for 15 to 20 min.

A dry, round bottom flask was charged with 1 equivalent of the aldehyde and 1.1 equivalent of an alkyl or arylthiotrimethylsilane. Upon addition of $5\times10^{-4}$ equivalents of the solid potassium cyanide-18-crown-6 complex, the reaction was initiated. Often the reaction becomes exothermic and requires cooling with an ice bath. Upon completion of the reaction, the O-trimethylsilylhemimethylthioacetal products were typically isolated by direct distillation from the crude mixture.

Figure 11:
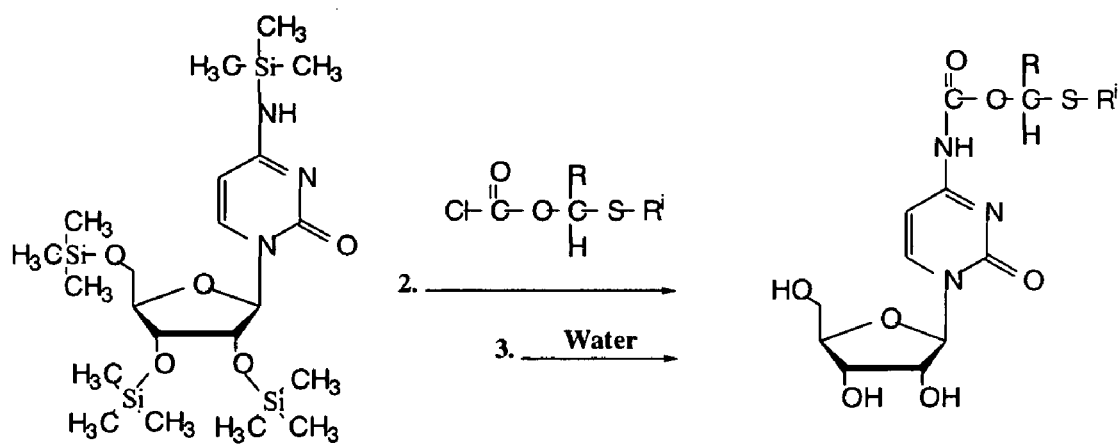
FIG. 11 illustrates the selective protection of exocyclic amine with hemimethylthioacetal chloroformate reagents.
Figure 12:
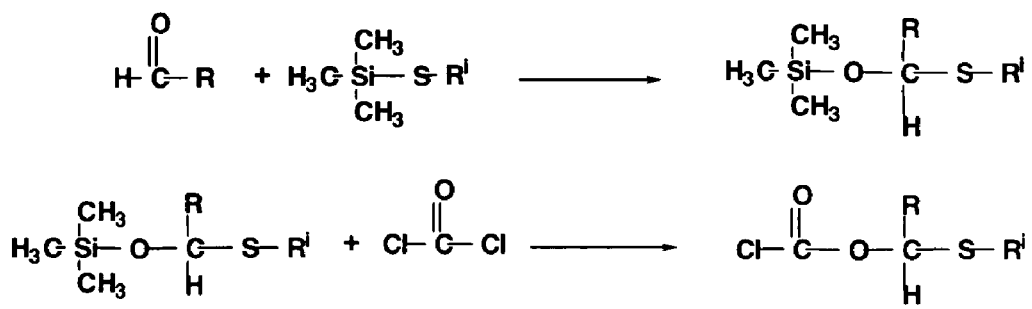
FIG. 12 illustrates the synthesis of O-trimethylsilylhemimethylthioacetal as an intermediate in the preparation of the corresponding chloroformate.

FIG. 11 illustrates the selective protection of exocyclic amine with hemimethylthioacetal chloroformate reagents. FIG. 12 illustrates the synthesis of O-trimethylsilylhemimethylthioacetals as intermediates in the preparation of the corresponding chloroformate.

General Procedure for the Synthesis of O-Trimethylsilylhemimethylthioketals as Intermediates in the Preparation of Pyrocarbonates for the Synthesis of Group V Amino Reactive Protecting Groups To a dry 25-mL flask was added 10 mg (0.03 mmol)) of anhydrous zinc iodine, 10 mg (0.15 mmol) of imidazole, and 10 mmol of the aldehyde or ketone in 5 mL of anhydrous ether. To this stirred solution was added 22 mmol of the appropriate thiosilane. General reaction time of 1 hr at 25° C. was observed. Typically, the products were isolated by distillation after dilution with ether, followed by extraction with water. The ether layer was typically evaporated, and the residual distilled at reduced pressure.

Figure 13:
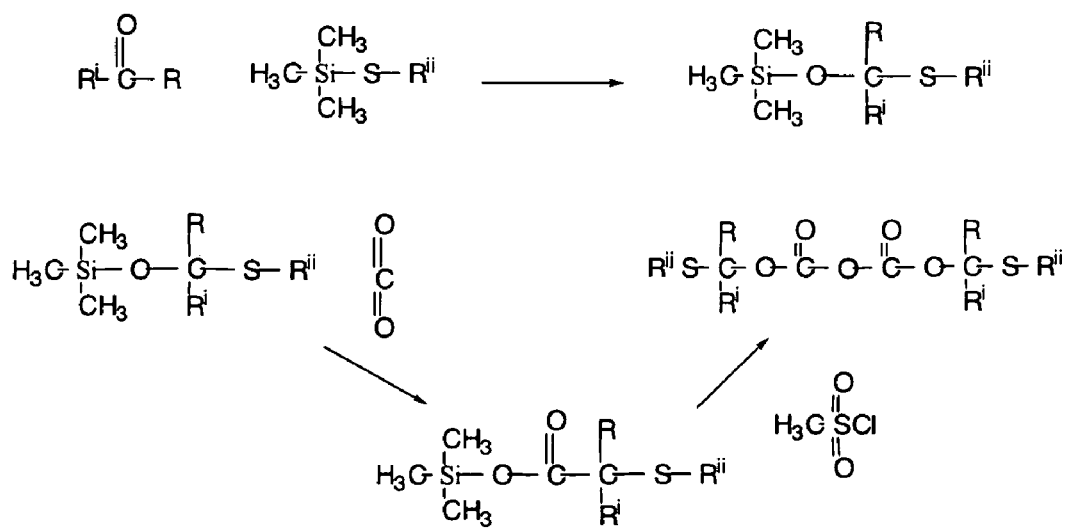
FIG. 13 illustrates the O-trimethylsilylhemimethylthioketals as intermediate in the preparation of the corresponding pyrocarbonate.
Figure 14:
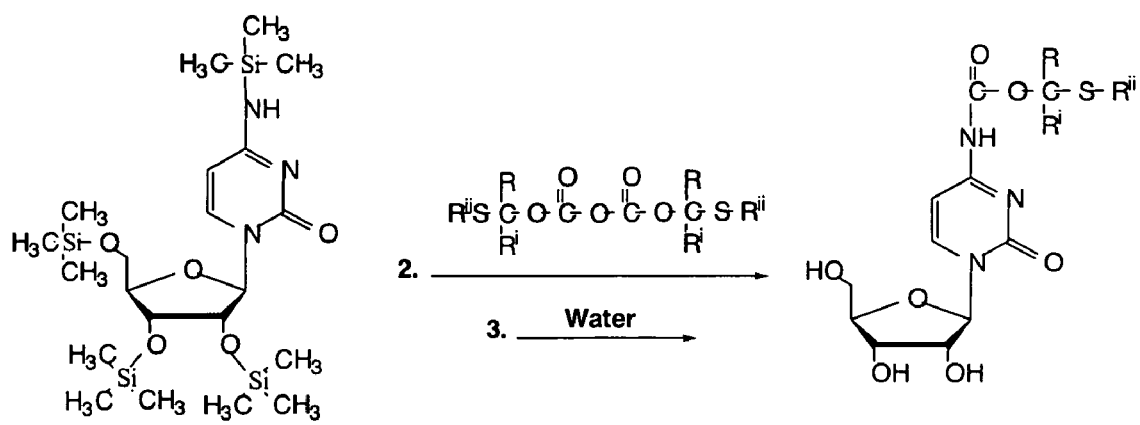
FIG. 14 illustrates the selective protection of exocyclic amine with hemimethylthioketal pyrocarbonate reagents.
Figure 15:
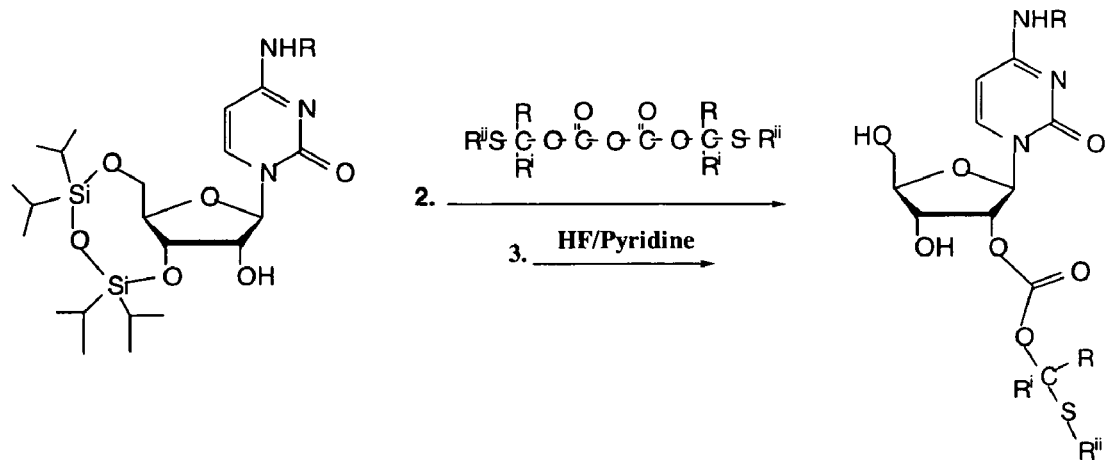
FIG. 15 illustrates the selective protection of 2'-hydroxyl with hemimethylthioketal pyrocarbonate reagents.

FIG. 13 illustrates O-trimethylsilylhemimethylthioketals as intermediate in the preparation of the corresponding pyrocarbonate. FIG. 14 illustrates the selective protection of exocyclic amine with hemimethylthioketal pyrocarbonate reagents. FIG. 15 illustrates the selective protection of 2'-hydroxyl with hemimethylthioketal pyrocarbonate reagents.

Exocyclic Amino Protecting Group Examples

Group I

Synthesis of N-(methylthiomethyloxycarbonyl) ribonucleosides

Acetic acid methylthiomethyl ester (50 mmol) was purchased from TCI America (Portland, OR) and dissolved in 200 mL of ether, and 100 mL of a 1.0 M solution of KOH in water was added. The reaction was allowed to stir overnight and the ether solution separated and evaporated to an oil. The resulting methylthiomethyl hemiacetal was dissolved in anhydrous toluene with an equal molar amount of anhydrous pyridine. A phosgene solution (6 molar equivalents) was cooled on a dry ice/ethanol bath, and the hemiacetal solution added dropwise. The solution was allowed to warm to room temperature and filtered under a blanket of dry argon gas. The resulting clear solution was evaporated to an oil using a rotary evaporator attached to a Teflon head diaphragm pump to produce methylthiomethylchloroformate. The evaporation process removed the solvent and excess phosgene. The exhaust from the pump was bubbled through an aqueous solution of KOH to neutralize the excess phosgene. A ribonucleoside (10 mmole) was coevaporated 3 times with pyridine and then dried on vacuum pump for 2 hours. Anhydrous pyridine (50 mL) and trimethylsilyl chloride (8.8 ml, 70 mmole) were added, and the mixture was stirred at room temperature for 2 hours. Methylthiomethylchloroformate (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of $NaHCO_3$. The precipitated product was dried and utilized in the next reactions.

Group II

Synthesis of N-(methylthiocarbamate) ribonucleosides

Methylthiochloroformate was purchased from Aldrich. A ribonucleoside (10 mmole) was coevaporated 3 times with pyridine, and then dried on a vacuum pump for 2 hours. Anhydrous pyridine (50 mL) and trimethylsilyl chloride (8.8 ml, 70 mmole) were added, and the mixture was stirred at room temperature for 2 hours.

Methylthiochloroformate (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of $NaHCO_3$. The precipitated product was dried and utilized in the next reactions.

Group III

Synthesis of 5',3'-O-(Tetraisopropyldisiloxane-1,3-diyl) N-thiomethylacetyl riboguanosine 5',3'-O-(Tetraisopropyldisiloxane-1,3-diyl) riboguanosine (20 mmole) was coevaporated 3 times with pyridine and then dried on vacuum pump for 2 hours. Anhydrous pyridine (100 mL) and trimethylsilyl chloride (12.8 ml, 100 mmole) were added, and the mixture was stirred at room temperature for 2 hours. Thiomethyacetyl chloride (24 mmole) was then added, and stirring continued for another 12 hours. Water (100 mL) was added to quench the reaction and hydrolyze trimethylsilyl groups. The reaction mixture was left for 1 hour. Crude product was extracted with DCM, washed with 5% aqueous solution of NaHCO$_3$, and purified by column chromatography using CHCl$_3$ with a gradient of methanol (0-3%). The yield was about 69%.

Group IV

Synthesis of N-(carbonyloxy-1-phethylthiomethyl-1-H-isobutane) ribonucleosides A dry, round bottom flask was charged with 5 mL (55.1 mmol) of isobutyraldehyde and 10.4 g (57 mmol) of phenylthiosilane. Upon addition of 10 mg of the solid potassium cyanide-18-crown-6 complex, the reaction was initiated. The reaction became exothermic and required cooling with an ice bath. Upon completion of the reaction, the O-trimethylsilyl-1-phethylthiomethyl-1-H-isobutane, 11.3 grams (81% yield), was isolated by direct distillation from the crude mixture at 71° C. at 0.05 mm Hg.

The resulting O-trimethylsilyl-1-phethylthiomethyl-1-H-isobutane was dissolved in anhydrous toluene with an equal molar amount of anhydrous pyridine. A phosgene solution (6 molar equivalents) was cooled on a dry ice/ethanol bath, and the O-trimethylsilyl-1-phethylthiomethyl-1-H-isobutane solution added dropwise. The solution was allowed to warm to room temperature and filtered under a blanket of dry argon gas. The resulting clear solution was evaporated to an oil using a rotary evaporator attached to a Teflon head diaphragm pump to produce phethylthiomethyl-1-H-isobutryloxy chloroformate. A ribonucleoside (10 mmole) was coevaporated 3 times with pyridine and then dried on vacuum pump for 2 hours. Anhydrous pyridine (50 mL) and trimethylsilyl chloride (8.8 ml, 70 mmole) were added, and the mixture stirred at room temperature for 2 hours. Phethylthiomethyl-1-H-isobutryloxy chloroformate (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of NaHCO$_3$. The precipitated product can be dried and utilized in the next reactions.

Group V

Synthesis of N-(Carbonyloxy-1-methylthiomethylcyclohexane) Ribonucleosides

To a dry 100-mL flask was added 30 mg (0.09 mmol) of anhydrous zinc iodine, 30 mg (0.45 mmol) of imidazole, and 5.89 grams of cyclohexanone (60 mmol) of in 15 mL of anhydrous ether. To this stirred solution was added 8.1 grams (66 mmol) of methylthiosilane. The reaction was allowed to stir at room temperature for 1 hour and then diluted with 50 mL of ether. The ether was extracted with water and dried over sodium sulfate. The ether was evaporated, and the product distilled at 45° C. at 0.01 mm Hg, giving 10.2 grams of 1-trimethylsilyloxy-1-methylthiomethylcyclohexane at about 84% yield.

A 250 mL four-necked flask equipped with a stirrer, a thermometer, a gas-inlet tube, and a dropping funnel was filled with nitrogen, 1-trimethylsilyloxy-1-methylthiomethylcyclo-hexane (10.2 g, 50 mmol), and hexane (100 mL). Through the mixture in the flask, carbon dioxide gas (1.4 liters, 60 mmol) was bubbled at 0° C. using a gas dispersion tube over one hour while stirring. Then, to the resulting slurry type mixture, pyridine (80 mg, 1 mmol) was added at 0° C., and then methanesulfonyl chloride (2.87 g, 25 mmol) was dropwise added at the same temperature, followed by stirring at the same temperature for 2.5 hours. After the reaction, 5% sulfuric acid (25 ml) was added to the reaction mixture, and the mixture was stirred for 30 minutes and then kept standing to separate. The resulting organic layer was washed with a 5% aqueous solution of sodium bicarbonate and water successively and concentrated under reduced pressure at 35 to 40° C. to obtain colorless liquid bis-(1-methylthiomethylcyclohexane) pyrocarbonate (16.1 g). The yield was 89%. This product was analyzed by gas chromatography. The purity was about 98.6% by GC/MS.

A ribonucleoside (10 mmole) was coevaporated 3 times with pyridine, and then dried on a vacuum pump for 2 hours. Anhydrous pyridine (50 mL) and trimethylsilyl chloride (8.8 ml, 70 mmole) were added, and the mixture was stirred at room temperature for 2 hours. bis-(-1-Methylthiomethylcyclohexane) pyrocarbonate 7.24 grams (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of NaHCO$_3$. The precipitated product was dried and utilized in the next reactions.

Group VI

Synthesis of N-(4-thiomethylbenzoyl) ribonucleosides 4-(Methylthio)benzoic acid (50 mmol) was purchased from Aldrich and dissolved in anhydrous hexanes. A large excess of oxalyl chloride (Aldrich) was added to the hexanes solution, and the mixture fitted with a reflux condenser. The reaction was refluxed overnight, and the acid chloride isolated by evaporation.

Ribonucleoside (10 mmole) was coevaporated 3 times with pyridine and then dried on vacuum pump for 2 hours. Anhydrous pyridine (50 mL) and trimethylsilyl chloride (6.3 ml, 50 mmole) were added, and the mixture was stirred at room temperature for 2 hours. 4-thiomethylbenzoyl chloride (11 mmole) was then added, and stirring continued for another 48 hours. Water (10 mL) was added to quench the reaction and hydrolyze trimethylsilyl groups. The reaction mixture was left overnight. Crude product was extracted with DCM, washed with 5% aqueous solution of NaHCO$_3$, and purified by column chromatography, using CHCl$_3$ with a gradient of methanol (0-5%). The yields were: A 46%; C 56%; and G 8%.

Group VII

Synthesis of N-(2-thiomethylbenzoyl) ribonucleosides 2-(Methylthio)benzoic acid (50 mmol) was purchased from Aldrich and dissolved in anhydrous hexanes. A large excess of oxalyl chloride (Aldrich) was added to the hexanes solution, and the mixture fitted with a reflux condenser. The reaction was refluxed overnight, and the 2-thiomethylbenzoyl chloride isolated by evaporation.

Ribonucleoside (10 mmole) was coevaporated 3 times with pyridine and then dried on vacuum pump for 2 hours. Anhydrous pyridine (50 mL) and trimethylsilyl chloride (6.3 ml, 50 mmole) were added, and the mixture was stirred at room temperature for 2 hours. 2-Thiomethylbenzoyl chloride (11 mmole) was then added, and stirring continued for another 48 hours. Water (10 mL) was added to quench the reaction and hydrolyze trimethylsilyl groups. The reaction mixture was left overnight. Crude product was extracted with DCM, washed with 5% aqueous solution of NaHCO3, and purified. The yields were: A 44%; C 62%; and G 31%.

Group VIII

Synthesis of N-(2-thiomethylphenoxycarbonyl) ribonucleosides

2-Thiomethylphenyl chloroformate was made in situ by the reaction of 2-(methyl-mercapto)phenol (Aldrich) with a 20% phosgene solution in toluene (Fluka). The phenol was dissolved in anhydrous toluene with an equal molar amount of anhydrous pyridine. The phosgene solution (6 molar equivalents) was cooled on a dry ice/ethanol bath, and the phenol solution added dropwise. The solution was allowed to warm to room temperature and filtered under a blanket of dry argon gas. The resulting clear solution was evaporated to an oil using a rotary evaporator attached to a Teflon head diaphragm pump. The evaporation process removed the solvent and excess phosgene. The exhaust from the pump was bubbled through an aqueous solution of KOH to neutralize the excess phosgene. A ribonucleoside (10 mmole) was coevaporated 3 times with pyridine and then dried on vacuum pump for 2 hours. Anhydrous pyridine (50 mL) and trimethylsilyl chloride (8.8 ml, 70 mmole) were added, and the mixture was stirred at room temperature for 2 hours. 2-Thiomethylphenyl chloroformate (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of NaHCO$_3$. The precipitated product was dried and utilized in the next reactions.

Synthesis of 5',3'-O-(Tetraisopropyldisiloxane-1,3-diyl) N-(2-thiomethylphenoxycarbonyl) ribonucleosides 5',3'-O-(Tetraisopropyldisiloxane-1,3-diyl) ribonucleoside (10 mmole) was coevaporated 3 times with pyridine, and then dried on vacuum pump for 2 hours. Anhydrous pyridine (50 mL) and trimethylsilyl chloride (6.3 ml, 50 mmole) were added, and the mixture was stirred at room temperature for 2 hours. 2-thiomethylphenyl chloroformate (20 mmole) was then added, and stirring continued for another 12 hours. Water (10 mL) was added to quench the reaction and hydrolyze trimethylsilyl groups. The reaction mixture was left overnight. Crude product was extracted with DCM, washed with 5% aqueous solution of NaHCO$_3$, and purified by column chromatography using CHCl$_3$ with a gradient of methanol (0-4%).

Group IX

Synthesis of N-(4-thiomethylphenoxycarbonyl) ribonucleosides

4-Thiomethylphenyl chloroformate was made in situ by the reaction of 4-(methyl-mercapto)phenol (Aldrich) with a 20% phosgene solution in toluene (Fluka). The phenol was dissolved in anhydrous toluene with an equal molar amount of anhydrous pyridine. The phosgene solution (6 molar equivalents) was cooled on a dry ice/ethanol bath, and the phenol solution added dropwise. The solution was allowed to warm to room temperature and filtered under a blanket of dry argon gas. The resulting clear solution was evaporated to an oil using a rotary evaporator attached to a Teflon head diaphragm pump. The evaporation process removed the solvent and excess phosgene. The exhaust from the pump was bubbled through an aqueous solution of KOH to neutralize the excess phosgene. A ribonucleoside (10 mmole) was coevaporated 3 times with pyridine and then dried on vacuum pump for 2 hours. Anhydrous pyridine (50 mL) and trimethylsilyl chloride (8.8 ml, 70 mmole) were added, and the mixture was stirred at room temperature for 2 hours. 4-Thiomethylphenyl chloroformate (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of NaHCO$_3$. The precipitated product was dried and utilized in the next reactions.

Synthesis of 5',3'-O-(Tetraisopropyldisiloxane-1,3-diyl) N-(4-thiomethylphenoxy-carbonyl) ribonucleosides 4-Thiomethylphenyl chloroformate was made in situ by the reaction of 4-(methyl-mercapto)phenol (Aldrich) with a 20% phosgene solution in toluene (Fluka). The phenol was dissolved in anhydrous toluene with an equal molar amount of anhydrous pyridine. The phosgene solution (6 molar equivalents) was cooled on a dry ice/ethanol bath, and the phenol solution added dropwise. The solution was allowed to warm to room temperature and filtered under a blanket of dry argon gas. The resulting clear solution was evaporated to an oil using a rotary evaporator attached to a Teflon head diaphragm pump. The evaporation process removed the solvent and excess phosgene. The exhaust from the pump was bubbled through an aqueous solution of KOH to neutralize the excess phosgene. 5',3'-O-(Tetraisopropyldisiloxane-1,3-diyl) ribonucleoside (10 mmole) was coevaporated 3 times with pyridine and then dried on vacuum pump for 2 hours. Anhydrous pyridine (50 mL) and trimethylsilyl chloride (6.3 ml, 50 mmole) were added, and the mixture was stirred at room temperature for 2 hours. 4-Thiomethylphenyl chloroformate (20 mmole) was then added, and stirring continued for another 12 hours. Water (10 mL) was added to quench the reaction and hydrolyze trimethylsilyl groups. The reaction mixture was left overnight. Crude product was extracted with DCM, washed with 5% aqueous solution of NaHCO$_3$, and purified by column chromatography using CHCl$_3$ with a gradient of methanol (0-3%).

Group X

Synthesis of N-(t-butylthiocarbamate) ribonucleosides t-Butylthiochloroformate was made in situ by the reaction of sodium 2-methyl-2-propanethiolate (Aldrich) with a 20% phosgene solution in toluene (Fluka). The sodium 2-methyl-2-propanethiolate was suspended in anhydrous toluene. The phosgene solution (6 molar equivalents) was cooled on a dry ice/ethanol bath, and the sodium 2-methyl-2-propanethiolate solution added dropwise. The solution was allowed to warm to room temperature and filtered under a blanket of dry argon gas. The resulting clear solution was evaporated to an oil using a rotary evaporator attached to a Teflon head diaphragm pump. Due to the low boiling point of the resulting chloroformate, the water bath on the rotary evaporator was kept to 20° C. The evaporation process removed the solvent and excess phosgene. The exhaust from the pump was bubbled through an aqueous solution of KOH to neutralize the excess phosgene. A ribonucleoside (10 mmole) was coevaporated 3 times with pyridine and then dried on vacuum pump for 2 hours. Anhydrous pyridine (50 mL) and trimethylsilyl chloride (8.8 ml, 70 mmole) were added, and the mixture was stirred at room temperature for 2 hours. t-Butylthiochloroformate (20 mmole) was then added, and stirring continued for another 12 hours. Water (10 mL) was added to quench the reaction and hydrolyze trimethylsilyl groups. The reaction mixture was left overnight. Crude product was evaporated to remove the excess pyridine, and 200 mL of DCM was added with 5% aqueous solution of NaHCO$_3$. The precipitated product was dried and utilized in the next reactions.

TABLE 1

Deprotection Time of various APG exocyclic amino Protecting groups in a solution of 5% Hydrogen Peroxide in AMP buffer pH~9/methanol (50/50, v/v).

| APG- | N4-APG-Cytidine | N6-APG-Adenosine | N2-APG-Guanosine |
|---|---|---|---|
| Phenoxyacetyl | <1 min | <30 min | <8 hrs |
| 4-t-butylphenoxyacetyl | <1 min | <30 min | <8 hrs |
| Acetyl | <1 min | <30 min | <8 hrs |
| Chloroacetyl- | <1 min | <30 min | <8 hrs |
| dichloroacetyl | <1 min | <30 min | <8 hrs |
| trichloroacetyl | <1 min | <30 min | <8 hrs |
| Fluoroacetyl | <1 min | <30 min | <8 hrs |
| Difluoroacetyl | <1 min | <30 min | <8 hrs |
| Trifluoroacetyl | <1 min | <30 min | <8 hrs |
| Nitroacetyl | <1 min | <30 min | <8 hrs |
| n-propionyl | <30 min | <2 hrs | stable |
| n-butyryl | <30 min | <2 hrs | stable |
| i-butyryl | <30 min | <2 hrs | stable |
| n-pentanoyl | <30 min | <2 hrs | stable |
| i-pentanoyl | <30 min | <2 hrs | stable |
| t-pentanoyl | <30 min | <2 hrs | stable |
| MeSCH2CO | <60 min | <6 hrs | >24 hrs |
| PHSCH2CO | <60 min | <6 hrs | >24 hrs |
| 2-Cl-PhSCH2CO | <60 min | <6 hrs | >24 hrs |
| 3-Cl-PhSCH2CO | <60 min | <6 hrs | >24 hrs |
| 4-Cl-PhSCH2CO | <60 min | <6 hrs | >24 hrs |
| 2-NO2-Benzoyl | <60 min | <6 hrs | >24 hrs |
| 3-NO2-Benzoyl | <60 min | <6 hrs | >24 hrs |
| 4-NO2-Benzoyl | <60 min | <6 hrs | >24 hrs |
| 2-Cl-Benzoyl | <60 min | <6 hrs | >24 hrs |
| 3-Cl-Benzoyl | <60 min | <6 hrs | >24 hrs |
| 4-Cl-Benzoyl | <60 min | <6 hrs | >24 hrs |
| 2,4-di-Cl-Benzoyl | <60 min | <6 hrs | >24 hrs |
| 2-F-Benzoyl | <60 min | <6 hrs | stable |
| 3-F-Benzoyl | <60 min | <6 hrs | stable |
| 4-F-Benzoyl | <60 min | <6 hrs | stable |
| 2-CF3-Benzoyl | <60 min | <6 hrs | >24 hrs |
| 3-CF3-Benzoyl | <60 min | <6 hrs | >24 hrs |
| 4-CF3-Benzoyl | <60 min | <6 hrs | >24 hrs |
| Benzoyl | <60 min | <6 hrs | stable |
| 2-MeO-Benzoyl | <2 hrs | <24 hrs | stable |
| 3-MeO-Benzoyl | <2 hrs | <24 hrs | stable |
| 4-MeO-Benzoyl | <2 hrs | <24 hrs | stable |
| 2-Me-Benzoyl | <2 hrs | <24 hrs | stable |
| 3-Me-Benzoyl | <2 hrs | <24 hrs | stable |
| 4-Me-Benzoyl | <2 hrs | >24 hrs | stable |
| 2,4-di-Me-Benzoyl | <6 hrs | >24 hrs | stable |
| 2,4,6-tri-Me-Benzoyl | <6 hrs | >24 hrs | stable |
| t-Butyl-SCO | <24 hrs | <24 hrs | <24 hrs |
| Methyl-SCO | <24 hrs | <24 hrs | <24 hrs |
| Ethyl-SCO | <24 hrs | <24 hrs | <24 hrs |
| Propyl-SCO | <24 hrs | <24 hrs | <24 hrs |
| i-propyl-SCO | <24 hrs | <24 hrs | <24 hrs |
| Phenyl-SCO | <24 hrs | <24 hrs | <24 hrs |
| 2-Cl-PhSCO | <24 hrs | <24 hrs | <24 hrs |
| 3-Cl-PhSCO | <24 hrs | <24 hrs | <24 hrs |
| 4-Cl-PhSCO | <24 hrs | <24 hrs | <24 hrs |
| 2-F-PhSCO | <24 hrs | <24 hrs | <24 hrs |
| 3-F-PhSCO | <24 hrs | <24 hrs | <24 hrs |
| 4-F-PhSCO | <24 hrs | <24 hrs | <24 hrs |
| 2-CF3-PhSCO | <24 hrs | <24 hrs | <24 hrs |
| 3-CF3-PhSCO | <24 hrs | <24 hrs | <24 hrs |
| 4-CF3-PhSCO | <24 hrs | <24 hrs | <24 hrs |
| 2-NO2-PhSCO | <24 hrs | <24 hrs | <24 hrs |
| 3-NO2-PhSCO | <24 hrs | <24 hrs | <24 hrs |
| 4-NO2-PhSCO | <24 hrs | <24 hrs | <24 hrs |
| 2-OMe-PhSCO | <24 hrs | <24 hrs | <24 hrs |
| 3-OMe-PhSCO | <24 hrs | <24 hrs | <24 hrs |
| 4-OMe-PhSCO | <24 hrs | <24 hrs | <24 hrs |

2'-Hydroxyl Protecting Group Examples

Figure 16:
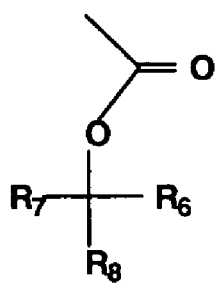
FIG. 16 illustrates the 2'-hydroxyl protective groups.
Figure 16:
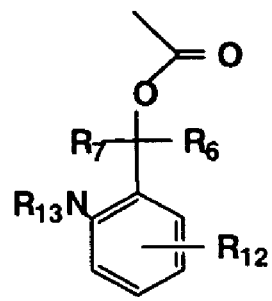
Figure 16:
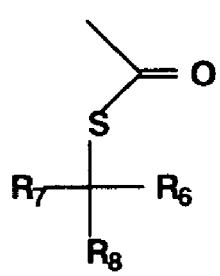
Figure 16:
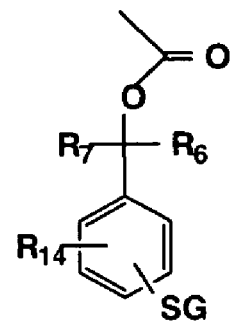
Figure 16:
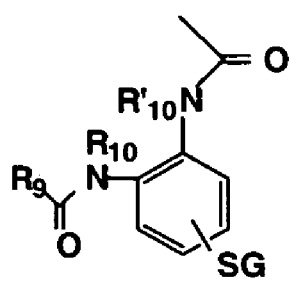
Figure 16:
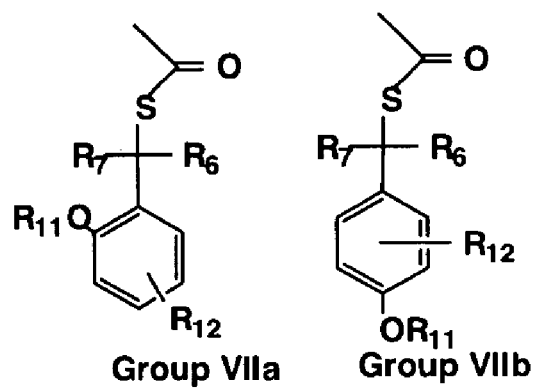
Figure 16:
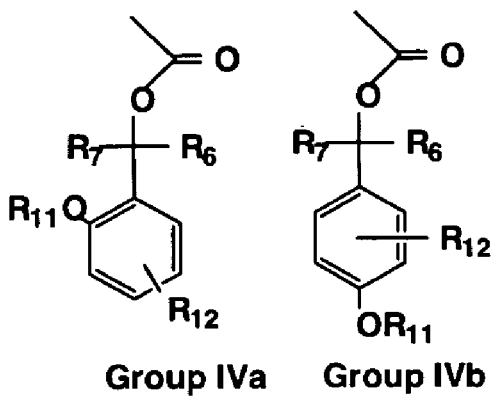
Figure 16:
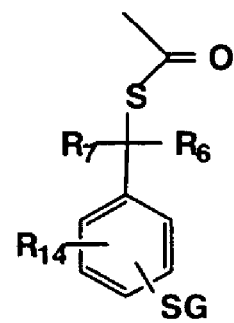

FIG. 16 illustrates examplary 2'-hydroxyl protective groups.

General procedure for the synthesis of 5',3'-O-(Tetraisopropyldisiloxane-1,3-diyl)-2'-O-tert-butyl thiocarbonate-N-tert-butyl thiocarbonate Protected ribonucleosides 5',3'-O-(Tetraisopropyldisiloxane-1,3-diyl) ribonucleoside (20 mmole) was coevaporated 3 times with pyridine and then dried on vacuum pump for 12 hours. Anhydrous pyridine (200 mL) and appropriate chloroformate (120 mmole) were added, and the mixture was stirred at room temperature for 12 hours. The product was purified by column chromatography using hexanes with a gradient of ethyl acetate (0-60%).

Group I

Example 1

Synthesis of 5',3'-O-(Tetraisopropyldisiloxane-1,3-diyl)-2'-O-(2-(1-oxy-1-methylethyl)1,3-dithiane) Protected ribonucleosides 5', 3'-O-(tetraisopropyldisiloxane-1,3-diyl) ribonucleoside (10 mmole) was coevaporated 3 times with pyridine and then dried on vacuum pump for 12 hours. Anhydrous pyridine (100 mL), p-nitrophenyl chloroformate (3.02 g, 15 mmole), and DMAP (488 mg, 4 mmole) were added, and the mixture was stirred at room temperature for 12 hours. The 2'-O-(4-nitrophenyl carbonate) derivate was isolated by flash chromatography, using hexanes with a gradient of ethyl acetate (0-100%) and then dried on vacuum pump for 12 hours.

1,3-Dithiane (4.08 g, 34.00 mmol) in THF (80 mL) was added to n-butyl lithium (37.40 mmol) at -78° C. The mixture was allowed to warm to 0° C. on an ice/water bath and then stirred for 30 min. The mixture was once again cooled to -78° C., and a solution of freshly distilled acetone (3.74 mL, 50.94 mmol) in anhydrous THF (50 mL) was added drop-wise with stirring. The mixture was allowed to warm to room temperature and stirred to keep the lithium salt of 2-(1-hydroxy-1-methylethyl)1,3-dithiane suspended.

The 5', 3'-O-(Tetraisopropyldisiloxane-1,3-diyl) 2'-O-(4-nitrophenyl carbonate) ribonucleoside was redissolved in anhydrous pyridine (75 mL), and the THF solution of 2-(1-hydroxy-1-methylethyl)1,3-dithiane was added. The mixture was stirred at room temperature for 12 hours. The final product was purified by flash chromatography using hexanes with a gradient of ethyl acetate (0-30%). The yield was about 74%.

Example 2

Synthesis of 5', 3'-O-(Tetraisopropyldisiloxane-1,3-diyl)-2'-O-(1,1,1,3,3,3-hexafluoro-2-oxy-2-methyl-2-propane) Protected ribonucleosides 5', 3'-O-(Tetraisopropyldisiloxane-1,3-diyl) ribonucleoside (10 mmole) was coevaporated 3 times with pyridine and then dried on vacuum pump for 12 hours. Anhydrous pyridine (100 mL), p-nitrophenyl chloroformate (3.02 g, 15 mmole), and DMAP (488 mg, 4 mmole) were added, and the mixture was stirred at room temperature for 12 hours. The 2'-O-(4-nitrophenyl carbonate) derivate was isolated by flash chromatography using hexanes with a gradient of ethyl acetate (0-100%) and then dried on vacuum pump for 12 hours. Anhydrous pyridine (75 mL) and sodium 1,1,1,3,3,3-hexafluoro-2-methyl-2-propanolate (1.68 g, 15 mmole) were added, and the mixture was stirred at room temperature for 12 hours. The final product was purified by flash chromatography using hexanes with a gradient of ethyl acetate (0-30%). The yield was about 22%.

Group II

Example 3

General produce for the synthesis of 5',3'-O-(Tetraisopropyldisiloxane-1,3-diyl) 2'-O-(tert-butyl thiocarbonate) protected ribonucleosides (two-step procedure):

5',3'-O-(Tetraisopropyloxane-1,3-diyl) ribonucleoside (10 mmole) was coevaporated 3 times with pyridine and then dried on vacuum pump for 12 hours. Anhydrous pyridine (100 mL), p-nitrophenyl chloroformate (3.02 g, 15 mmole), and DMAP (488 mg, 4 mmole) were added, and the mixture was stirred at room temperature for 12 hours. The 2'-O-(4-nitrophenyl carbonate) derivate was isolated by flash chromatography using hexanes with a gradient of ethyl acetate (0-100%) and then dried on vacuum pump for 12 hours. Anhydrous pyridine (75 mL) and sodium 2-methyl-2-propanethiolate (1.68 g, 15 mmole) were added, and the mixture was stirred at room temperature for 12 hours. The final product was purified by flash chromatography using hexanes with a gradient of ethyl acetate (0-30%). The yields were about 76% for tert-Butyl thiocarbonate U analog, about 63% for tert-Butyl thiocarbonate rA-iBu analog, and 18% for tert-Butyl thiocarbonate rG-AcSMe analog.

General produre for the synthesis of 5',3'-O-(Tetraisopropyldisiloxane-1,3-diyl) 2'-O-carbonate/thiocarbonate protected ribonucleosides (one-step procedure):

5',3'-O-(Tetraisopropyldisiloxane-1,3-diyl) ribonucleoside (20 mmole) was coevaporated 3 times with pyridine and then dried on vacuum pump for 12 hours. Anhydrous pyridine (200 mL) and an appropriate chloroformate (120 mmole) were added, and the mixture was stirred at room temperature for 12 hours. The product was purified by column chromatography using hexanes with a gradient of ethyl acetate (0-60%). The yields were about 76% for tert-Butyl thiocarbonate U analog and 61% for tert-Butyl thiocarbonate rC-Ac analog.

Group III

Example 5

Synthesis of 5', 3'-O-(Tetraisopropyldisiloxane-1,3-diyl)-2'-O-(2-thiomethylacetamide)phenylcarbamate protected ribonucleosides 2-Nitrophenylaniline (6.9 gm 50 mmol) was dissolved in 100 mL of anhydrous pyridine. Thiomethyacetyl chloride (55 mmole) was then added, and the reaction stirred for 12 hours. The excess thiomethyacetyl chloride was neutralized by the addition of 10 mL of methanol, and the reaction evaporated to dryness. The product, 2-nitro-1-thiomethyl-phenylacetamide, was purified by silica gel flash chromatography in methylene chloride with a gradient of methanol (0-5%). The product was converted to the aniline deravitive using a Raney nickel alloy with ammonium chloride in water as described by Bhumik and Akamanchi, (Can. J. Chem. Vol 81, 2003 197-198), which was incorporated herein by reference. The aniline derivative (10 mmol) was converted to the isocyanate in situ by dissolving in toluene (50 mL) with 10% pyridine. A 20% solution of phosgene (10 mL) in toluene (Fluka) was placed in a 100 mL round bottom flask and cooled to -78° C. The aniline solution was added dropwise, and the reaction allowed to warm to 0° C. and stirred overnight. The solution was allowed to warm to room temperature and filtered under a blanket of dry argon gas. The resulting clear solution was evaporated to an oil using a rotary evaporator attached to a Teflon head diaphragm pump. The excess phosgene and HCl was removed by evaporation. The exhaust from the pump was bubbled through an aqueous solution of KOH to neutralize the excess phosgene. The resulting crude isocyanate, 5',3'-O-(Tetraisopropyldisiloxane-1,3-diyl) uridine (3 mmole), was coevaporated 3 times with pyridine and then dried on vacuum pump for 2 hours. Anhydrous pyridine (2 mL) and isocyanate (6 mmole) were added, and the mixture was stirred at room temperature for 3 hours. The product was purified by column chromatography using $CHCl_3$ with a gradient of methanol (0-3%). The yields were about 64% for uridine 5', 3'-O-(Tetraisopropyldisiloxane-1,3-diyl)-2'-O-(2-thiomethylacetamide)phenylcarbamate.

Group IV

Example 6

Synthesis of 5'-Dimethoxytrityl-2'-O-(2-triisopropyl-silyloxy)dimethylphenylmethyl -carbonate protected ribonucleosides 2-Hydroxylacetophenone (15 g, 110 mmol) was dissolved in anhydrous dichloromethane (150 mL) with triethyl amine (250 mmol). Triisopropylsilyl chloride (130 mmol) was dissolved in anhydrous dicholormethane (50 mL) and added to the stirring solution of the acetophenone. The reaction was allowed to stir at room temperature overnight and was quenched by the addition of water (200 mL). The dichloromethane layer was separated and dried over sodium sulfate. The silylated acetophenone was purified by flash chromatography in hexanes with an ethyl acetate gradient (0 to 30%). The purified silylated acetophenone (30 mmol) was redissolved in ether and cooled to 0° C. on an ice/water bath. Methyl magnesium bromide (33 mmol) in ether (1.0 M, Aldrich) was added dropwise to the stirring solution, and the reaction allowed to react for 30 minutes at 0° C. This solution was added directly to a solution of phosgene (30mmol) at −20° C. The phosgene reaction was allowed to stir at −20° C. for 30 min and then added to a pyridine solution of 5'-dimethoxytrityl uridine (ChemGenes, Waltham, Mass.). The reaction was allowed to stir overnight and warm to room temperature. The reaction was neutralized by the addition of 10 mL of water and evaporated to an oil. The crude reaction was purified directly on silica gel chromatography using methylene chloride with a methanol gradient (1-4%). Two main products were isolated, including of the 2' and 3' protected isomers. The yields were about 19% for uridine-5'-DMT-2'-O-(2-triisopropylsilyloxy)dimethylphenylmethyl-carbonate.

Group V

Example 7

Synthesis of 5', 3'-O-(Tetraisopropyldisiloxane-1,3-diyl)-2'-O-2-(o-thiomethyl -phenylacetamide)-2-propane carbonate Uridine 2'-Nitroacetophenone was (30 mmol) dissolved in ether and cooled to 0° C. on an ice/water bath. Methyl magnesium bromide (33 mmol) in ether (1.0 M, Aldrich) was added dropwise to the stirring solution, and the reaction allowed to react for 30 minutes at 0° C. A cold aqueous solution of ammonium chloride was added to the mixture to quench the unreacted methyl magnesium bromide and to protonate the alcohol producing the 2-(o -nitrophenyl)-2-propanol. The nitrophenyl group was reduced to the 2-(o-anisyl)-2-propanol by the method described by Bhumik and Akamanchi, (Can. J. Chem. Vol 81, 2003 197-198). The 2-(o-anisyl)-2-propanol was purified by silica gel chromatography using dichloromethane and a methanol gradient. The 2-(o-anisyl)-2-propanol (15 mmol) was dissolved in 50 mL of anhydrous pyridine. Thiomethyacetyl chloride (15 mmole) was then added, and the reaction stirred for 12 hours. The excess thiomethyacetyl chloride was neutralized by the addition of 5 mL of methanol and the reaction evaporated to dryness. The product, 2-(o-thiomethyl-phenylacetamide)-2-propanol was purified by silica gel flash chromatography in methylene chloride with a gradient of methanol (0-5%). The 2-(o -thiomethylphenylacetamide)-2-propanol (10 mmol) was dissolved in THF 30 mL and converted to the sodium salt using sodium metal. This solution was added directly to a solution of phosgene (10 mmol) at −20° C. The phosgene reaction was allowed to stir at −20° C. for 30 min and then added to a pyridine solution of 5',3'-O-(Tetraisopropyl-disiloxane-1,3-diyl) uridine (Monomer Sciences, New Market, Alabama). The reaction was allowed to stir overnight and warm to room temperature. The reaction was neutralized by the addition of 10 mL of water and evaporated to an oil. The crude reaction was purified directly on silica gel chromatography using methylene chloride with a methanol gradient (1-4%).

Group VI

Example 8

Synthesis of 5'-Dimethoxytrityl-2'-O-(2-triisopropyl-silyloxy)dimethylphenylmethyl -thiocarbonate Protected ribonucleosides 2-Hydroxylacetophenone (15 g, 110 mmol) was dissolved in anhydrous dichloromethane (150 mL) with triethyl amine (250 mmol). Triisopropylsilyl chloride (130 mmol) was dissolved in anhydrous dicholormethane (50 mL) and added to the stirring solution of the acetophenone. The reaction was allowed to stir at room temperature overnight and was quenched by the addition of water (200 mL). The dichloromethane layer was separated and dried over sodium sulfate. The silylated acetophenone was purified by flash chromatography in hexanes with an ethyl acetate gradient (0 to 30%). The purified silylated acetophenone (30 mmol) was redissolved in ether and cooled to 0° C. on an ice/water bath. Methyl magnesium bromide (33 mmol) in ether (1.0 M, Aldrich) was added dropwise to the stirring solution, and the reaction allowed to react for 30 minutes at 0° C. A cold aqueous solution of ammonium chloride was added to the mixture to quench the unreacted methyl magnesium bromide and to protonate the alcohol producing the 2-(o -triisopropyl-silyl-oxyphenyl)-2-propanol. The tertiary alcohol was then converted to a thiol by the method described by Nishio (J. Chem. Soc., Chem. Commun., 1989, 4, 205-206), which was incorporated herein by reference. The sodium thiolate was formed using sodium metal in THF and the resulting solution was added directly to a solution of phosgene (30 mmol) at −20° C. The phosgene reaction was allowed to stir at −20° C. for 30 min and then added to a pyridine solution of 5'-dimethoxytrityl uridine (ChemGenes, Waltham, Mass). The reaction was allowed to stir overnight and warm to room temperature. The reaction was neutralized by the addition of 10 mL of water and evaporated to an oil. The crude reaction was purified directly on silica gel chromatography using methylene chloride with a methanol gradient (1-4%). Two main products were isolated consisting of the 2' and 3' protected isomers.

Group VII

Example 9

Synthesis of 5', 3'-O-(Tetraisopropyldisiloxane-1,3-diyl)-2'-O-dimethylphenyl -methylthiocarbonate Protected ribonucleosides Sodium 2-phenyl-2-propanethiolate was synthesized from 2-phenyl-2-nitropropane by the method described by Komblum and Widmer (J. Am. Chem. Soc., 1987, 100:22, 7086-7088), which was incorporated herein by reference. 5',3'-O-(tetraisopropyldisiloxane-1,3-diyl) uridine (10 mmole) was coevaporated 3 times with pyridine and then dried on vacuum pump for 12 hours. Anhydrous pyridine (100 mL), p-nitrophenyl chloroformate (3.02 g, 15 mmole) and DMAP (488 mg, 4 mmole) were added, and the mixture was stirred at room temperature for 12 hours. 2'-O-(4-nitrophenyl carbonate) derivate was isolated by flash chromatography using hexanes with a gradient of ethyl acetate (0-100%) and then dried on vacuum pump for 12 hours. Anhydrous pyridine (75 mL) and Sodium 2-phenyl-2-propanethiolate (15 mmole) were added, and the mixture was stirred at room temperature for 12 hours. The final product was purified by flash chromatography using hexanes with a gradient of ethyl acetate (0-30%). The yield was about 55% for 5', 3'-O-(tetraisopropyldisiloxane-1,3-diyl)-2'-O-dimethylphenyl -methylthiocarbonate uridine.

General Procedure for the Removal of 5',3'-O-(Tetraisopropyldisiloxane-1,3-diyl) Protecting Group with Hydrogen Fluoride Pyridine Complex Anhydrous hydrogen fluoride-pyridine (3.5 mL) was carefully added to an ice-cold solution of pyridine (4 mL) in MeCN (24 mL). The mixture was stirred for about 5 minutes and then transferred via cannula to 5',3'-O-(tetraisopropyldisiloxane-1,3-diyl) 2'-O-thiocarbonate protected ribonucleoside (10 mmole). The reaction was left with stirring at room temperature for 2-3 hours. Crude reaction mixture (without concentration) was applied to the silica gel, and the product was purified by column chromatography using hexanes followed by ethyl acetate with a gradient of acetone (0-5%).

General Procedure for the Synthesis of 5'-0-(4,4'-dimethoxy-trityl)-2-O-(tert-butyl thiocarbonate)-N-(tert-butyl thiocarbonate) Protected ribonucleosides The 2'-O-(tert-butyl thiocarbonate)-N-(tert-butyl thiocarbonate) protected ribonucleoside (10 mmole) was coevaporated 3 times with pyridine and then dried on vacuum pump for 12 hours. Anhydrous pyridine (100 mL) and dimethoxytrityl chloride (4.1 g, 12 mmole) were added, and the mixture was stirred at room temperature for 12 hours. The 5'-O-(4, 4'-dimethoxy-trityl)-2'-O-(tert-butyl thiocarbonate)-N-(tert -butyl thiocarbonate) derivate was isolated by flash chromatography using hexanes with a gradient of ethyl acetate (0-100%) and then dried on vacuum pump for 12 hours.

General Procedure for the Synthesis of 5'-O-Dimethoxytrityl-2'-O-thiocarbonate ribonucleoside 3'-N,N-diisopropyl(methyl) phosphoramidites 5'-O-Dimethoxytrityl-2'-O-thiocarbonate ribonucleoside (1 mmole) was dried on a vacuum pump for 12 hours. Anhydrous THF (3 mL), 2,4,6-collidine (0.993 mL, 7.5 mmole) and N-methylimidazole (0.04 mL, 0.5 mmole) were added. N,N-diisopropylmethyl phosphonamidic chloride (0.486 mL, 2.5 mmole) was then added dropwise over 10 minutes at RT, and the reaction mixture was left with stirring for ~3 hours. Crude mixture (without concentration) was applied on the silica gel, and the product was purified by column chromatography using benzene with a gradient of ethyl acetate (0-40%).

Synthesis of Oligodeoxyribonucleotides and Oligoribonucleotides.

The solid phase synthesis of oligodeoxyribonucleotides and oligoribonucleotides was accomplished using an ABI model 394 automated DNA synthesizer from Applied Biosystems (Foster City, Calif.). The synthesis cycle was adapted from a standard one-micromolar 2-cyanoethyl-phosphoramidite RNA or DNA synthesis cycle. For the ACE chemistry, a separate synthesizer was specially adapted with Teflon tubing and fittings to handle the fluoride ion deblock conditions. The ACE chemistry was performed as described by Scaringe et. al. J. Am. Chem. Soc., 1998, 120(45) 11820-11821, which was incorporated herein by reference. The TOM chemistry was performed as described by Pitsch, et. al. in U.S. Pat. No. 5,986,084, which was incorporated herein by reference. RNA was synthesized using the 2'-TBDMS method as described by Wincott et. al., Nucleic Acids Research, 1995, 23, 2677-2684, which was incorporated herein by reference.

Deprotection with Hydrogen Peroxide Solution of Chemically Synthesized RNA with Commercially available Amino Protecting Groups

Example 1

RNA synthesized with 2'-ACE monomers. Cytidine was protected with acetyl, adenosine was protected with isobutyryl, and guanosine was protected with t-butylphenoxyacetyl (Sinha, et. al., *Biochimie*, 1993, 75, 13-23). The solid support was polystyrene containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 2

RNA was synthesized using 2'-TOM monomers. Cytidine was protected with acetyl, adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/ water. This released the RNA oligonucleotides into solution and deprotected the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 3

RNA was synthesized using 2'-TOM monomers. Cytidine was protected with acetyl, adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This released the RNA oligonucleotides into solution and deprotected the exocyclic amines. The RNA was then directly precipitated by adding 5 volumes of anhydrous ethanol, cooling on dry ice, and then isolating by centrifugation.

Example 4

RNA was synthesized using 2'-TBDMS monomers. Cytidine was protected with acetyl, adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, and deprotected the exocyclic amines. The RNA containing the 2'-TBDMS protecting groups were then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 5

RNA was synthesized using 2'-TBDMS monomers. Cytidine was protected with acetyl, adenosine was protected with isobutyryl, and guanosine was protected with t-butylphenoxyacetyl. The solid support was the polystyrene-based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This released the RNA oligonucleotides into solution and deprotected the exocyclic amines. The RNA was then directly precipitated by adding 5 volumes of anhydrous ethanol, cooling on dry ice, and then isolating by centrifugation.

Deprotection of New Amino Protecting Groups (I-X) on Chemically Synthesized RNA with Hydrogen Peroxide Solution

Example 6

RNA was synthesized with 2'-ACE monomers. Cytidine was protected with acetyl, adenosine was protected with isobutyryl, and guanosine was protected with N-(methylthiomethyloxy-carbonyl). The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 7

RNA was synthesized with 2'-ACE monomers. Cytidine was protected with acetyl, adenosine was protected with isobutyryl, and guanosine was protected with N-(methylthiocarbamate). The solid support was the polystyrene based Rapp Polymer containing a peroxide oxidizable safety catch linker. The capping step using acetic anhydride was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 8

RNA was synthesized with 2'-ACE monomers. Cytidine was protected with acetyl, adenosine was protected with isobutyryl, and guanosine was protected with N-thiomethylacetyl. The solid support was the polystyrene based Rapp Polymer containing a peroxide oxidizable safety catch linker. The capping step using acetic anhydride was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 9

RNA was synthesized with 2'-ACE monomers. Cytidine was protected with N-(carbonyloxy-1-phethylthiomethyl-1-H-isobutane), adenosine was protected with isobutyryl, and guanosine was protected with t-butylphenoxyacetyl. The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 10

RNA was synthesized with 2'-ACE monomers. Cytidine was protected with N-(carbonyloxy-1-methylthiomethylcyclohexane), adenosine was protected with isobutyryl, and guanosine was protected with t-butylphenoxyacetyl. The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 11

RNA was synthesized with 2'-ACE monomers. Cytidine was protected with acetyl, adenosine was protected with N-(4-thiomethylbenzoyl), and guanosine was protected with t-butylphenoxyacetyl. The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 12

RNA was synthesized with 2'-ACE monomers. Cytidine was protected with acetyl, adenosine was protected with N-(2-thiomethylbenzoyl), and guanosine was protected with t-butylphenoxyacetyl. The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 13

RNA was synthesized with 2'-ACE monomers. Cytidine was protected with N-(2-thiomethylphenoxycarbonyl), adenosine was protected with isobutyryl, and guanosine was protected with t-butylphenoxyacetyl. The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 14

RNA was synthesized with 2'-ACE monomers. Cytidine was protected with N-(4-thiomethylphenoxycarbonyl), adenosine was protected with isobutyryl, and guanosine was protected with t-butylphenoxyacetyl. The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 15

RNA synthesized with 2'-ACE monomers. Cytidine was protected with acetyl, adenosine was protected with isobutyryl, and guanosine was protected with N-(t-butylthiocarbamate). The solid support was the polystyrene based Rapp Polymer containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution, deprotected the exocyclic amines, and modified the 2'-ACE groups. The 2'-ACE groups were then cleaved using a buffered aqueous formic acid solution at pH 3.8 overnight.

Example 16

RNA was synthesized using 2'-TOM monomers. Cytidine was protected with N-(methylthiomethyloxycarbonyl), adenosine was protected with isobutyryl, and guanosine was protected with t-butylphenoxyacetyl. The solid support was controlled pore glass containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This released the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 17

RNA was synthesized using 2'-TOM monomers. Cytidine was protected with N-(methylthiomethyloxycarbonyl), adenosine was protected with isobutyryl, and guanosine was protected with t-butylphenoxyacetyl. The solid support was the polystyrene based Rapp Polymere containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 18

RNA was synthesized using 2'-TOM monomers. Cytidine was protected with acetyl, adenosine was protected with isobutyryl, and guanosine was protected with N-(methylthiocarbamate). The solid support was controlled pore glass containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 19

RNA was synthesized using 2'-TOM monomers. Cytidine was protected with acetyl, adenosine was protected with isobutyryl, and guanosine was protected with N-(methylthiocarbamate). The solid support was the polystyrene based Rapp Polymere containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 20

RNA was synthesized using 2'-TOM monomers. Cytidine was protected with acetyl, adenosine was protected with isobutyryl, and guanosine was protected with N-thiomethylacetyl. The solid support was controlled pore glass containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 21

RNA was synthesized using 2'-TOM monomers. Cytidine was protected with acetyl, adenosine was protected with isobutyryl, and guanosine was protected with N-thiomethylacetyl. The solid support was the polystyrene based Rapp Polymere containing. a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 22

RNA was synthesized using 2'-TOM monomers. Cytidine was protected with N-(carbonyloxy-1-phethylthiomethyl-1-H-isobutane), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 23

RNA was synthesized using 2'-TOM monomers. Cytidine was protected with N-(carbonyloxy-1-phethylthiomethyl-1-H-isobutane), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 24

RNA was synthesized using 2'-TOM monomers. Cytidine was protected with N-(carbonyloxy-1-methylthiomethylcyclohexane), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 25

RNA was synthesized using 2'-TOM monomers. Cytidine was protected with N-(carbonyloxy-1-methylthiomethylcyclohexane), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The

Example 26

RNA was synthesized using 2'-TOM monomers. Cytidine was protected with acetyl, adenosine was protected with N-(4-thiomethylbenzoyl), guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 27

RNA was synthesized using 2'-TOM monomers. Cytidine was protected with acetyl, adenosine was protected with N-(4-thiomethylbenzoyl), guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 28

RNA was synthesized using 2'-TOM monomers. Cytidine was protected with acetyl, adenosine was protected with N-(2-thiomethylbenzoyl), guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 29

RNA was synthesized using 2'-TOM monomers. Cytidine was protected with acetyl, adenosine was protected with N-(2-thiomethylbenzoyl), guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 30

RNA was synthesized using 2'-TOM monomers. Cytidine was protected with N-(2-thiomethylphenoxycarbonyl), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 31

RNA was synthesized using 2'-TOM monomers. Cytidine was protected with N-(2-thiomethylphenoxycarbonyl), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 32

RNA was synthesized using 2'-TOM monomers. Cytidine was protected with N-(4-thiomethylphenoxycarbonyl), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 33

RNA was synthesized using 2'-TOM monomers. Cytidine was protected with N-(4-thiomethylphenoxycarbonyl), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 34

RNA was synthesized using 2'-TOM monomers. Cytidine was protected with acetyl, adenosine was protected with isobutyryl, and guanosine was protected with N-(t-butylthiocarbamate). The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TOM protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 35

RNA was synthesized using 2'-TOM monomers. Cytidine was protected with acetyl, adenosine was protected with isobutyryl, and guanosine was protected with N-(t-butylthiocarbamate). The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 36

RNA was synthesized using 2'-TBDMS monomers. Cytidine was protected with N-(methylthiomethyloxycarbonyl), adenosine was protected with isobutyryl, and guanosine was protected with t-butylphenoxyacetyl. The solid support was controlled pore glass containing a peroxide oxidizable safety catch linker. The Acetic Anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6)

Example 37

RNA was synthesized using 2'-TBDMS monomers. Cytidine was protected with N-(methylthiomethyloxycarbonyl), adenosine was protected with isobutyryl, and guanosine was protected with t-butylphenoxyacetyl. The solid support was the polystyrene based Rapp Polymere containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 38

RNA was synthesized using 2'-TBDMS monomers. Cytidine was protected with acetyl, adenosine was protected with isobutyryl, and guanosine was protected with N-(methylthiocarbamate). The solid support was controlled pore glass containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 39

RNA was synthesized using 2'-TBDMS monomers. Cytidine was protected with acetyl, adenosine was protected with isobutyryl, and guanosine was protected with N-(methylthiocarbamate). The solid support was the polystyrene based Rapp Polymere containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 40

RNA was synthesized using 2'-TBDMS monomers. Cytidine was protected with acetyl, adenosine was protected with isobutyryl, and guanosine was protected with N-thiomethylacetyl. The solid support was controlled pore glass containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 41

RNA was synthesized using 2'-TBDMS monomers. Cytidine was protected with acetyl, adenosine was protected with isobutyryl, and guanosine was protected with N-thiomethylacetyl. The solid support was the polystyrene based Rapp Polymere containing a peroxide oxidizable safety catch linker. The acetic anhydride capping step was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was then directly precipitated by adding 5 volumes of anhydrous ethanol, cooling on dry ice then isolating by centrifugation.

Example 42

RNA was synthesized using 2'-TBDMS monomers. Cytidine was protected with N-(carbonyloxy-1-phethylthiomethyl-1-H-isobutane), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 43

RNA was synthesized using 2'-TBDMS monomers. Cytidine was protected with N-(carbonyloxy-1-phethylthiomethyl-1-H-isobutane), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 44

RNA was synthesized using 2'-TBDMS monomers. Cytidine was protected with N-(carbonyloxy-1-methylthiomethylcyclohexane), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 45

RNA was synthesized using 2'-TBDMS monomers. Cytidine was protected with N-(carbonyloxy-1-methylthiomethylcyclohexane), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 46

RNA was synthesized using 2'-TBDMS monomers. Cytidine was protected with acetyl, adenosine was protected with N-(4-thiomethylbenzoyl), guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF (aq) in acetonitrile at pH 8.6) for 6 hours at room temperature. The reaction mixture was diluted with water and purified by ion-exchange chromatography.

Example 47

RNA was synthesized using 2'-TBDMS monomers. Cytidine was protected with acetyl, adenosine was protected with N-(4-thiomethylbenzoyl), guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours.

This releases the RNA oligonucleotides into solution and deprotects the exocyclic amines. The RNA was directly precipitated by adding 5 volumes of anhydrous ethanol, cooling on dry ice, and then isolating by centrifugation.

Example 48

RNA was synthesized using 2'-TBDMS monomers. Cytidine was protected with acetyl, adenosine was protected with N-(2-thiomethylbenzoyl), guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 49

RNA was synthesized using 2'-TBDMS monomers. Cytidine was protected with acetyl, adenosine was protected with N-(2-thiomethylbenzoyl), guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 50

RNA was synthesized using 2'-TBDMS monomers. Cytidine was protected with N-(2-thiomethylphenoxycarbonyl), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 51

RNA was synthesized using 2'-TBDMS monomers. Cytidine was protected with N-(2-thiomethylphenoxycarbonyl), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 52

RNA was synthesized using 2'-TBDMS monomers. Cytidine was protected with N-(4-thiomethylphenoxycarbonyl), adenosine was protected with isobutyryl, and guanosine was protected with t-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 53

RNA was synthesized using 2'-TBDMS monomers. Cytidine was protected with N-(4-thiomethylphenoxycarbonyl), adenosine was protected with isobutyryl, and guanosine was protected with t-butylphenoxyacetyl. The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Example 54

RNA was synthesized using 2'-TBDMS monomers. Cytidine was protected with acetyl, adenosine was protected with isobutyryl, and guanosine was protected with N-(t-butylthiocarbamate). The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 50/50 methanol/water. This releases the RNA oligonucleotides into solution and deprotects the exocyclic amines. The RNA containing the 2'-TBDMS protecting groups was then precipitated from the hydrogen peroxide solution and exposed to a solution of HF/tetraethylene diamine (20% TEMED, 10% HF(aq) in acetonitrile at pH 8.6) for 6 hours at room temperature. The reaction mixture was diluted with water and purified by ion-exchange chromatography.

Example 55

RNA was synthesized using 2'-TBDMS monomers. Cytidine was protected with acetyl, adenosine was protected with isobutyryl, and guanosine was protected with N-(t-butylthiocarbamate). The solid support was the polystyrene based Rapp Polymere containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a solution of HF/tetraethylene diamine (20% TEMED, 10% HF(aq) in acetonitrile at pH 8.6) for 2 hours at room temperature. The fluoride ion solution was washed from the support using acetonitrile followed by water. The support was then treated with a 6% hydrogen peroxide solution buffered at pH 9.4 using aminomethylpropanol buffer in 10/90 ethanol/water for 4 hours. This releases the RNA oligonucleotides into solution and deprotects the exocyclic amines. The RNA was directly precipitated by adding 5 volumes of anhydrous ethanol, cooling on dry ice, and then isolating by centrifugation.

Deprotection with Hydrogen Peroxide Solution of Chemically Synthesized RNA on Peroxyanion Cleavable Linker with Commercially Available Exocyclic Amino Protecting Groups and Novel 2' Hydroxyl Protecting Groups Example 56

RNA was synthesized using 2'-tert-butylthiocarbonate (BSC) protected monomers. cytidine was protected with acetyl, adenosine was protected with isobutyryl, and guanosine was protected with tert-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution, and deprotected the exocyclic amines and the 2'-BSC groups. The RNA was then directly precipitated by adding 5 volumes of anhydrous ethanol, cooling on dry ice, and then isolating by centrifugation.

Example 57

RNA was synthesized using 2'-tert-butylthiocarbonate (BSC) protected monomers. cytidine was protected with acetyl, adenosine was protected with isobutyryl, and guanosine was protected with N-(methylthiomethyloxycarbonyl). The solid support was controlled pore glass containing a peroxide oxidizable safety catch linker. Acetic anhydride capping was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

Example 58

RNA was synthesized using 2'-tert-butylthiocarbonate (BSC) protected monomers. cytidine was protected with acetyl, adenosine was protected with isobutyryl, and guanosine was protected with N-(methylthiocarbamate). The solid support was controlled pore glass containing a peroxide oxidizable safety catch linker. Acetic anhydride capping was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water.

This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

Example 59

RNA was synthesized using 2'-tert-butylthiocarbonate (BSC) protected monomers. cytidine was protected with acetyl, adenosine was protected with isobutyryl, and guanosine was protected with N-thiomethylacetyl. The solid support was controlled pore glass containing a peroxide oxidizable safety catch linker. Acetic anhydride capping was removed from the synthesis cycle. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

Example 60

RNA was synthesized using 2'-tert-butylthiocarbonate (BSC) protected monomers. cytidine was protected with acetyl, adenosine was protected with isobutyryl, and guanosine was protected with N-(carbonyloxy-1-phethylthiomethyl-1-H-isobutane). The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This releases the RNA oligonucleotides into solution and deprotects the exocyclic amines and the 2'-BSC groups. The RNA was then directly precipitated by adding 5 volumes of anhydrous ethanol, cooling on dry ice, and then isolating by centrifugation.

Example 61

RNA was synthesized using 2'-tert-butylthiocarbonate (BSC) protected monomers. cytidine was protected with acetyl, adenosine was protected with isobutyryl, and guanosine was protected with N-(carbonyloxy-1-methylthiomethylcyclohexane). The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This releases the RNA oligonucleotides into solution and deprotects the exocyclic amines and the 2'-BSC groups. The RNA was then directly precipitated by adding 5 volumes of anhydrous ethanol, cooling on dry ice, and then isolating by centrifugation.

Example 62

RNA was synthesized using 2'-tert-butylthiocarbonate (BSC) protected monomers. cytidine was protected with acetyl, adenosine was protected with N-(4-thiomethyl-benzoyl), guanosine was protected with tert-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

Example 63

RNA was synthesized using 2'-tert-butylthiocarbonate (BSC) protected monomers. cytidine was protected with acetyl, adenosine was protected with N-(2-thiomethyl-benzoyl), guanosine was protected with tert-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using arninomethylpropanol buffer in 10/90 ethanol/water. This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

Example 64

RNA was synthesized using 2'-tert-butylthiocarbonate (BSC) protected monomers. cytidine was protected with N-(2-thiomethylphenoxycarbonyl), adenosine was protected with isobutyryl, and guanosine was protected with tert-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution and deprotected the exocyclic amines and the 2'-BSC groups. The RNA was then directly precipitated by

Example 65

RNA was synthesized using 2'-tert-butylthiocarbonate (BSC) protected monomers. cytidine was protected with N-(4-thiomethylphenoxycarbonyl), adenosine was protected with isobutyryl, and guanosine was protected with tert-butylphenoxyacetyl. The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

Example 66

RNA was synthesized using 2'-tert-butylthiocarbonate (BSC) protected monomers. cytidine was protected with acetyl, adenosine was protected with isobutyryl, and guanosine was protected with N-(tert-butylthiocarbamate). The solid support was controlled pore glass containing a peroxide oxidizable safety catch linker. Following synthesis, the methyl protecting groups on the phosphodiesters were cleaved using 1 M disodium-2-carbamoyl-2-cyanoethylene-1,1-dithiolate trihydrate in DMF for 30 minutes. The deprotection solution was washed from the solid support bound oligonucleotide using water. The support was then treated with a 6% hydrogen peroxide solution buffered at pH 9.4 using aminomethylpropanol buffer in 10/90 ethanol/water. This released the RNA oligonucleotides into solution and deprotected the exocyclic amines and the 2'-BSC groups. The RNA was then directly precipitated by adding 5 volumes of anhydrous ethanol, cooling on dry ice, and then isolating by centrifugation.

O-4 Protection on Uridine

When a carbonyl protective group was present on the 2'-hydroxyl that contains a strong electron withdrawing group, a molecular ion minus 52 Dalton (M-52) side product has been observed in the mass spectroscopy analysis of such RNA products and only associated with the incorporation of uridine. Although not intending to be bound by theory, the product may be the result of Michael addition at the C-6 carbon of the heterobase followed by nucleophillic acyl substitution at the C-4 carbon, resulting in formation of a urea.

Figure 17:
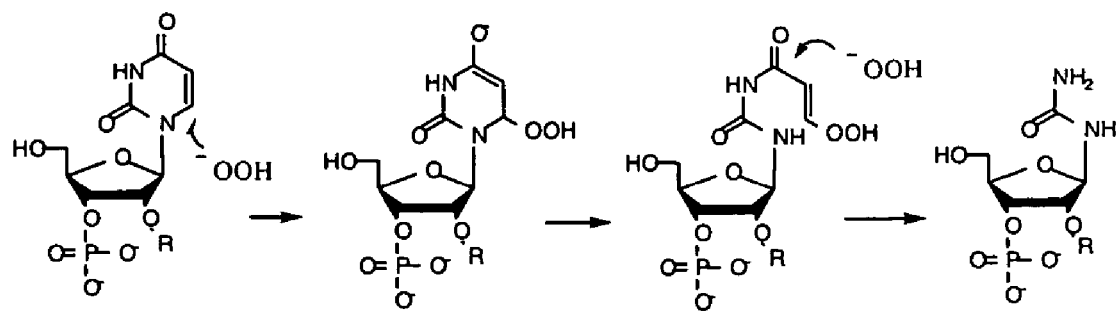
FIG. 17 illustrates the Michael addition at the C-6 carbon of the heterobase followed by nucleophillic acyl substitution at the C-4 carbon resulting in formation of a urea.

FIG. 17 illustrates a Michael addition at the C-6 carbon of the heterobase followed by nucleophillic acyl substitution at the C-4 carbon, resulting in formation of a urea. However, this mechanism can be avoided by employing O-4 protection as described below.

Figure 18:
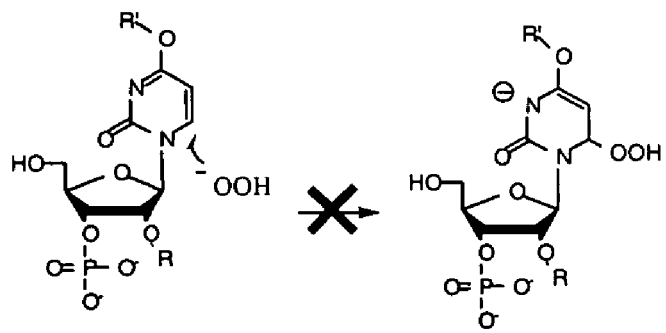
FIG. 18 illustrates that O-4 protection prevents initial Michael addition at C-6.

FIG. 18 illustrates that an O-4 protection prevents initial Michael addition at C-6.

O-4 Protecting on Uridine can be Quite Convenient and high Yielding by Employing the Formation of a Triazole Deravitive as Described by (Reference)

Figure 19:
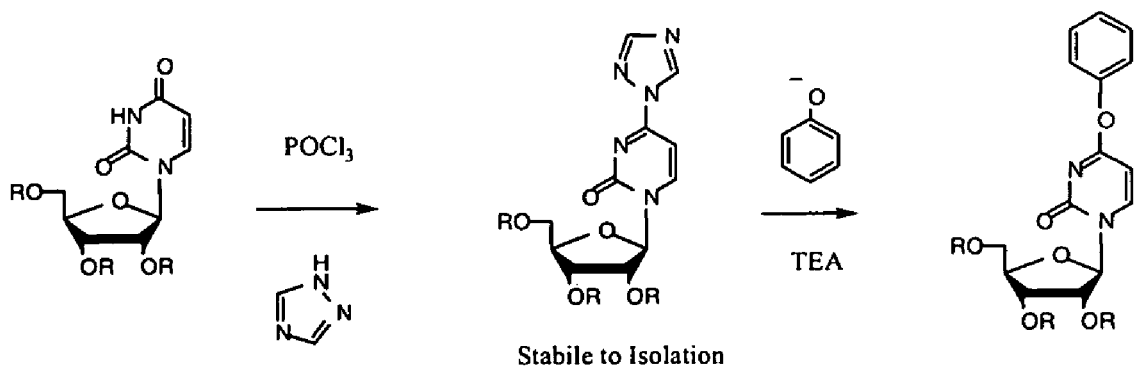
FIG. 19 illustrates the formation of C-4 triazolide.

FIG. 19 illustrates the formation of C-4 triazolide. Because the triazolide intermediate was quite stable to isolate, it can easily fit into a regioselective scheme for monomer synthesis.

Figure 20:
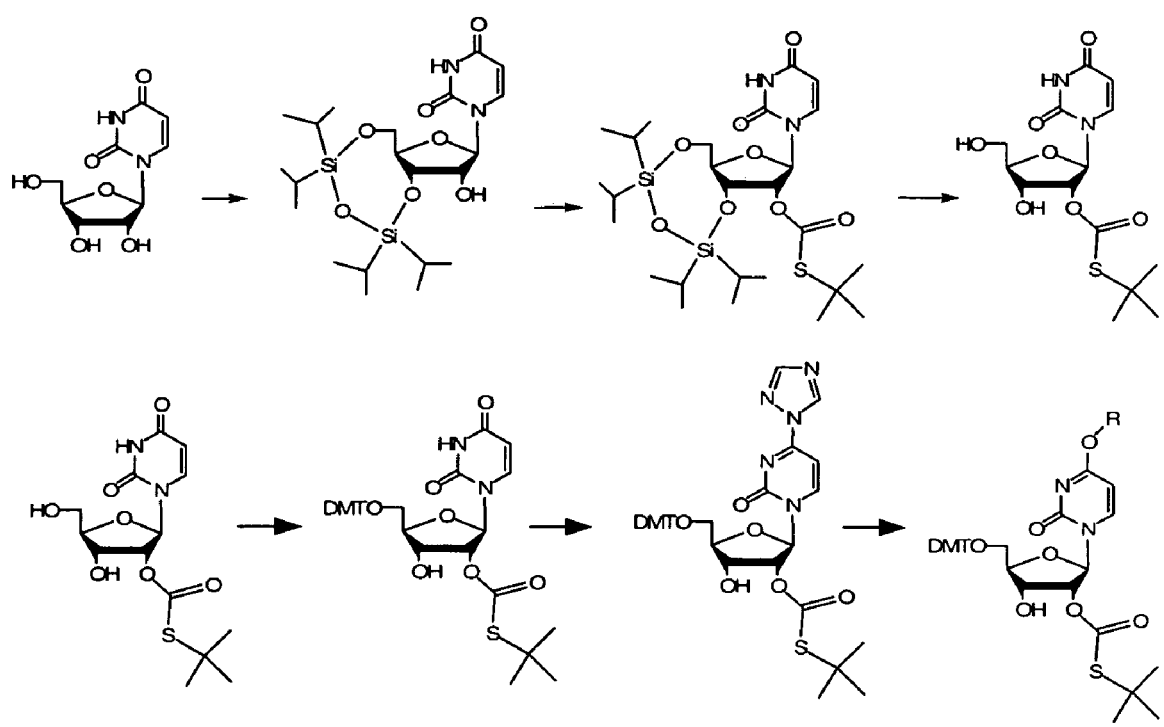
FIG. 20 illustrates the regiospecific synthesis of a 2'-protected nucleoside with O-4 protection.

FIG. 20 illustrates the regiospecific synthesis of 2'-Protected Nucleoside with O-4 protection.

HPLC Chromatograms of RNA Synthesized by the Present Disclosure

Figure 21:
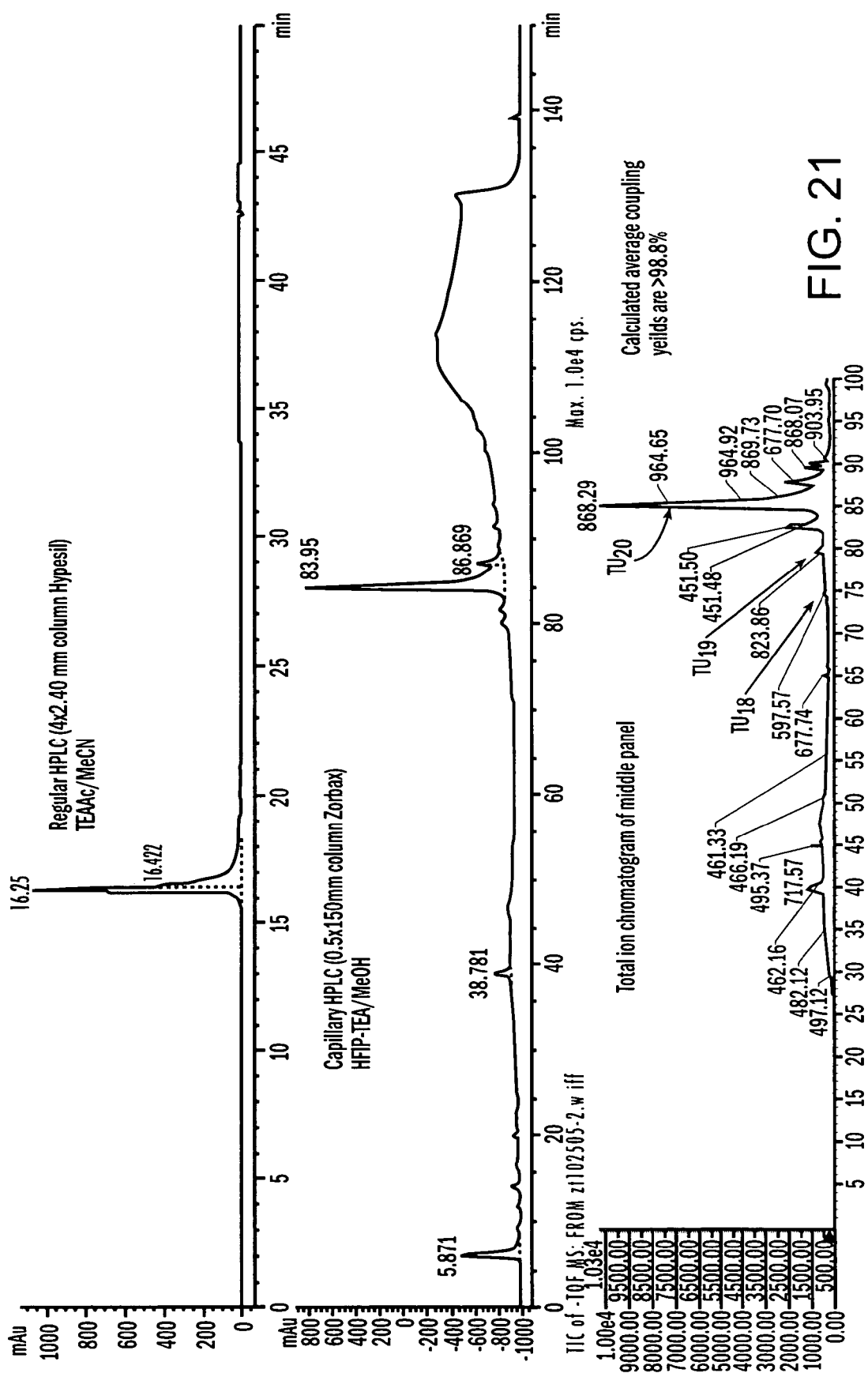
FIG. 21 illustrates HPLC Chromatograms of RNA synthesized by the present disclosure.

CPG-Q-T-$(U^{2'Bsc})_{20}$ was synthesized by regular 4-step DMT chemistry on CPG-Q-T using DMTrU$^{2'Bsc}$OMe phosphoramidite, and then the product was treated with MeCN/TEMED/HF (4/1/0.5) (40 min), neutralized (TRIS pH 7.4), and filtered on Sephadex column. FIG. 21 illustrates fraction 3 on RP HPLC.

Figure 22:
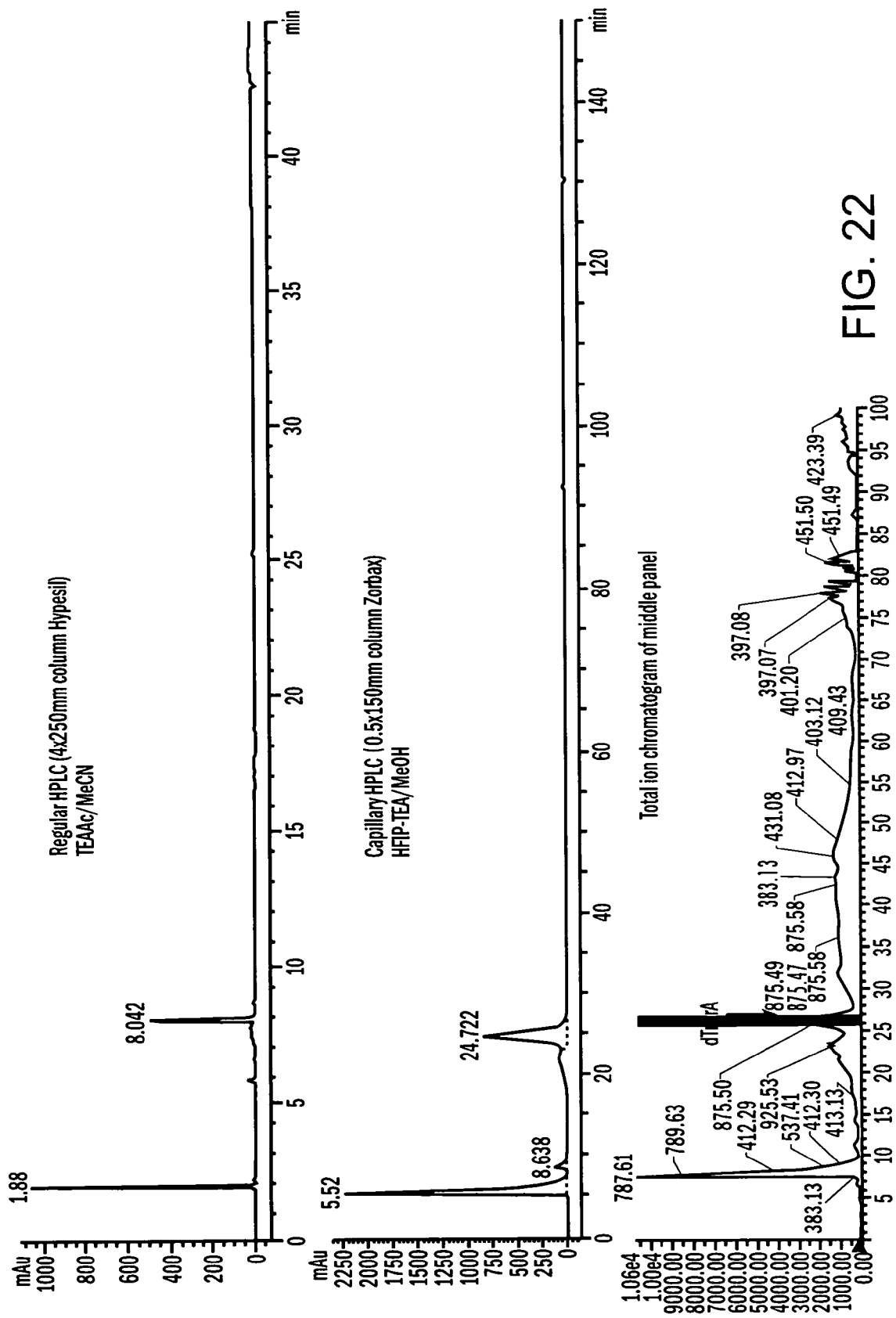
FIG. 22 illustrates HPLC Chromatograms of RNA synthesized by the present disclosure.

CPG-Q-T-rC-rA was synthesized by regular 4-step DMT chemistry with DMTrC$^{Ac}_{2'Bsc}$ OMe phosphoramidite and DMTrA$^{ibu}_{2'Bsc}$ OMe phosphoramidite. The product was cleaved (off the CPG, the Bsc and Ac from C, and ibu from A) by 5% $H_2O_2$ (pH 9.4, 50 mM alkaline buffer, 10% MeOH), and the crude cleavage mixture was analysed by HPLC (regular) (FIG. 22, upper panel) and LC-MS (capillary HPLC) (FIG. 22, on middle panel). FIG. 22 illustrates the TIC (on the lower panel).

Figure 23:
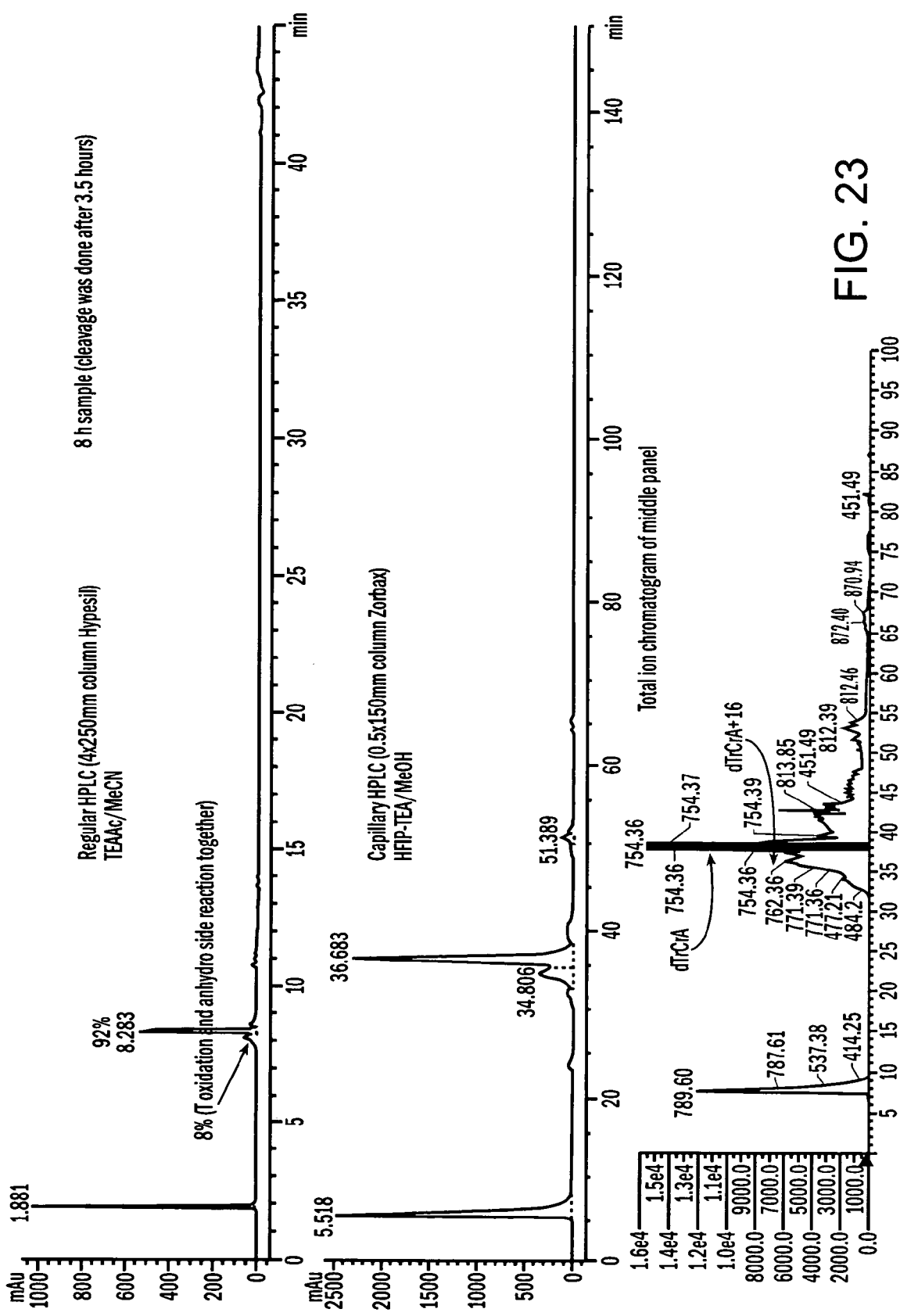
FIG. 23 illustrates HPLC Chromatograms of RNA synthesized by the present disclosure.

CPG-Q-T-rCrArCrA was synthesized by regular 4-step DMT chemistry with DMTrC$^{Ac}_{2'Bsc}$ OMe phosphoramidite and DMTrA$^{ibu}_{2'Bsc}$ OMe phosphoramidite. Analysis was similar to dTrCrA (FIG. 23).

---

What is claimed is:

1. A nucleotide monomer comprising: a compound of structure I having a 2'-hydroxyl protecting group:

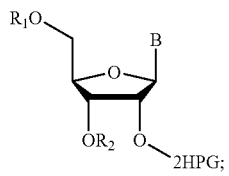

Structure I wherein B is selected from a base and a base including a base protecting group;

wherein $R_1$ and $R_2$ are each independently selected from H, a hydroxyl protecting group, and

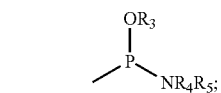

wherein either $R_1$ or $R_2$ is

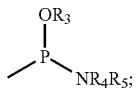

wherein $R_3$ is selected from an alkyl group, an aryl group, a substituted alkyl, and a substituted aryl group;

wherein $R_4$ and $R_5$ are each independently selected from an alkyl group, an aryl group, a substituted alkyl, and a substituted aryl group; and wherein 2HPG is a 2'-hydroxyl protecting group selected from one of the following groups:

Group II:

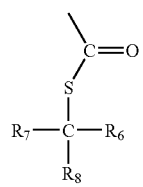

Group II wherein $R_6$, $R_7$, and $R_8$ are each independently selected from an alkyl group, an aryl group, a substituted alkyl group, and a substituted aryl group;

Groups VIIa and VIIb:

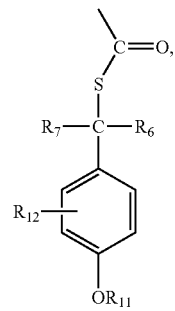

Group VIIa

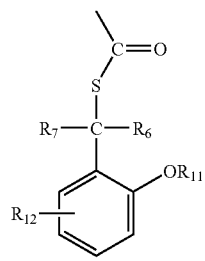

Group VIIb wherein $R_6$ and $R_7$ are independently selected from an alkyl group, an aryl group, a substituted alkyl with an electron-withdrawing group, and a substituted aryl group with an electron-withdrawing group, wherein $R_{11}$ is selected from an ester protecting group and a silyl protecting group, wherein each $R_{12}$ is one or more groups, wherein $R_{12}$ is bonded to a carbon on the ring, wherein each $R_{12}$ is selected from an alkyl group, an aryl group, a substituted alkyl with an electron-withdrawing group, and a substituted aryl group with an electron-withdrawing group; and Group VIII:

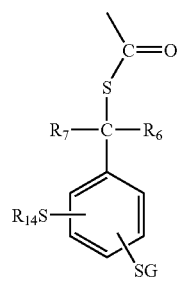

Group VIII wherein $R_6$ and $R_7$ are independently selected from an alkyl group, an aryl group, a substituted alkyl with an electron-withdrawing group, and a substituted aryl group with an electron-withdrawing group, wherein $SR_{14}$ includes one or more groups, wherein each $SR_{14}$ is attached to one of the carbons in the carbon ring, wherein each $SR_{14}$ is a thioether selected from a thioalkyl group, a thioaryl group, a substituted thioalkyl group, a substituted thioaryl group, wherein $R_{14}$ is selected from an alkyl group, an aryl group, a substituted alkyl group, a substituted aryl group, and wherein SG includes one or more groups, wherein each SG is attached to one of the carbons in the carbon ring, wherein each SG is selected from H, an alkyl group, an aryl group, a substituted alkyl with an electron-donating group, a substituted aryl group with an electron-donating group, and an electron-donating group in the ortho or para position to the thioether $SR_{14}$.

2. The nucleotide monomer of claim 1, wherein 2HPG is Group II.

3. The nucleotide monomer of claim 2, wherein $R_6$, $R_7$, and $R_8$ are each a methyl group.

4. The nucleotide monomer of claim 1, wherein 2HPG is Group VIIb.

5. The nucleotide monomer of claim 1, wherein 2HPG is Group VIII.

6. The nucleotide monomer of claim 1, wherein two or more of $R_6$, $R_7$, and $R_8$ of Group II are cyclically connected to each other.

7. The nucleotide monomer of claim 1, wherein for Groups VIIa and VIIb, $R_6$ and $R_7$ are cyclically connected to each other or to the phenyl group.

8. The nucleotide monomer of claim 1, wherein for Group VIII, $R_6$ and $R_7$ are cyclically connected to each other or to the phenyl group.

9. The nucleotide monomer of claim 1, wherein B is a base including a base protecting group selected from groups Ic through Xc:

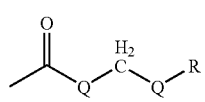

Group Ic

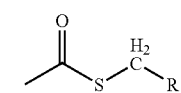

Group IIc

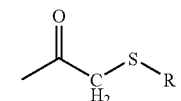

Group IIIc

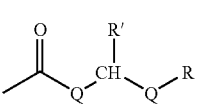

Group IVc

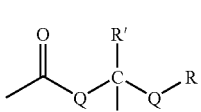

Group Vc

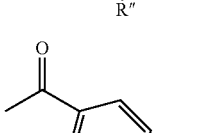

Group VIc

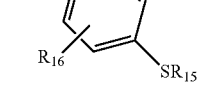

Group VIIc

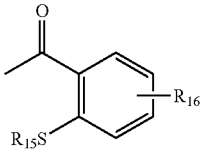

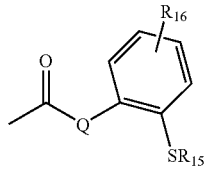

Group VIIIc

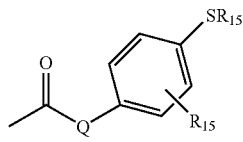

Group IXc

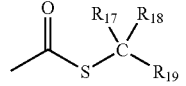

Group Xc wherein Q is selected from one of sulfur (S) and oxygen (O); R is selected from an alkyl group, a substituted alkyl group, an aryl group, and a substituted aryl group; R' and R" are independently selected from a halogen, an alkyl group, a substituted alkyl group, an aryl group, and a substituted aryl group; $R_{15}$ is selected from an alkyl group, an aryl group, a substituted alkyl, and a substituted aryl group; $R_{16}$ is one or more groups, wherein each $R_{16}$ is attached to one of the carbons in the carbon ring, wherein each $R_{16}$ are independently selected from H, a halogen, a hydroxyl group, an alkoxy group, a substituted alkoxy group, an aryloxy group, a substituted aryloxy group, an amino group, a substituted amino group, a nitro group, a nitrile group, an alkyl group, an aryl group, a substituted alkyl, and a substituted aryl group, wherein when $R_{16}$ is more than one, two or more of $R_{16}$ are optionally cyclically connected to each other; and $R_{17}$, $R_{18}$, and $R_{19}$, are each independently selected from H, an alkyl group, an aryl group, a substituted alkyl, and a substituted aryl group.

10. A nucleotide monomer comprising: a structure II having a 2'-hydroxyl protecting group and a heterobase exocyclic amino protecting group:

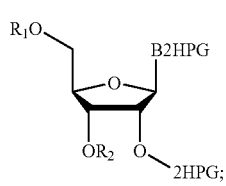

Structure II wherein $R_1$ and $R_2$ are each independently selected from H, a hydroxyl protecting group, and

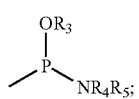

wherein either $R_1$ or $R_2$ is

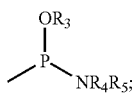

wherein $R_3$ is selected from an alkyl group, an aryl group, a substituted alkyl, and a substituted aryl group;
wherein $R_4$ and $R_5$ are each independently selected from an alkyl group, an aryl group, a substituted alkyl, and a substituted aryl group; and
wherein 2HPG is identical for both the 2'-hydroxyl protecting group and the heterobase exocyclic amino protected group and selected from one of the following groups:

Group II:

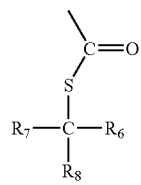

Group II wherein $R_6$, $R_7$, and $R_8$ are each independently selected from an alkyl group, an aryl group, a substituted alkyl group, and a substituted aryl group;

Groups VIIa and VIIb:

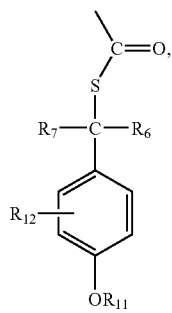

Group VIIa

Group VIIb

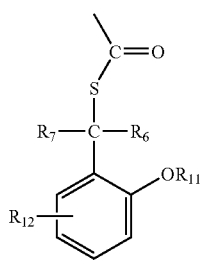

wherein $R_6$ and $R_7$ are independently selected from an alkyl group, an aryl group, a substituted alkyl with an electron-withdrawing group, and a substituted aryl group with an electron-withdrawing group, wherein $R_{11}$ is selected from an ester protecting group and a silyl protecting group, wherein each $R_{12}$ is one or more groups, wherein $R_{12}$ is bonded to a carbon on the ring, wherein each $R_{12}$ is selected from an alkyl group, an aryl group, a substituted alkyl with an electron-withdrawing group, and a substituted aryl group with an electron-withdrawing group; and Group VIII:

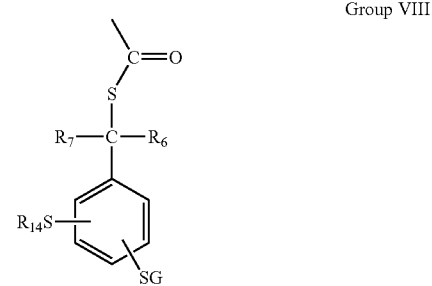

Group VIII wherein $R_6$ and $R_7$ are independently selected from an alkyl group, an aryl group, a substituted alkyl with an electron-withdrawing group, and a substituted aryl group with an electron-withdrawing group, wherein $SR_{14}$ includes one or more groups, wherein each $SR_{14}$ is attached to one of the carbons in the carbon ring, wherein each $SR_{14}$ is a thioether selected from a thioalkyl group, a thioaryl group, a substituted thioalkyl group, a substituted thioaryl group, wherein $R_{14}$ is selected from an alkyl group, an aryl group, a substituted alkyl group, a substituted aryl group, and wherein SG includes one or more groups, wherein each SG is attached to one of the carbons in the carbon ring, wherein each SG is selected from H, an alkyl group, an aryl group, a substituted alkyl with an electron-donating group, a substituted aryl group with an electron-donating group, and an electron-donating group in the ortho or para position to the thioether $SR_{14}$.

11. The nucleotide monomer of claim 10, wherein 2HPG is Group II.

12. The nucleotide monomer of claim 11, wherein R6, R7, R8 are each a methyl group.

13. The nucleotide monomer of claim 10, wherein 2HPG is Group VIIa.

14. The nucleotide monomer of claim 10, wherein 2HPG is Group VIIb.

15. The nucleotide monomer of claim 10, wherein 2HPG is Group VIII.

16. The nucleotide monomer of claim 10, wherein two or more of $R_6$, $R_7$, and $R_8$ of group II are cyclically connected to each other.

17. The nucleotide monomer of claim 10, wherein for group VIIa, $R_6$ and $R_7$ are cyclically connected to each other or to the phenyl group.

18. The nucleotide monomer of claim 10, wherein for group VIII, $R_6$ and $R_7$ are cyclically connected to each other or to the phenyl group.

19. The nucleotide monomer of claim 10, wherein for group VIIb, $R_6$ and $R_7$ are cyclically connected to each other or to the phenyl group.

20. The nucleotide monomer of claim 10, wherein B is a base including a protecting group selected from base protecting groups that are removed under a same set of conditions as the 2HPG.

21. The nucleotide monomer of claim 10, wherein B is a base including a protecting group selected from base protecting groups that are removed under a different set of conditions than the 2HPG.

22. The nucleotide monomer of claim 10, wherein B is a base including a protecting group selected from: acetyl, chloroacetyl, dicholoracetyl, trichloroacetyl, fluoroacetyl, difluoroacetyl, trifluoroacetyl, nitroacetyl, propionyl, n-butyryl, i-butyryl, n-pentanoyl, i-pentanoyl, t-pentanoyl, phenoxyacetyl, 2-chlorophenoxyacetyl, t-butyl-phenoxyacetyl, methylthioacetyl, phenylthioacetyl, 2-chlorophenylthioacetyl, 3-chlorophenylthioacetyl, 4-chlorophenylthioacetyl, t-butyl-phenylthioacetyl, benzyloxycarbonyl, (9-fluoroenyl)-methoxycarbonyl (Fmoc), 2-nitrophenylsulfenyl, 4-nitrophenylethylcarbonyl, 4-nitrophenylethoxycarbonyl, diphenylcarbamoyl, morpholinocarbamoyl, dialkylformamidines, succinyl, phtaloyl, benzoyl, 4-trifluoromethylbenzoyl, 2-methylbenzoyl, 3-methylbenzoyl, 4-methylbenzoyl, 2,4-dimethylbenzoyl, 2,6-dimethylbenzoyl, 2,4,6-trimethylbenzoyl, 2-methoxybenzoyl, 3-methoxybenzoyl, 4-methoxybenzoyl, 2,4-dimethoxybenzoyl, 2,6-dimethoxybenzoyl, 2,4,6-trimethoxybenzoyl, 2-methylthiobenzoyl, 3-methylthiobenzoyl, 4- methylthiobenzoyl, 2,4-dimethylthiobenzoyl, 2,6-dimethylthiobenzoyl, 2,4,6-trimethylthiobenzoyl, 2-chlorobenzoyl, 3-chlorobenzoyl, 4-chlorobenzoyl, 2,4-dichlorobenzoyl, 2,6-dicholorbenzoyl, 2-fluorobenzoyl, 3-fluorobenzoyl, 4-fluorobenzoyl, 2,4-difluorobenzoyl, 2,6-difluorobenzoyl, 2,5-difluorobenzoyl, 3,5-difluorobenzoyl, 2-trifluoromethylbenzoyl, 3-trifluoromethylbenzoyl, 2,4- trifluoromethylbenzoyl, 2,6-trifluoromethylbenzoyl, 2,5-trifluoromethylbenzoyl, 3,5-trifluoromethylbenzoyl, 2-nitrobenzoyl, 3-nitrobenzoyl, 4-nitrobenzoyl, (3-methoxy4-phenoxy)benzoyl, (triphenyl)silylethyleneoxycarbonyl, (diphenylmethyl)silylethyleneoxycarbonyl, (phenyldimethyl)silylethyleneoxycarbonyl, (trimethy)lsilylethyleneoxycarbonyl, (triphenyl)silyl(2,2-dimethyl)ethyleneoxycarbonyl, (diphenylmethyl)silyl[(2,2-dimethyl)ethylene]oxycarbonyl, phenyldimethylsilyl[(2,2-dimethyl)ethylene]oxycarbonyl, trimethylsilyl[(2,2-dimethyl)ethylene]oxycarbonyl, methyloxycarbonyl, ethyloxycarbonyl, propyloxycarbonyl, isopropyloxycarbonyl, butyloxycarbonyl, isobutyloxycarbonyl, t-butyloxycarbonyl, phenyloxycarbonyl, benzyloxycarbonyl, methylthiocarbonyl, ethylthiocarbonyl, propylthiocarbonyl, isopropylthiocarbonyl, butylthiocarbonyl, isobutylthiocarbonyl, tert-butylthiocarbonyl, phenylthiocarbonyl, benzylthiocarbonyl, methyloxymethyleneoxycarbonyl, methylthiomethylene-oxycarbonyl, phenyloxymethylene-oxycarbonyl, phenyllthiomethyleneoxycarbonyl, methyloxy(methyl)methyleneoxycarbonyl, methylthio(methyl)methyleneoxycarbonyl, methyloxy(dimethyl)methyleneoxycarbonyl, methylthio(dimethyl)methyleneoxycarbonyl, phenyloxy(methyl)methyleneoxycarbonyl, phenylthio(methyl)methyleneoxycarbonyl, phenyloxy(dimethyl)methyleneoxycarbonyl, and phenylthio(dimethyl)methyleneoxycarbonyl.

* * * * *

UNITED STATES PATENT AND TRADEMARK OFFICE
CERTIFICATE OF CORRECTION

PATENT NO. : 7,759,471 B2  Page 1 of 2
APPLICATION NO. : 11/388112
DATED : July 20, 2010
INVENTOR(S) : Douglas J Dellinger et al.

It is certified that error appears in the above-identified patent and that said Letters Patent is hereby corrected as shown below:

On the face page, in field (56), under "Other Publications", in column 2, line 9, delete "2,2,2,-t-" and insert -- 2,2,2-t- --, therefor.

On the face page, in field (56), under "Other Publications", in column 2, line 11, delete "2007-2210" and insert -- 2207-2210 --, therefor.

In column 1, line 27, delete "SYNTHESIS"filed" and insert -- SYNTHESIS" filed --, therefor.

In column 90, lines 13-15, in Claim 9, delete " 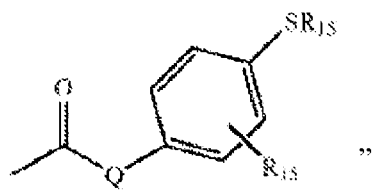 " and insert -- [structure] --, therefor.

In column 92, lines 39-40, in Claim 12, delete "R6, R7, R8" and insert -- $R_6$, $R_7$, $R_8$ --, therefor.

In column 93, line 3, in Claim 22, delete "dicholoracetyl," and insert -- dichloroacetyl, --, therefor.

In column 93, line 14, in Claim 22, delete "phtaloyl," and insert -- phthaloyl, --, therefor.

In column 93, line 20, in Claim 22, delete "4- methylthiobenzoyl," and insert -- 4-methylthiobenzoyl, --, therefor.

In column 93, lines 26-27, in Claim 22, delete "2,4- trifluoromethylbenzoyl," and insert -- 2,4-trifluoromethylbenzoyl, --, therefor.

Signed and Sealed this

Twenty-third Day of November, 2010

David J. Kappos
*Director of the United States Patent and Trademark Office*

CERTIFICATE OF CORRECTION (continued)
U.S. Pat. No. 7,759,471 B2

In column 94, lines 2-3, in Claim 22, delete "(3-methoxy4-phenoxy)benzoyl," and insert -- (3-methoxy 4-phenoxy)benzoyl, --, therefor.

In column 94, lines 5-6, in Claim 22, delete "(trimethy)lsilylethyleneoxycarbonyl," and insert -- (trimethyl)silylethyleneoxycarbonyl, --, therefor.

In column 94, lines 18-19, in Claim 22, delete "phenyllthiomethyleneoxycarbonyl," and insert -- phenylthiomethyleneoxycarbonyl, --, therefor.